US006733965B2

(12) United States Patent
Echt et al.

(10) Patent No.: US 6,733,965 B2

(45) Date of Patent: May 11, 2004

(54) MICROSATELLITE DNA MARKERS AND USES THEREOF

(75) Inventors: Craig S. Echt, Ocean Springs, MS (US); C. Dana Nelson, Ocean Springs, MS (US)

(73) Assignees: International Paper Company, Purchase, NY (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/232,785

(22) Filed: Jan. 19, 1999

(65) Prior Publication Data

US 2003/0049612 A1 Mar. 13, 2003

Related U.S. Application Data

(63) Continuation-in-part of application No. 09/232,884, filed on Jan. 15, 1999, now abandoned.

(51) Int. Cl.[7] .......................... C12Q 1/68; C12P 19/34; G01N 33/00; C07H 21/02; C07H 21/04

(52) U.S. Cl. ........................... 435/6; 435/91.1; 436/94; 536/23.1; 536/24.3; 536/24.33

(58) Field of Search .......................... 435/6, 91.1, 91.2, 435/183; 436/94; 536/23.1, 24.3, 24.33, 25.3

(56) References Cited

U.S. PATENT DOCUMENTS

| | | | |
|---|---|---|---|
| 5,378,602 | A | 1/1995 | Polymeropoulos et al. |
| 5,582,979 | A | 12/1996 | Weber |
| 5,674,687 | A | 10/1997 | Hershfield |
| 5,695,933 | A | 12/1997 | Schalling et al. |
| 5,705,343 | A | 1/1998 | Drayna et al. |
| 5,721,100 | A | 2/1998 | Polymeropoulos et al. |
| 5,843,647 | A | 12/1998 | Jeffreys et al. |

OTHER PUBLICATIONS

Sommer et al., Minimal homology requirements for PCR primers. Nucleic Acids Res. 17, 6749, 1989.*

Sambrook et al., Molecular Cloning: A Laboratory Manual, p. 11.7, 1989, Published by Cold Spring Harbor Laboratory Press, 10 Skyline Drive, Plainview, New York 11803.*

Sommer et al, Minimal Homology Requiremnets For PCR Primers. Nucleic Acids Res., 1989, vol. 17, No. 16, p. 6749.

Sambrook et al., Molecular Cloning: A Laboratory Manual, 1989, Second Edition, p. 11.7, Published by Cold Spring Harbor Laboratory Press, Plainview, New York.

Powell, W. et al., *Proc. Natl. Acad. Sci. USA,* 92:7759–7763, Aug. 1995.

Fisher, P.J. et al., *Nucleic Acid Research,* 24(21):4369–4371, 1996.

Smith, D.N. et al., *Genome,* 37:977–983, 1994.

Echt, C.S. et al., *Genome,* 40:9–17, 1997.

Echt, C.S. et al., *Genome,* 39:1102–1108, 1996.

* cited by examiner

*Primary Examiner*—Ethan Whisenant
*Assistant Examiner*—Frank Lu
(74) *Attorney, Agent, or Firm*—Darby & Darby

(57) ABSTRACT

Microsatellite, simple sequence repeat (SSR), markers have much potential for enhancing genome mapping and genotype identification research in forest genetics and tree breeding, SSR markers were developed by isolating and sequencing 1539 loblolly pine SSR clones for 11 SSR motifs. After screening out redundancy among the sequences, 566 oligonucleotide PCR primer pairs flanking the SSRs were synthesized and evaluated for their ability to amplify genomic DNA from loblolly pine. The three SSR motifs that yielded the highest proportion of informative markers from sequenced clones were $(AC)_n$, $(AAAT)_n$, and $(AAAC)_n$. Eighteen polymorphic tri- and tetranucleotide SSR loci were genotyped in 20 loblolly pine trees using automated fluorescent marker analysis. The average number of alleles per locus observed was 6.4, and the average polymorphism information content (PIC) was 0.547. Subsets of the 566 primer pairs were evaluated for their ability to amplify DNA from six other pine species, and 54 primer pairs amplified markers that were polymorphic among the species. The present invention also concerns the methods of using the identified SSR loci as genetic markers.

23 Claims, No Drawings

MICROSATELLITE DNA MARKERS AND USES THEREOF

This application is a continuation-in-part application of U.S. application Ser. No. 09/232,884 filed Jan. 15, 1999, now abandoned, entitled Microsatelite DNA Markers and Uses thereof, which is hereby incorporated herein by reference.

FIELD OF THE INVENTION

The invention relates to identification and isolation of the simple sequence repeat (SSR) loci in the higher eukaryotes, such as the plants, and particularly the pines. The SSR loci of the invention are particularly useful as genetic markers for genetic mapping, population genetics studies and inheritance studies in various plant breeding programs.

BACKGROUND OF THE INVENTION

Loblolly pine (*Pinus taeda* L.) is an important, experimental and commercial forest tree species native to the southeastern United States. Loblolly pine is planted extensively in the southeastern United States and to lesser degrees in other warm temperate regions of the world. In the United States, plantations are managed and utilized for a variety of products including raw materials (wood, fiber, and chemicals), ecosystem components (wildlife habitat and water and soil conservation), and recreational activities. Most of planting stock originates from production seed orchards established by various loblolly pine improvement programs. To date, such programs have completed one to three cycles of selection using progeny testing for parental selection and seed orchard development, and family and within-family testing and selection for population improvement. Loblolly pine breeding has various limitations, such as, long generation times to flower (>5 years) and harvest (>15 years), low tolerance to inbreeding, large size of individual trees, variable sites for testing and replanting, difficulty of vegetative propagation, low heritability of important traits, and uncertainty of trait values.

Marker-assisted selection (MAS) using DNA-based markers has much potential for improving the efficiency and effectivenes of tree breeding programs (O'Malley and McKeand 1994 *For. Genet.* 1:207–218.). Important improvements afforded by MAS include reducing the time-to-selection and improving the accuracy of selection. An important goal of such research is to identify DNA markers or other measures that predict performance of mature trees. With this information, tree breeders could more confidently select trees at an early age, induce them to flower, and breed them to produce the next generation. In addition, selections made at an early age could be vegetatively propagated in mass using rooted cutting or tissue culture based technologies (Bradshaw and Foster 1992 *Can. J. For. Res.*, 22:1044–1049.). Vegetative propagation and deployment has the potential to greatly improve wood and fiber yield and quality by capturing within-family genetic variation and providing better performing varieites for plantation establishment.

Several of the fundamental limitations to MAS applications in loblolly pine (Strauss et al. 1992 *Can. J. For. Res.*, 22:1050–1061.) have been overcome in recent years. Most notably is the application of randomly-primed, PCR-based genetic markers (e.g., RAPD) to parent- or family-specific genome mapping (Tulsieram et al. 1992, *Biotechnology*, 10:686–690; Nelson et al 1994 *Journal of Heredity*, 85:433–439; Plomion et al. 1996 *Theor. Appl. Genet.*, 93:1083–1089., Wilcox et al. 1996 *Proc. Natl. Acad. Sci. USA*, 93:3859–3864.). Although family-specific mapping and MAS approaches have potential, these methods are limited to situations where small breeding (<10 parents) populations are maintained with progeny established in large-family (n>500) tests. In practice, however, most loblolly pine breeding programs do not fit this situation. More typical is large breeding populations, sometimes several populations per program, and always relatively small-family (n<150) progeny tests. In addition most programs now include many pedigrees of at least three-generations, with nearly mature third-generation trees in the field. Utilizing existing extensive pedigree and progeny test information is essential for developing better MAS technology and improving breeding programs.

Currently available marker systems are not optimal for detecting QTL variation across families and across multi-generation pedigrees. Reviews of current marker technologies and their limitations to use in QTL mapping and MAS is provided by Neale and Harry (1994 *AgBiotech News Info.*, 6:107N–114N.) and O'Malley and Whetten (1997 *Molecular markers and forest trees. DNA Markers: Protocols, Application and Overviews* ed. G. Caetano-Anollés and P. M. Gresshoff. John Wiley and Sons, New York., 237–257.). Given a genome size of about 2000 cM(K) for loblolly pine, a large number of highly polymorphic, co-dominant genetic markers will be needed for genome mapping and QTL analyses (Echt and Nelson 1997 *Theor. Appl. Genet.*, 94:1031–1037.).

Accordingly, there is a need in the art for new genetic markers. In an effort to develop such markers for loblolly pine, the pines and the plants in general, the present inventors developed simple sequence repeat (SSR) markers described herein. The markers of the invention are also useful for other eukaryotic organisms.

SUMMARY OF THE INVENTION

Simple sequence repeats (SSRs), which are also known as microsatellite DNA repeats, have now been discovered in the pines and have been shown to exhibit length polymorphisms. These repeats represent an abundant pool of potential genetic markers.

Accordingly, in one aspect, the present invention relates to the plant SSR motifs, such as for example, di-, tri- and tetra-nucleotide repeated motifs.

In another aspect, the invention relates to the polynucleotides containing one or more such SSR motifs and the primers for the amplification of the fragments containing SSRs. The primers may be cloned polynucleotide fragments or chemically synthesized oligonucleotides, and contain at least a portion of the non-repeated, non-polymorphic sequence fang SSRs on either 5' or 3' end.

The present invention is also directed to a kit for the rapid analysis of one or more specific DNA polymorphisms of the type described in this application The kit includes oligodeoxynucleotide primers for the amplification of fragments containing one or more SSR sequences.

In a further aspect, the invention provides for a method of analyzing one or more specific SSR polymorphisms in an individual or a population, which involves amplification of small segment(s) of DNA containing the SSR and non-repeated flanking DNA by using the polymerase chain reaction, and sizing the resulting amplified DNA, preferably by electrophoresis on polyacrylamide gels.

In yet another aspect, the invention provides for a method of determining the sequence information necessary for primer production by isolation and sequencing of DNA fragments containing the SSRS, using hybridization of a synthetic, cloned, amplified or genomic probe, containing sequences substantially homologous to the SSR, to the DNA.

In a further aspect, the present invention is directed to a method for detecting the presence of a specific trait in a subject, such as a plant. The method includes isolating the genomic DNA from the subject individual and analyzing the genomic DNA with a polymorphic amplified DNA marker containing one or more SSR sequences.

In yet another aspect, the SSR markers of the invention are used in commercial plant breeding. Traits of economic importance in plant crops can be identified through linkage analysis using polymorphic DNA markers.

DETAILED DESCRIPTION OF THE INVENTION

All patents, patent applications and references cited in this specification are hereby incorporated herein by reference in their entirety. In case of any inconsistency, the present disclosure governs.

Definitions

The following terms and phrases are used throughout the specification with the following intended meanings.

The abbreviation "SSR" stands for a "simple sequence repeat" and refers to any short sequence, for example, a mono-, di-, tri-, or tetra-nucleotide that is repeated at least once in a particular nucleotide sequence. These sequences are also known in the art as "microsatellites." A SSR can be represented by the general formula $(N_1N_2 \ldots N_i)_n$, wherein N represents nucleotides A, T, C or G, i represents the number of the nucleotides in the base repeat, and n represents the number of times the base is repeated in a particular DNA sequence. The base repeat, i.e., $N_1N_2 \ldots N_i$, is also referred to herein as an "SSR motif." For example, $(ATC)_4$, refers to a tri-nucleotide ATC motif that is repeated four times in a particular sequence. In other words, $(ATC)_4$ is a shorthand version of "ATCATCATCATC."

The term "complement of a SSR motif" refers to a complementary strand of the represented motif. For example, the complement of (ATG) motif is (TAC).

The term "permutations of a SSR motif" refers to all possible combinations of a motif found within the repeated sequence of that motif. For example, permutations of the $(ATG)_5$ motif (i.e., ATGATGATGATGATG) are TGA and GAT as both can be found in this repeat.

The term "perfect repeat" refers to a repeated SSR motif without interruption and without adjacent repeat(s) of a different motif. However, the repeats may be "imperfect" when a repeated SSR motif is interrupted by a number of non-repeated nucleotides, such as for example in $(AC)_5GCTAGT(AC)_7$. Other possible variations of SSRs would be known to those of skill in the art. These repeats, including compound repeats, are defined by Weber, J. L., 1990, *Genomics*, 7:524–530.

The term "compound repeat" refers to a SSR that contains at least two different repeated motifs that may be separated by a stretch of non-repeated nucleotides. An example of a compound repeat is $(ATC)_5(AT)_6$.

The term "SSR locus" refers to a location on a chromosome of a SSR motif; locus may be occupied by any one of the alleles of the repeated motif. "Allele" is one of several alternative forms of the SSR motif occupying a given locus on the chromosome. For example, the $(ATC)_8$ locus refers to the fragment of the chromosome containing this repeat, while $(ATC)_4$ and $(ATC)_7$ repeats represent two different alleles of the $(ATC)_8$ locus. As used herein, the term locus refers to the repeated SSR motif and the flanking 5' and 3' non-repeated sequences. SSR loci of the invention are useful as genetic markers, such as for determination of polymorphysm.

"Polymorphism" is a condition in DNA in which the most frequent variant (or allele) has a population frequency which does not exceed 99%.

The term "heterozygosity" (H) is used when a fraction of individuals in a population have different alleles at a particular locus (as opposed to two copies of the same allele). Heterozygosity is the probability that an individual in the population is heterozygous at the locus. Heterozygosity is usually expressed as a percentage (%), ranging from 0 to 100%, or on a scale from 0 to 1.

The term "informativeness" is a measure of the utility of the polymorphism. In general, higher informativeness means greater utility. Informativeness is usually defined in terms of either heterozygosity or "Polymorphism Information Content" (PIC) (for PIC see Botstein, D., et al., 1980, *Am. J. Hum. Genet.*, 32, 314–331). The PIC represents the probability that the parental origin of an allele can be determined from the marker genotype of the locus in any given offspring. The PIC values range from 0 to 1.0, and are smaller in value than heterozygosities. The formulas for calculating H and PIC are disclosed in the examples. For markers that are highly informative (heterozygosities exceeding about 70%), the difference between heterozygosity and PIC is slight.

"Primers" are short polynucleotides or oligonucleotides required for a polymerase chain reaction that are complementary to a portion of the polynucleotide to be amplified. The phrase "primer adapted for detection of a SSR marker" means that the primer is capable of amplyfying a particular SSR locus to be used as a marker, wherein the primer is complementary to either the 5' or the 3' non-repeated region of the SSR locus and is of a length suitable for use as a primer. For example, the primer is no more than 50 nucleotides long, preferably less than about 30 nucleotides long, and most preferably less than about 24 nucleotides long.

The term "polynucleotide" is intended to include double or single stranded genomic and cDNA, RNA, any synthetic and genetically manipulated polynucleotide, and both sense and anti-sense strands together or individually (although only sense or anti-sense stand may be represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

An "isolated" nucleic acid or polynucleotide as used herein refers to a component that is removed from its original environment (for example, its natural environment if it is naturally occurring). An isolated nucleic acid or polypeptide may contains less than about 50%, preferably less than about 75%, and most preferably less than about 90%, of the cellular components with which it was originally associated. A polynucleotide amplified using PCR so that it is sufficiently and easily distinguishable (on a gel from example) from the rest of the cellular components is considered "isolated". The polynucleotides of the invention may be "substantially pure," i.e., having the highest degree of purity that can be achieved using purification techniques known in the art.

The term "hybridization" refers to a process in which a strand of nucleic acid joins with a complementary strand through base pairing.

Polynucleotides are "hybridizable" to each other when at least one strand of one polynucleotide can anneal to a strand of another polynucleotide under defined stringency conditions. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarily over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarily between the hybridizing sequences. (1×SSC is 0.15 M NaCl, 0.015 M Na citrate.) As used herein, the above solutions and temperatures refer to the probe-washing stage of the hybridization procedure. The term "a polynucleotide that hybridizes under stringent (low, intermediate) conditions" is intended to encompass both single and double-stranded polynucleotides although only one strand will hybridize to the complementary strand of another polynucleotide.

The term "% identity" refers to the percentage of the nucleotides of one polynucleotide that are identical to the nucleotides of another sequence of identical length (excluding the length of the SSR) as implemented by the National Center for Biotechnology Information. The % identity value may be determined using a PowerBlast program (Zhang and Madden 1977 *Genome Res*. 7:649–56.).

The term "% homology" between the sequences is a function of the number of matching positions shared by two sequences divided by the number of positions compared and then multiplied by 100. This comparison is made when two sequences are aligned (by introducing gaps if needed) to give maximum homology. PowerBlast program, implemented by the National Center for Biotechnology Information, is used to compute optimal, gapped alignments. Alternatively, the % homology comparison may be determined using a Blast 2.0 program implemented by the National Center for Biotechnology Information.

SSR Motifs and SSR Loci of the Invention

The present invention relates to SSR motifs and SSR loci useful as genetic markers in various organisms, particularly plants. In a preferred embodiment of the invention, the SSR motifs and loci originate from the pines, such as the pines of the Pinus genus, for example *P. taeda, P. caribaea, P. ponderosa, P. radiata, P. resinosa, P. strobus*, and *P. sylvestris*. As seen from the list of exemplary species, the pines and SSRs thereof of the present invention can belong to either of the two subgenera of the Pinus genus. *P. strobus* (white pine) is a species of the Strobus subgenus, and *P. taeda, P. caribaea, P. ponderosa, P. radiata, P. resinosa*, and *P. sylvestris* are exemplary species of the Pinus subgenus.

The SSR motifs of the invention have the general formula $(N_1, N_2 \ldots N_i)_n$, wherein: N represents nucleotides A, T, C or G; i represents the number of the last nucleotide in the SSR motif; and n represents the number of times the SSR motif is repeated in the SSR locus. In one embodiment of the invention, the total number of nucleotides in a motif (i) is about six, preferably four, three or two. The total number of repeats (n) may be from 1 to about 60, preferably from 4 to 40, and most preferably from 10 to 30 when i=2; preferably 4–25, and most preferably 6–22 when i=3; and preferably 4–15, and most preferably 5–10 when i=4. Any SSR motif of the above formula is within the scope of the invention, however, the following SSR motif are preferred: AC, AAC, AAG, AAT, ACC, ACG, AGG, ATC, AAAC, AAAT, AGAT and all complements and permutation of said motifs, such as for example ATG, CAT, TTG, TTA, TTC, ATT, and TAT. Compound repeats are also within the scope of the invention. Examples of such repeats are: $(A)_n \ldots (ATG)_n$; $(ATG)_n \ldots (C)_n$; $(CAT)_n \ldots (A)_n$; $(ACC)_n \ldots (ATC)_n$; $(TTG)_n$; … $(TTA)_n$; $(C)_n \ldots (ATT)_n$; $(TAT)_n \ldots (A)_n$; $(ATT)_n \ldots (AAT)_n$; $(TTC)_n \ldots (T)_n$; and $(A)_n(AAAC)_n(A)_n$.

The SSR loci of the invention are preferably a maximum about 500 nucleotides long. In another preferred embodiment, the SSR locus of the invention is a minimum of 50 nucleotides long.

The invention further provides for isolated polynucleotides comprising at least one SSR motif and having the nucleotide sequences as shown in Table 3 (SEQ ID NOS: 237 to 354). These polynucleotides may be of the same length as the sequences shown in Table 3 or alternatively comprise additional sequences on their 5', 3' or both ends. The latter polynucleotides may be less than about 500 bp, less than about 1 kb, less than about 2 kb or less than about 3 kb long. In an embodiment of the invention, the polynucleotides comprising the sequences of SEQ ID NOS: 237–354 do not containing any functional gene or coding sequences.

Further within the scope of the invention are polynucleotides that (i) hybridize under the conditions of low, medium or high stringency to the polynucleotides comprising the sequences of SEQ ID NOS: 237–354 and (ii) contain SSR motifs. In certain embodiment of the invention, these hybridizable polynucleotides are less than about 1000 bp long, more preferably less than about 500 bp long and most preferably less than about 200 bp long. In one embodiment of the invention, the hybridizable polynucleotide is about the same length as the polynucleotide to which it hybridizes.

Also within the scope of the invention are polynucleotides that contain SSR motifs and have at least about 75%, preferably at least about 85%, and most preferably at least about 95% identity to the polynucleotides having the sequence of SEQ ID NOS:237 to 354.

Polynucleotides that contain SSR motifs and have at least about 75%, preferably at least about 85%, and most preferably at least about 95% homology to the polynucleotides having the sequence of SEQ ID NOS:237 to 354 are also within the scope of the invention.

In one preferred embodiment of the invention, polynucleotides that align to polynucleotides of SEQ ID NO:237–354 under the following conditions are also within the scope of the invention: alignment done using PowerBlast network client on PowerMacG3, when the search is set to high stringency (M=1, N=−5, S=80, S2=80) for blastn, without gap alignment. Most preferably, these polynucleotides are not of human origin.

In another preferred embodiment of the invention, polynucleotides that align to polynucleotides of SEQ ID NO:237–354 under the following conditions are also within the scope of the invention: alignment done using either PowerBlast or Blast 2.0 program using the following parameters: match=1, mismatch=−2, gap open=5, gap extension=2, x_dropoff=50, expect=10, and wordsize=9. Most preferably, these polynucleotides are not of human origin.

Isolated polynucleotides comprising at least one SSR motif and having the property of being amplifiable from a genomic DNA using PCR and any of the primer pairs disclosed in Tables 2 and 7 are also within the scope of the invention. These polynucleotides may be identified and isolated by amplification of any genomic DNA. Prefereably, genomic DNA used is a plant DNA, more preferably the pine DNA and most preferably the DNA from the Pinus genus. For example, genomic DNA may be from *P. taeda, P. caribaea, P. ponderosa, P. radiata, P. resinosa, P. strobus*, or *P. sylvestris*. In one embodyment of the invention, these polynucleotides are less than about 500 bp long. However, the length of the amplified DNA fragment is generally limited only by the resolving power of the particular separation system used. The thin denaturing gels, for example, are capable of resolving fragments differing by as little as 1 base up to a total fragment length of about 300 bp. Use of longer gels and longer electrophoresis times can extend the resolving power up to about 600 bp or more. However, the longer the fragment, the lower the proportion of its length is occupied by the SSR sequences, and hence the resolution is more difficult.

Oligonucleotide primer adapted for detection of SSR marker are also within the scope of the invention. A suitable primer comprises at least the sequence of SEQ ID NOS:1–236 and 367–390.

The present invention also provides probes specific to at least part of the aforesaid SSRs for detecting SSR markers using methods other than polymerase chain reaction, such as for example hybridization with labeled probes. The probes useful in the invention may be any sequence comprising at least the sequence of SEQ ID NOS: 1–236, as well as any other probe that a person of skill in the art can construct based on the information of SEQ ID NOS: 237–354.

The SSR loci of the invention may be polymorphic. They may have a PIC of at least 30% (0.3); preferably of at least 70% (0.7); and most preferably of at least 90% (0.9).

The polynucleotides and primers of the invention may be subcloned and introduced into various host cells according to methods well known in the art. The resulting clones and host cell are also within the scope of the invention. A person of skill in the art can make all such constructs and host cells using methods known in the art. However, the following non-limiting examples are provided below.

A large number of vectors, including bacterial, fungal and plant vectors, have been described for replication and/or expression in a variety of eukaryotic and prokaryotic hosts. Non-limiting examples include pKK plasmids (Clonetech, Palo Alto, Calif.), pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

Suitable host cells may be transformed/transfected/infected as appropriate by any suitable method including electroporation, $CaCl_2$ mediated DNA uptake, fungal infection, microinjection, microprojectile transformation, or other established methods. Appropriate host cells include bacteria, archaebacteria, fungi, especially yeast, and plant and animal cells. Of particular interest are *E. coli, B. subtilis, Saccharomyces cerevisiae, Saccharomyces carlsbergensis, Schizosaccharomyces pombi*, SF9 cells, C129 cells, 293 cells, Neurospora, CHO cells, COS cells, HeLa cells, and immortalized mammalian myeloid and lymphoid cell lines. Preferred replication systems include M13, ColE1, SV40, baculovirus, lambda, adenovirus, and the like.

The present invention is also directed to a kit for the rapid analysis of one or more specific DNA polymorphisms of the type described in this application. The kit includes oligodeoxynucleotide primers for the amplification of fragments containing one or more SSR sequences.

Development and Use of Polymorphic DNA Markers

The present invention provides for the methods of identifying and isolating SSR loci and their use as genetic markers.

In one embodyment, a method for the identification from genomic DNA of a fragment comprising a SSR locus comprising the steps of: (i) contacting a DNA library with at least one hybridisation probe so as to identify a population of DNA fragments enriched for simple tandem repeats; (ii) isolating and cloning said population; and (iii) screening of the resulting DNA library so as to identify an individual fragment comprising a simple tandem repeat locus.

The DNA library may be a genomic DNA library; the genomic DNA library may be any convenient population of DNA fragments such as pine DNA, or subgenomic DNA libraries such as those generated by PCR from flow sorted chromosomes (see Telenius, H., et al., 1992, *Genomics* 13: 718–725). The genomic DNA library may be obtained by restriction digestion of genomic DNA. The average fragment size within the DNA library may be less than 1.5 kilobases and may be less than about one kilobase. The fragment size may be from about 400 bp to about 1000 bp.

The hybridisation probe or set of probes may be immobilised on a solid phase such as a nylon membrane and may be used to identify a particular class of SSRS. Such classes may include dimeric, trimeric, tetrameric, pentameric and hexameric repeats. Particular oligonucleotide probes for use in the present invention may include oligonucleotide probes comprising a repeated region of greater than 200 bp. The probe may comprise repeats having at least 70%, such as 85% or 100%, identity to a given repeat sequence. The hybridisation probe may be a set of probes comprising mixed trimeric or tetrameric repeat DNA or any other combination of various SSR motifs.

The population of DNA fragments enriched for SSR may be amplified prior to cloning and this may be effected by PCR amplification. Universal linker sequences may be ligated to the ends of individual fragments, possibly prior to the enrichment procedure, and linker sequence specific primers may then be used to amplify the enriched population. Linker sequences may then be removed, for example by restriction digestion, prior to cloning.

In another embodiment, a method for the identification from genomic DNA of a fragment comprising a SSR locus comprises the steps of: (i) ligating universal linker sequences to the ends of fragments comprised in a genomic DNA library so as to form a library for PCR amplification; (ii) contacting said PCR library with at least one hybridisation probe so as to identify a population of library fragments enriched for simple tandem repeats; (iii) separating and amplifying said population by PCR; and (iv) cloning and screening the resulting amplification products so as to isolate an individual fragment comprising a simple tandem repeat locus.

Cloning may be effected using any convenient cloning procedure and vector (for example pBluescriptII (Stratagene, Lajolla, Calif.)) such as those described by Sambrook, J., Fritsch, E. F. and Maniatis, T. (1989), Molecular Cloning A Laboratory Manual, Cold Spring Harbor Laboratory Press.

Screening may be effected using any convenient hybridisation probe or set of probes comprising SSR sequences. These may be the same as those disclosed above in respect of the enrichment procedure.

A more detailed description of possible ways of detecting SSR loci is provided in the Examples.

Individual clones comprising SSR loci may be analyzed using conventional techniques to determine, for example, specific sequence information. Such techniques may allow the generation of individual "identities" specific for one or more polymorphic loci. The generation of such individuals "identities" may be used to identify and characterise family relationships and may be used for e.g. trait tracing in a breeding program and in any other technique which uses SSRs and their polymorphisms.

According to a further aspect of the present invention there are also provided methods of genetic characterisation wherein sample DNA is characterised by reference to at least one of the SSR loci, primer sequences and probes of the invention. The method of genetic characterisation may comprise either the use of at least one hybridisation probe or it may comprise the use of polymerase chain reaction (PCR) primers specific to at least one of the SSR loci in order to amplify selectively the SSR locus. The PCR primers may comprise at least one of the primers and probes of the present invention. The method of genetic characterisation may be used in genetic mapping studies such as linkage studies, and may be used in the genetic analysis of inherited traits.

In one embodyment, the present invention is directed to a method for detecting the presence of a specific trait in a subject, such as a plant. The method includes isolating the genomic DNA from the subject individual and analyzing the genomic DNA with a polymorphic amplified DNA marker containing one or more SSR sequences. The analysis comprises amplification using the polymerase chain reaction of one or more short DNA fragments containing the SSR followed by measurement of the sizes of the amplified fragments using gel electrophoresis.

Examples of using SSR markers of the invention for detection of polymorphism in various pines are provided in the Examples. Any other known uses of such markers will be apparent to persons of skill in the art.

Throughout the present application, the standard IUPAC nucleotide representation was used. It should be noted that in these, K=G or T (keto); Y=C or T (pYrimidine); R=A or G (puRine); M=A or C (aMino); S=G or C (strong 3H bond); B=C, G or T; D=A, G or T; H=A, C or T; and V=A, C or G.

The present invention is further described in the following non-limiting examples.

EXAMPLES

Materials and Methods

Genetic Stocks

The source of DNA used for clone library construction was needle tissue from a vegetative clone of the *P. taeda* tree known as 7–56. Allele diversity surveys were based on needle tissue DNA from vegetative clones of 26 trees that were selected from breeding populations established from five geographic origins. The sample origins included South and North Carolina Atlantic Coastal Plain (15 trees) and Piedmont (2 trees), central Florida (4 trees), southeast Louisiana (4 trees) and central Mississippi (1 tree). For some analyses the trees were classified into two groups—South and North Carolina Atlantic Coastal Plain (ACP) and the others (non-ACP).

SSR Cloning, and Sequence Analysis

The primer extension and uracil N-glycosylase selection procedure of Ostrander et al. (1992), as described by Echt et al. (1996) *Genome,* 39:1102–1108, was used with minor modifications (use of exonuclease I and lambda exonuclease as described below) for small-insert, SSR-enriched clone library construction. Enriched libraries were individually constructed for the following SSR motifs: AC, AAC, AAG, AAT, ACC, ACG, AGG, ATC, AAAC, and AAAT. Some commercial preparations of Taq DNA polymerase contained DNA fragments that provided non-specific polymerase priming sites during the primer extension step, thus primer extension reaction components were treated with exonuclease I and lambda exonuclease to remove extraneous oligonucleotides a and increase the proportion of SSR-specific extensions.

Alkaline phosphatase-conjugated oligonucleotide probes specific for each SSR motif were used for chemiluminescent detection and identification of bacterial clones carrying SSR inserts. Probe hybridizations were done on either colony lift, or 96-well arrayed, nylon membranes. Only a single round of SSR clone identification and isolation was used prior to DNA sequence analysis. Di- and trinucleotide primers and probes were all 30 nucleotides in length, while the tetranucleotide primers and probes were 32 nucleotides long.

SSR-enriched libraries constructed using a different SSR enrichment strategy were obtained from Genetic Information Services, Inc. (Chatsworth, Calif.). In brief, genomic DNA was partially digested with a cocktail of blunt-end-generating restriction endonucleases, and size fractionated and purified by agarose gel electrophoresis. The purified fragments ranging from 350 to 650 bp. were ligated with adapter oligonucleotides to provide common PCR priming sites for all fragments, and to provide a HindIII restriction endonuclease site for subsequent cloning into a pUC19 plasmid vector. The adapted fragments were denatured and hybridized to SSR oligonucleotides bound to magnetic microbeads. Non-SSR bearing fragments were washed away from the beads. SSR bearing fragments were released by denaturation, PCR amplified, and used for clone library construction. SSR probe hybridizations and detection to identify the SSR-bearing bacterial clones were done on 96-well arrayed nylon membranes, as described above.

Plasmid DNA for sequencing was prepared according to manufacturers' instructions using either Wizard Miniprep columns (Promega Corp., Madison, Wis.) or QIAPrep Spin Miniprep columns (Qiagen Inc., Valencia, Calif.). DNA cycle sequencing reactions were analyzed with either ABI 373A or 377 automated DNA analyzers, or with a LICOR 4200-2 automated DNA analyzer.

Duplicated or repeated clone sequences were identified with the contig assembly function of the Sequencher 3.0 program (GeneCodes, Inc., Ann Arbor, Mich.). Similarity searches in the non-redundant DNA sequence and EST sequence databases at the National Center for Biotechnology Information were done with the Power BLAST network client program (Zhang and Madden 1977 *Genome Res.* 7:649–56.). Primer pair sequences specific to regions flanking SSR sites were determined by the Primer 0.5 and Primer 3.0 programs (The Whitehead Institute, Cambridge, Mass., USA), and primer oligonucleotides were synthesized by Research Genetics, Inc., Huntsville, Ala. SSR locus names refer to the institutions and species of origin (i.e., RIPPT= Rhinelander and International Paper, *Pinus taeda*), followed by a clone identifier number.

Marker Amplification and Analysis

PCR amplification and agarose gel electrophoresis were done as described by Echt et al. (1996). PCR amplification success and locus polymorphism were evaluated on high-resolution agarose gels containing 3% TreviGel-500 (Trevigen, Inc., Gaithersburg, Md.). Precise allele sizing and locus genotyping were done by fluorescent marker analysis on an ABI373A Automated DNA Analyzer running GeneScan software (PE Applied Biosystems, Foster City, Calif.).

Polymorphism potential in *P. taeda* was evaluated for each marker using one of two methods. In the first, 18 or 20 loblolly pine trees were genotyped for each marker (RIPPT1 through RIPPT89). Methods described by Liu (1998, Statistical Genomics: Linkage, Mapping, and QTL Analysis, CRC Press, Boca Raton, Fla. 611 p.) were used to calculate heterozygosity (H) and the polymorphism information content (PIC). The H is the probability that an individual in the population is heterozygous at the locus. The PIC is the probability that the parental origin of an allele can be determined from the marker genotype of the locus in any given offspring (Botstein et al. 1980 *Am. J. Hum. Genet*., 32: 314–331.). Following Liu (1998, Statistical Genomics: Linkage, Mapping, and QTL Analysis, CRC Press, Boca Raton, Fla. 611 p.):

$$H = 1 - \sum_{i=1}^{l} pii$$

and $$PIC = 2\sum_{i=2}^{l}\sum_{j=2}^{i=1}[pipj(1 - pipj)]$$

where l is the number of codominant alleles at the locus, $p_{ii}$ is the frequency of homozygous genotypes, and p is the frequency of ith or jth allele.

The second method used a two-step strategy to identify polymorphism. For the primary screen, an individual tree and a pool of eight other individuals from both ACP and non-ACP geographic origins were PCR amplified for each marker locus (RIPPT100 through RIPPT9325), giving four samples of template DNA. Polymorphism was recorded when, following high resolution agarose gel electrophoresis, a pooled sample displayed more alleles than the individual sample from the same pool, or when size differences were observed between the ACP and non-ACP samples. For the secondary screen, single, polymorphic SSR loci identified from the primary screen were amplified from eight individuals (four trees each from both the ACP and non-ACP groups), and allelic size differences were scored from high-resolution agarose gels.

Results and Discussion

Enrichment Cloning

Relative abundance of certain SSR motifs in the loblolly pine genome was previously shown (Echt and May-Marquardt 1997). However, the results described herein establish that there is no correlation between the abundance of a certain SSR motif and its polymorphism and the value as a marker.

The proportion of SSR clones in each of the enriched libraries varied from 1% to 15%, depending on the target motif, specific sequence of the oligonucleotide extension primer, and experimental conditions. No correlations were found between the SSR motif and the level of enrichment of a particular library. A total of 644 SSR clones were sequenced, with an average insert size of 400 bp.

Generally higher levels of enrichment for SSR clones were found in libraries constructed by bead capture enrichment method, where the fraction of positive clones varied from 90% for the $(AC)_n$ enriched library to 1.5% for the $(AAT)_n$ enriched library. For the six motifs targeted for this method of enrichment, AC, AAG, AAT, AAAC, AAAT, and AGAT, the mean fraction of SSR-positive clones in the enriched libraries was 34%. A total of 995 cloned inserts were sequenced, with an average insert size of 465 bp. Similarities between DNA and protein database sequences and the 110 cloned *P. taeda* sequences that were developed into informative marker loci were evaluated using a PowerBlast network client (Zhang and Madden 1997 *Genome Res,* 7:649–56.) running blastn and blastx alignment functions. No significant or functional similarities were found.

The best motifs for yielding informative markers were AC, AAAT, and AAAC, although the rate of conversion from sequences SSR clone to polymorphic marker is still rather low (Table 1).

TABLE 1

Frequency of sequenced cloned inserts, unique cloned sequences, primers pairs synthesized, single loci that were PCR amplified, and polymorphic SSR loci, by motif.

| SSR motif | clones sequenced | unique sequences | primer pairs | primer pairs amplifying a single locus | polymorphic single loci[a] | polymorphic loci per sequenced clone (%) |
|---|---|---|---|---|---|---|
| AC | 605 | 430 | 315 | 121 | 76 | 12.6 |
| AAC | 58 | 22 | 20 | 11 | 0 | 0 |
| AAG | 55 | 43 | 67 | 28 | 2 | 3.6 |
| AAT | 187 | 90 | 40 | 26 | 7 | 3.7 |
| ACC | 7 | 0 | 16 | 4 | 0 | 0 |
| ACG | 12 | 10 | 10 | 1 | 0 | 0 |
| AGG | 14 | 12 | 2 | 1 | 0 | 0 |
| ATC | 298 | 108 | 53 | 34 | 11 | 3.7 |
| AAAC | 117 | 67 | 15 | 13 | 6 | 5.1 |
| AAAT | 98 | 59 | 21 | 15 | 8 | 8.2 |
| AGAT | 68 | 26 | 7 | 1 | 0 | 0 |
| total | 1539 | 887 | 566 | 255 | 110 | 3.35 (mean) |

[a]among 18 *P. taeda* trees, as evaluated in high-resolution agarose gels

Clones of $(AC)_n$, $(AAAT)_n$, and $(AAAC)_n$, loci had respective conversion frequencies from sequenced clones to single locus polymorphic markers of 12.6%, 8.2% and 5.1%. $(AGAT)_n$, which yields many informative markers in mammalian species, produced no markers for loblolly pine.

The trinucleotide repeats that were examined did not, in general, prove to be a very good source of polymorphic markers despite their relative abundance in the pine genome reported by Echt and May-Marquardt 1997. The three trinucleotide motifs that did produce polymorphic markers had a sequence-to-marker conversion frequency of about 3.7%

(Table 1). The ATC motif, the most abundant trinucleotide SSR in loblolly pine (Echt and May-Marquardt 1997), accounted for relatively few informative markers. It appeared to be associated with a repetitive DNA function in the genome, as only 36% of the $(ATC)_n$ clones sequenced were unique sequences. $(AAT)_n$ SSRs produced similarly few polymorphic loci, even though in soybean they are a good source of informative markers (Akkaya et al. 1995 *Crop Science*, 35:1439–1445; Rongwen et al. 1995 *Theor. Appl. Genet*., 90:43–48.).

SSR Locus Polymorphism

For both enrichment methods, the total numbers of clones sequenced, PCR primer pairs designed, and polymorphic marker loci discovered are presented in Table 1. Of the 566 primer pairs evaluated, 164 gave no amplification, 255 amplified a single fragment, 77 amplified two distinct fragments, and 70 amplified more than two distinct fragments. A list of 119 primer pairs used to amplify *P. taeda* SSR loci is represented in Table 2.

TABLE 2

| Locus | Forward sequence | Reverse sequence | Nr. loci | P = polymorph | Expected | Size (bp) | Null allele segregating |
|---|---|---|---|---|---|---|---|
| RIPPT1 | GCATGCCAAAAGATCTCAA (SEQ ID NO:1) | AGTGAACTCGGGAGGCTTCT (SEQ ID NO: 2) | 1P | | 263 | | N |
| RIPPT6 | TTTGGACAAGTGGCTTGTTG (SEQ ID NO: 3) | ATGTTTGATTGCATGGGGAT (SEQ ID NO: 4) | 1P | | 295 | | N |
| RIPPT11 | GGCTTCTCTCCAAGCTTTTTG (SEQ ID NO: 5) | GAATGAGCCTCCCAACTCAA (SEQ ID NO: 6) | 1P | | 171 | | N |
| RIPPT22 | CTCAGTTTCATAATCTTTGTCGC (SEQ ID NO: 7) | TTTTAGAAAAGAAGGAAATCTTCA (SEQ ID NO: 8) | 1P | | 250 | | N |
| RIPPT24 | GACACCGGATACTGAGGTGG (SEQ ID NO: 9) | CCCGCAACTTCGTAAGAGTC (SEQ ID NO: 10) | 1P | | 151 | | N |
| RIPPT31 | CCAACCAATGTGGTTCATCA (SEQ ID NO: 11) | AGGAAAATAGAAGGGAATAAGACC (SEQ ID NO: 12) | | 1P | | 261 | N |
| RIPPT32 | TAGCAGGTTACAACCTGGGG (SEQ ID NO: 13) | AGCCCAATTGATGGGAAATT (SEQ ID NO: 14) | | 1P | | 188 | N |
| RIPPT33 | TTGGAGAACATGCTTGCAAG (SEQ ID NO: 15) | TGGAGCATTTTCCACAAAAT (SEQ ID NO: 16) | 1P | | 181 | | N |
| RIPPT64 | GCAGCGTAATCAGATGGTCA (SEQ ID NO: 17) | CGGAAGGCGAGTTGAAGATA (SEQ ID NO: 18) | 1P | | 258 | | N |
| RIPPT65 | CCAACAGCACTTACCCAAAA (SEQ ID NO: 19) | AGCCTCATGAAAGCCCAGTA (SEQ ID NO: 20) | 1P | | 142 | | N |
| RIPPT66 | GTTGATAGAGTTTCATGTGGTGC (SEQ ID NO: 21) | TGGATGAAGAATTTTGTAGTCAA (SEQ ID NO: 22) | 1P | | 114 | | N |
| RIPPT67 | AGCCCTCCAAGACCAAGATT (SEQ ID NO: 23) | CCATTTGCAAATACCCCAAC (SEQ ID NO: 24) | 1P | | 227 | | N |
| RIPPT69 | TCAAGAATGGGGGATGATTC (SEQ ID NO: 25) | TTGCATCCAACAACTGCTTC (SEQ ID NO: 26) | 1P | | 150 | | N |
| RIPPT71 | CTACTCAAAGTGCTTGGGCA (SEQ ID NO: 27) | CCCCTTCCCTTTCTATCTGC (SEQ ID NO: 28) | 1 | | 246 | | N |
| RIPPT77 | ACACCGGATACTGAGGTGGA (SEQ ID NO: 29) | GGTTGTAGCCTCCCGTAGGT (SEQ ID NO: 30) | 1 | | 175 | | Y |
| RIPPT79 | TGATTTGATCCCTCTAGGCG (SEQ ID NO: 31) | AATCTTGAAAAGAAATTCAATATGAGA (SEQ ID NO: 32) | 1 | | 153 | | N |
| RIPPT80 | CACACAACCAAAATTAAAACATTCA (SEQ ID NO: 33) | CACAAACAAGGGGGTCTCAT (SEQ ID NO: 34) | | 2 | | 251 | Y |
| RIPPT89 | ACGAAACCCCGAGTTGATAA (SEQ ID NO: 35) | TAAGCCCTTGAACATGGTGG (SEQ ID NO: 36) | 1 | | 225 | | N |
| RIPPT101 | ATGTTTGATGGGGTCGTCAT (SEQ ID NO: 37) | CATCATCCCATCAGACAACG (SEQ ID NO: 38) | 1 | | 100 | | N |
| RIPPT103 | CCCCTTGGTGGAACAACATA (SEQ ID NO: 39) | TTGGAAAATGGCGGAATTTA (SEQ ID NO: 40) | 1 | | 210 | | N |
| RIPPT104 | TGCATTTCATTTTTGCGTGT (SEQ ID NO: 41) | AGGACATGGAGAGTTTACACATG (SEQ ID NO: 42) | | 1 | | 164 | N |
| RIPPT106 | ATCAGATTGGTGGATCGGAG (SEQ ID NO: 43) | TGACTGATAAGGGTTTCGCC (SEQ ID NO: 44) | 2 | | 180 | | N |
| RIPPT117 | GCTTCATGATTTCTCGATCG (SEQ ID NO: 45) | TCTGCGTGGATAAAGGAATTT (SEQ ID NO: 46) | | 2 | | 208 | N |
| RIPPT123 | TCGTGTCGAAACATTGGAAA (SEQ ID NO: 47) | TATCACCTATAGCCCCGTCG (SEQ ID NO: 48) | | 1 | | 129 | N |
| RIPPT126 | TCATACCGAGAGAGGTCTTTG (SEQ ID NO: 49) | GAGCTTAATTTGTGCCTGCC (SEQ ID NO: 50) | | 1 | | 174 | N |
| RIPPT128 | CGACCCTAGTCTCTTGTGCA (SEQ ID NO: 51) | TTTTGGACCCTAAGCCAGAG (SEQ ID NO: 52) | | 1 | | 175 | Y |
| RIPPT132 | AACCGTGGTGCTCTGATACC (SEQ ID NO: 53) | TGCAAGTCAAGAGCTAGAGACAA (SEQ ID NO: 54) | 1 | | 113 | | N |
| RIPPT134 | GTTTACATTTTCCTGGGGCA (SEQ ID NO: 55) | GATTTACAAAAATCCCTGCCA (SEQ ID NO: 56) | | 1 | | 145 | N |
| RIPPT135 | CACGCATGAGCTGAGTCATAA (SEQ ID NO: 57) | TGTGTTTCCCACTATGCTAAGC (SEQ ID NO: 58) | | 1 | | 218 | N |
| RIPPT139 | ACCAACCGAGGGAGCTAAAT (SEQ ID NO: 59) | AAAAACGACATTCACTTCAACA (SEQ ID NO: 60) | | 1 | | 121 | N |
| RIPPT158 | GTGTGCCACGGATGTATGAG (SEQ ID NO: 61) | TTGCTGAAAGGGCCAGTAGT (SEQ ID NO: 62) | 2 | | 211 | | N |
| RIPPT159 | ATATGGCTTACCTCGGGTCC (SEQ ID NO: 63) | CATAAACCCATTGGGTCCAG (SEQ ID NO: 64) | 2 | | 131 | | N |
| RIPPT165 | TGGAAGCCACAATTTGTTGA (SEQ ID NO: 65) | TGCAATAAAACCATGCAACAA (SEQ ID NO: 66) | 1 | | 220 | | N |
| RIPPT166 | TTTTGAGAATGTCCGTGCG (SEQ ID NO: 67) | TGATGCATTGCAAAATCATG (SEQ ID NO: 68) | | 1 | | 155 | Y |
| RIPPT171 | TGATCCTAAGCCTTAGAAACCC (SEQ ID NO: 69) | TTTTGTCACCCATGCATATGA (SEQ ID NO: 70) | | 1 | | 207 | N |
| RIPPT179 | TGTAGGAGCACAAGCCATTG (SEQ ID NO: 71) | AACACAGTTGGACCGTTTGA (SEQ ID NO: 72) | 1 | | 170 | | N |
| RIPPT185 | TGTTTGCAAATCATGGGGTA (SEQ ID NO: 73) | CCAGTGTCCATGCCAATTTT (SEQ ID NO: 74) | 1 | | 300 | | N |
| RIPPT193 | GATCCCTTGTCCCAGAAACA (SEQ ID NO: 75) | TGTTGATGTTATGCCTGGGT (SEQ ID NO: 76) | 1 | | 163 | | N |
| RIPPT211 | GAGGGGGTCTCATACACCAA (SEQ ID NO: 77) | TGCATAGAGGATGTATTTCTTGGA (SEQ ID NO: 78) | | 1 | | 159 | N |
| RIPPT255 | TCCTCCTGAGTGGTCCCATA (SEQ ID NO: 79) | ATGGATATGAGGCCTGTTGG (SEQ ID NO: 80) | 1 | | 123 | | N |
| RIPPT263 | TTGGATTGGACCTGAATCAA (SEQ ID NO: 81) | TTGGCAGTCTTCGAGGTCTT (SEQ ID NO: 82) | 1 | | 183 | | N |
| RIPPT274 | TGTTCCTCTCAAGTGACCCC (SEQ ID NO: 83) | CTTCAGCTTCCCACCAGAAG (SEQ ID NO: 84) | 1 | | 264 | | N |
| RIPPT287 | GGAATGTATTCCCGGTTCCT (SEQ ID NO: 85) | CTCCCGGATATTGAGGAGGT (SEQ ID NO: 86) | 1 | | 224 | | N |
| RIPPT293 | CGCTACTATTGGCCGAATCT (SEQ ID NO: 87) | CTGTGAGGAAATCCCTGGAA (SEQ ID NO: 88) | 1 | | 184 | | N |
| RIPPT298 | CTTTTCCCTTTCCATGACCA (SEQ ID NO: 89) | GAGTCGAGTAACCAGGTGGC (SEQ ID NO: 90) | 1 | | 319 | | N |
| RIPPT305 | TCAATCACCAATTATTTGGCT (SEQ ID NO: 91) | GGAGTGGATGAAACTATGCCA (SEQ ID NO: 92) | 1 | | 230 | | N |
| RIPPT367 | CCAATGCATAATGCAACCAC (SEQ ID NO: 93) | TAGCCATGGTGCTCAGTCTG (SEQ ID NO: 94) | 1 | | 209 | | N |
| RIPPT369 | GGTTGTTGTGCACGAGCTTA (SEQ ID NO: 95) | TCAGTGAAGTTCAAGGGAGGTT (SEQ ID NO: 96) | | 1 | | 161 | N |

TABLE 2-continued

| Locus | Forward sequence | Reverse sequence | Nr. loci | P = polymorph | Expected | Size (bp) | Null allele segregating |
|---|---|---|---|---|---|---|---|
| RIPPT376 | AGGAATTGGTGATTCATGTGG (SEQ ID NO: 97) | ATAAAAGAATCGGCCCTGGT (SEQ ID NO: 98) | 1 | | 189 | | N |
| RIPPT388 | CACAACACTCAAACATGCTCAA (SEQ ID NO: 99) | AAGAGGATGTGAGGTCCCAA (SEQ ID NO: 100) | | 1 | | 203 | N |
| RIPPT467 | CTTGGCGACCTTGTCATACA (SEQ ID NO: 101) | GGGTCCTTAGGGATCATGGT (SEQ ID NO: 102) | 1 | | 178 | | N |
| RIPPT496 | GTAAGAGTGCCTCGGGTCTG (SEQ ID NO: 103) | GGTGGTAGGTAGATCGGCAA (SEQ ID NO: 104) | | 1 | | 203 | N |
| RIPPT508 | GGCACAGGTTGGACATCTCT (SEQ ID NO: 105) | GTGGTGGAAGGGAGATTTCA (SEQ ID NO: 106) | | 1 | | 90 | N |
| RIPPT538 | AAACACTTGGACTGGATGGG (SEQ ID NO: 107) | TTTGGAGGATGTTTGTTGCA (SEQ ID NO: 108) | | 1 | | 212 | N |
| RIPPT540 | TGTTGTCATTAGTGGTAGGATCA (SEQ ID NO: 109) | AAGCGATGTCACTTGTTGAGAA (SEQ ID NO: 110) | 1 | | 200 | | N |
| RIPPT548 | TTTTGTGGTCATTCGTTGGA (SEQ ID NO: 111) | TCACATGGAAGATTATCTCCAAA (SEQ ID NO: 112) | 1 | | 207 | | N |
| RIPPT556 | TCGTGATTACATTGCTGCCT (SEQ ID NO: 113) | TCCACAACAATGATCGCTTC (SEQ ID NO: 114) | 1 | | 183 | | N |
| RIPPT560 | CATTGGAACTTCACCGAAGG (SEQ ID NO: 115) | GTGCTATTGGGTCCAGCAAT (SEQ ID NO: 116) | | 1 | | 108 | N |
| RIPPT567 | GTTGGTGAGGAGACTTGGGA (SEQ ID NO: 117) | AAGAACAATTCCAATATGGATGA (SEQ ID NO: 118) | | 1 | | 152 | N |
| RIPPT584 | GCGAGACAGAAACGGAAAAG (SEQ ID NO: 119) | CTCTGCTAGACCGCTCAGCT (SEQ ID NO: 120) | | 1 | | 136 | N |
| RIPPT609 | CAAAATGCAGAGGGGCTTAA (SEQ ID NO: 121) | CCAGTCCATCGAATCACGTA (SEQ ID NO: 122) | | 1 | | 154 | N |
| RIPPT619 | CAGCTCTCTTAATAGCCTCGG (SEQ ID NO: 123) | GCACATAGCAACGCTGAAGA (SEQ ID NO: 124) | | 2 | | 191 | N |
| RIPPT621 | GCAAAGGGAAGCAAAGTCAT (SEQ ID NO: 125) | TTCGTCCTCTTTTGAACGAGT (SEQ ID NO: 126) | | 2 | | 154 | N |
| RIPPT627 | GACAAACAACCCTTGCGTTT (SEQ ID NO: 127) | GACCCATCAAGCCAACATG (SEQ ID NO: 128) | 1 | | 168 | | N |
| RIPPT629 | GGTTGTGCTTTCCCAGAGAG (SEQ ID NO: 129) | GAATGCAAGGTAGCCAGGAG (SEQ ID NO: 130) | | 1 | | 157 | N |
| RIPPT630 | CGCAAGCTATGATACAACGC (SEQ ID NO: 131) | TGTTGGCTGAGTGTGAAAGC (SEQ ID NO: 132) | 1 | | 157 | | N |
| RIPPT644 | GTTGTGATCCAAGTCCCCTG (SEQ ID NO: 133) | TGGTCCATTCGGTCCTATTC (SEQ ID NO: 134) | 1 | | 204 | | N |
| RIPPT647 | TGGCCATCGAACTTGTGTTA (SEQ ID NO: 135) | CACGACCACCAGTCACCTTA (SEQ ID NO: 136) | | 1 | | 214 | N |
| RIPPT649 | TAGTCGAATCGGGCCTGTAC (SEQ ID NO: 137) | TTGCTCCTCTGTGTCCTTCA (SEQ ID NO: 138) | 1 | | 218 | | N |
| RIPPT658 | TGCATGCATTACAAATGTCA (SEQ ID NO: 139) | CGCTTTTAAATCAACCAAACG (SEQ ID NO: 140) | | 1 | | 219 | N |
| RIPPT675 | ACAGATGTCAAGGCCAAAGG (SEQ ID NO: 141) | CTGCATTCAAATTACCCGCT (SEQ ID NO: 142) | | 1 | | 172 | N |
| RIPPT683 | TGAAACCAATCCTTCTGCAA (SEQ ID NO: 143) | CTGATTCCTCTGGCTTCTCG (SEQ ID NO: 144) | | 1 | | 187 | N |
| RIPPT688 | TTCAGTTATGCATTCACGAGC (SEQ ID NO: 145) | GTCCTCCTGGGTTATCCCTC (SEQ ID NO: 146) | | 1 | | 141 | N |
| RIPPT689 | GAAACTTTCCCCTACGAGCC (SEQ ID NO: 147) | TTCCCCAAAAGTTCACAGGT (SEQ ID NO: 148) | | 1 | | 158 | N |
| RIPPT690 | ATTCCTAGATGGACCTGGGG (SEQ ID NO: 149) | CGACATAAGCCCACCAAATT (SEQ ID NO: 150) | | 2 | | 142 | N |
| RIPPT692 | TGGATCGTGATCCTCTGTGA (SEQ ID NO: 151) | GCTTCCATCACATTGGGATT (SEQ ID NO: 152) | 1 | | 166 | | Y |
| RIPPT700 | TTGCAATTGCGATTAACTGC (SEQ ID NO: 153) | ATAATGGCATAGCCGAATCG (SEQ ID NO: 154) | 1 | | 180 | | N |
| RIPPT767 | TGCATAGAAAGTCGCCCTCT (SEQ ID NO: 155) | ATGCATGAGGTAACTTGGGG (SEQ ID NO: 156) | | 2 | | 186 | N |
| RIPPT789 | CATCCCAAGCATCCTCAAGT (SEQ ID NO: 157) | TCAAAAATGTGGTTTAATGGAAAA (SEQ ID NO: 158) | | 1 | | 170 | N |
| RIPPT790 | TTGTGAATTGTGTCCATGGG (SEQ ID NO: 159) | ATCGGTGAGGCTTAAACACG (SEQ ID NO: 160) | 1 | | 182 | | N |
| RIPPT791 | ATGGAAGGATCCACAACCAA (SEQ ID NO: 161) | GGGCTTGTTGCTGGTCTATG (SEQ ID NO: 162) | | 2 | | 168 | N |
| RIPPT792 | GGTTGATGATGTCGATGTTGA (SEQ ID NO: 163) | TTCTTGCAAACACAGCATGTT (SEQ ID NO: 164) | | 2 | | 202 | N |
| RIPPT799 | TGATCCTAAGCCTTAGAAACCC (SEQ ID NO: 165) | TTGTCACCCATGTCATATGATACA (SEQ ID NO: 166) | | 1 | | 209 | N |
| RIPPT814 | AAAAAGAATGAGGCGCACAC (SEQ ID NO: 167) | CCCGTTTATGGCATTGATTC (SEQ ID NO: 168) | | 2 | | 100 | N |
| RIPPT815 | GAAAACGAACAAGCCATGGT (SEQ ID NO: 169) | TGTTTACTTGCATGCATGTGTG (SEQ ID NO: 170) | | 2 | | 162 | N |
| RIPPT841 | GTGCTTCCCTTGCTTCAGAC (SEQ ID NO: 171) | GCAAATGCAAACTTTGGGTA (SEQ ID NO: 172) | 1 | | 202 | | N |
| RIPPT846 | CATTCATGGTTCCAATGTGG (SEQ ID NO: 173) | TGATAAGCGTGGATCTCGTG (SEQ ID NO: 174) | 2 | | 109 | | N |
| RIPPT852 | GTTATCCCCCATGTTGTTGC (SEQ ID NO: 175) | GGGTAGAAGCACTATGCTTTCATT (SEQ ID NO: 176) | 2 | | 213 | | N |
| RIPPT860 | TTGAGCAGACATCATCAACACT (SEQ ID NO: 177) | CCAGGTTATGCCTCAAAGAG (SEQ ID NO: 178) | | 1 | | 217 | N |
| RIPPT905 | CACGGATCTCTGGAAACCAT (SEQ ID NO: 179) | CGCTGGTTTCCCTCAGAATA (SEQ ID NO: 180) | | 1 | | 194 | N |
| RIPPT921 | GGATTTTGTTTTCCTCATAATCA (SEQ ID NO: 181) | GGGCATAGCATATGCCACTT (SEQ ID NO: 182) | | 1 | | 219 | Y |
| RIPPT932 | GCAAGACCGACTGGATTAGC (SEQ ID NO: 183) | GAGGTCATGATATGTGGTGGG (SEQ ID NO: 184) | 2 | | 130 | | N |
| RIPPT941 | CTGCGTAGCAAATCACTGGA (SEQ ID NO: 185) | TGATCTGATGTGGGATCAACA (SEQ ID NO: 186) | | 1 | | 151 | N |
| RIPPT947 | CCATTGCCCGAGCTAGTTTA (SEQ ID NO: 187) | TTATATTGGACCCAAGGCCC (SEQ ID NO: 188) | | 1 | | 214 | N |
| RIPPT958 | TGGAGTCTCGAACACTGTGG (SEQ ID NO: 189) | AATCATCCCAATGGCAACAT (SEQ ID NO: 190) | | 1 | | 111 | Y |
| RIPPT960 | GCATCCATCTTCAGCATCCT (SEQ ID NO: 191) | TTCATACGACACCTTTGAAATG (SEQ ID NO: 192) | 1 | | 188 | | N |
| RIPPT961 | CCATTAGACAAGTGCGCATG (SEQ ID NO: 193) | TGAAAAAGGAATTTCCCCAA (SEQ ID NO: 194) | | 1 | | 213 | N |

TABLE 2-continued

| Locus | Forward sequence | Reverse sequence | Nr. loci | P = polymorph | Expected | Size (bp) | Null allele segregating |
|---|---|---|---|---|---|---|---|
| RIPPT968 | TCTACGACAAAACCACGTAGTG (SEQ ID NO: 195) | CATGTGGCTTTGTGGCATAT (SEQ ID NO: 196) | | 1 | | 201 | N |
| RIPPT984 | TGTGACCTGAAAATTCCCCT (SEQ ID NO: 197) | GGCTTGCAACCAGTTCCATA (SEQ ID NO: 198) | 1 | | 220 | | N |
| RIPPT990 | GACCTAAAGAGGTTCACGCG (SEQ ID NO: 199) | TCAAATCTTGGGTTAGTATGCAGA (SEQ ID NO: 200) | | 1 | | 220 | N |
| RIPPT1013 | ATCCCTGTGGGGATGAGTTA (SEQ ID NO: 201) | TGCCTCTTAAGCATCAAATGTT (SEQ ID NO: 202) | 1 | | 124 | | N |
| RIPPT1023 | GAACCCGATGGATTTTCAAA (SEQ ID NO: 203) | CAAACTGTAAGCTCAGGAGGA (SEQ ID NO: 204) | 1 | | 175 | | N |
| RIPPT1027 | CAGTGTTGATTGTGTGCCAG (SEQ ID NO: 205) | TCTGCCACAATTTGGAAACA (SEQ ID NO: 206) | 1 | | 220 | | N |
| RIPPT1035 | AGCATAATGAGCCCTTCTCG (SEQ ID NO: 207) | AGAATATGTGTCCCTCCCCC (SEQ ID NO: 208) | 1 | | 174 | | N |
| RIPPT1036 | TGGTTGTGCGAGATCACAAT (SEQ ID NO: 209) | TTGAGGGAATTGAAATTGGG (SEQ ID NO: 210) | 1 | | 211 | | N |
| RIPPT1037 | TGCTCAATATAGACCACTTGCA (SEQ ID NO: 211) | AGCCATAATTCAACAAAAGGAA (SEQ ID NO: 212) | 1 | | 152 | | N |
| RIPPT1040 | TCAAGGAATTCATTGGAGCC (SEQ ID NO: 213) | TTTGGCCATATCAAACCCAT (SEQ ID NO: 214) | 1 | | 192 | | N |
| RIPPT1066 | AAAGGGGGTGTTTGATGGAT (SEQ ID NO: 215) | GATCGAAATCAGCGAACACA (SEQ ID NO: 216) | | 1 | | 175 | Y |
| RIPPT1072 | TTTCATGACCTTGGAGTGGA (SEQ ID NO: 217) | ATTGATCCCATTGTTGCTCC (SEQ ID NO: 218) | | 1 | | 209 | N |
| RIPPT1076 | TGTGTAAACCCAGGCTAGGC (SEQ ID NO: 219) | ATGATTTCACAAAGCCCCTC (SEQ ID NO: 220) | 1 | | 167 | | N |
| RIPPT1077 | AACATTCTAGCATGCCCCAC (SEQ ID NO: 221) | TTGTGGTGGATGTCTCTCCT (SEQ ID NO: 222) | 1 | | 220 | | N |
| RIPPT1125 | GAGCCACACAAACATGCATC (SEQ ID NO: 223) | TTTCCCAAAAGTTCACGAGG (SEQ ID NO: 224) | | 2 | | 197 | Y |
| RIPPT1137 | CCCATGCAACTGCCTAGAAT (SEQ ID NO: 225) | AAGCTCGCACGTGGGATA (SEQ ID NO: 226) | 2 | | 165 | | N |
| RIPPT9058 | CCCGCTCCTATTCAAGATCA (SEQ ID NO: 227) | AGGCGCCTAGAGGCATAATT (SEQ ID NO: 228) | 1 | | 206 | | N |
| RIPPT9104 | TTCCTATCGTCAGCGTCCAT (SEQ ID NO: 229) | GTTCACAGGGGTCATGCTTT (SEQ ID NO: 230) | 1 | | 155 | | N |
| RIPPT9138 | TGAAACCAATTTTTCCCCTTT (SEQ ID NO: 231) | CCAAGAAAGACAAGGAGCCA (SEQ ID NO: 232) | | 1 | | 229 | N |
| RIPPT9238 | CCCTGAGACATCCAATCCAT (SEQ ID NO: 233) | ACTTTACATGAGTTGGGCGG (SEQ ID NO: 234) | 1 | | 119 | | N |
| RIPPT9315 | GGCTTAGGCATAGAGGGACC (SEQ ID NO: 235) | AACAAGTTGGAAGCCACCAT (SEQ ID NO: 236) | | 1 | 219 | | N |

Polymorphism among *P. taeda* individuals was scored using high resolution agarose gel electrophoresis. Heterozygous marker alleles having a 3 bp size difference could be resolved and 2 bp allele size differences between samples in adjacent lanes could be detected. Since single bp allelic differences were not detectable some 2 bp allelic differences were possibly missed, the number of polymorphic loci reported may be slightly underestimated. In table 1, the number of polymorphic single loci reflects the number of primer pairs generating a single major DNA fragment, or a heterozygote fragment pattern. For most primer pairs, there was only one fragment amplified. In a few cases additional amplification of a weakly amplified fragment, or fragments, well outside of the expected size range was observed, but did not compromise interpretation of the single locus marker phenotype. SSR loci of *P. taeda* identified using the primer pairs in Table 2 are represented in Table 3.

TABLE 3

| SSR loci |
|---|
| RIPPT1 LOBSEQ3-27-97ATC441R (SEQ. ID. NO. 237)<br>ATTAATTTTTTTTGAAAAAAAAAGAGTTTTGAGAAAAAGTCTAATATATACTTGGTGGCATGCCAAAAGATCTCAAA<br>AATTCCTTTCATATATTTGATTAGACAAGAAAATATATTATATTATAATCGTTTAACTTTTTATAATTTTAAAAAATA<br>TATTATAATTATTTTAAGTTTATGATGATGATGATGATGATGGTGGTTAACGTCCACTGAGACCAAATAATGATCAT<br>CGGACCTAAAAAGACAAATTATTTATTTTGATTTAAGATTTTATTCCTATGCTCAAAAAGCTTGCAGAGAAGCCTCC<br>CGAGTTCACTATAATTTTGGCATTGTAAAAGGNTAGGAAAGGTCATTGGTGGTTACAAAGGGTGGTGAAATTGAAAT<br>CTAATGTTGGTGTTTGCCGGGGCTTCC |
| RIPPT6 LOBSEQ5-2-97ATC402R (SEQ. ID. NO. 238)<br>CCGAGACCAAGCAGGCTTGTAACAGGGCTACAGGTGAGTGGCTCCTCAAGACCGGTGGTGTCTTCAGGAACTGAAC<br>TTTCATGATGATCATGATGATGATGATGATGACTGGCTAGCCGTGTTCCAAATAACGAGTCCACACTCGCCCCCCGA<br>TGATCGATTCTCGTCGTCCGATGGACGCGACGGACGATACGAGATCTCTGTCTAGGCGGGATCGAACGATCGATGG<br>ACGAGCTTGCACTACCAAATGTACCTGCGGTTTCATATCTCACGGTGGCTTCGACACTGGTCGNCNAAACTGACTT<br>TGTTCTTCTGTGTTGTTCTGTTNGGTTTTTTTTGGGANGTTGGTCCCGGACAATTTTTCGNCATCTTGTNAAAAATGT<br>GGANCNTNCNCCGAAGGTCCGCGTTGGCTTTAAAGCCCNCTGGGCGGGNCGNTCCAAACNTTGCATCTAAAGGGC<br>CCNTTCCNCCTTNTAGTTAATTCCTNTTNCAATCCCCNGGGCCGGCNGTTTTCANCGTCGTNATGGGAAAACCCGN<br>GTTNCCCACTTNATCNCTTGCANNNATCCCCTTCCCACTGGNGTATACCAAAAGGCCGCCCNTTNCCTCCCNANG<br>TTGGNCNCCTGANTGGAANGGCNNCCTTTTGGGGCTNANCC |
| RIPPT11 LOBSEQ3-8-97ATC229 (SEQ. ID. NO. 239)<br>GCGCAATTTGTTATTCCTCCTATTTCACAGCTTGATCAAAGTGNTCTAGCTGCACTGCCTGATGCTATACGAGATCA<br>AATTTTGAAGAAGCAAGCAGGCAGTGCCAACCTGACCTCTGTCGCCAAGCATGAAGAAGNGAAAGAAGNTTTGTCA<br>ATGCAAAGTCCATCATCATCATCATCATCTGTGACAATCACACCCAAAAAGCAACGAATAATTGATCCATTTGAAC<br>GAATGCGTGCAGCTTCAATTACACCAACGAAAAAAGGAAAATTGAAAAAAGTTACAATTAATTCAGCTCCTTCTAC<br>ACCAAGTGGATCACAAAAACGTTGCAAATGTTAGANAATCATGGGAACCTACATGGTCGCCAGTTGATTCCAAAGT<br>TTTATCCGAACTACCGATAGAAAT |
| RIPPT22 LOBSEQ5-2-97ATC272 (SEQ. ID. NO. 240)<br>ACAACCACATTAGATCTCAGTTTCATAATCTTTGTCGCAATACTGACCTTCCTAGCCTTTTACGATGTCATAATTAT<br>AGTGAGCTCGGGAGGCTTCTCTCCAAGCTTTTTGAGCATAGGAATAAAATCTTAAATCACTAAATAATCTGTTTC<br>TTTAGGTCTGATAGACCAAAGTTTGGTCTCAGTGGATGTTAACCACCACCACCACCACCATCATCATCATCATATCT<br>TTTGAGAAAATGAAGATTTCCTTCTTTTCTAAAAT |
| RIPPT24 LOBSEQAAT10 (SEQ. ID. NO. 241)<br>ACGCACTATTAATGAACACAAACAATGTATATGTAGATTACTTGATTTTTCACAATTCTATAAATTTATCTAAATCA<br>TTATATTATTCGCCATACATTATGCAATAACCATGAGCAGTATCATCATAATAGAATATAAGCACATCATCAACACA<br>TCAACACAAAATTCATATTGACACCGGATACTGAGGTGGAAACCTAATTTGGGAGAAAACCATTGTTGTTGTTGTCT<br>CTTATTATTATTATTATTATTATTATTATTATTATTATAAAGAAAAATTCTTCTTACATCTTGCACAATCACAGACTC<br>TTACGAAGTTGCGGGCTCCTACCTACGGGAAGNTACAACCTCTAGAAATTATCCAGCTCCACTGGAANGAAGCTAC<br>TACTCCCTAATCAAGTTTACCAGCTCCNACTGAAAGGAAC |
| RIPPT31 LOBSEQAAT18 (SEQ. ID. NO. 242)<br>ATTGTTCTTCTGGATTAATTACACTAGTAATTTTTCAAATCAAAGTTTCAAACCAACCAATGTGGTTCATCATCAAA<br>ATATAGATGAGGGAGGTTGAACTAAGCCATCGAGATTGATAAGAGGACTGGCAATCTGAACATAGATAATGGGTGG<br>AAAATTAGGAGTAGTTGGATTCCTACCCTGACTTCTTAGGTGGCTTTGTCCCCCATCTAAAATTTAATTTAATTATT<br>ATTATTATTATTATTATTATTATTATTATTATTATTATTATTATTATTACTATTTTGGTCTTATTCCCTTCTATTT<br>TCCTAGCTTAATTTATGATTATTACATATAATTATTTACTTCTAGTTTAACCCTCTTCCTTTTTTNATTTCTNTCTTT<br>ATTTCTTTCCTATTTTTTTATNTTCCATATCTCTAGTTAATAATTTATTATTAATTANTTCAAGGATGTTTTAATTAT<br>ANTTCTNNAAGTTTAACATNTCCTAATTTATATTTTATTTCCCAACTCNCAATCCNTTACTAA |
| RIPPT32 LOBSEQAAT49 (SEQ. ID. NO. 243)<br>ACTTGTAGTCAGTTCAAGAGTTAACGCAAGGGAAACCTAGCAGGTTACAACCTGGGGTCAATCGGATTGGTAGCTA<br>CCTGTTCGAGATATTCTGATTTCACATTAAAAAGTGAAAAGTGAGTGTTTTAAGTCTATTATTATTATTATTATTATT<br>TATGACCTTCTCAATTATGCCTAAAACATCTTGTCTATTTCCAGAATCTGAAATTTCCCATCAATTGGGCTATACTA<br>CAGACTCCTCTGCATACACCTTCCTCACTTTGAACATCGAGAGTTCAACTACAGAAAATTTGCACCTTCCACTTTGA<br>GAGTTCAACTACAGAAAATTTGCAGGCTGGCGGTGGAAAACAGTCAAGGTATGCATACGANTCCATGGTGCTGTTT<br>TTNCCGGAAGAAATTA |
| RIPPT33 LOBSEQAAT46 (SEQ. ID. NO. 244)<br>ATTACAATTTTCTTCTTACTTAATTGGAGAACATGCTTGCAAGTTGCAATTTGTAAATGAGATTTTTACTCGAGAAA<br>TAAAAAGGACTAGGTGAAGAACATGCTCCAACCATTAGGGAATATAAGGTGGTTGGGTATAATCCTAGTGAATATAT<br>TATTATTATTATTATTATTATTTTTAACTGATTTTGTGGAAAATGCTCCATTTTTTATACATGTTACTTTTCTCTTAA<br>ATCCACTTATATAAGTGACTATAAATTGAAGAAACTGTGACTTTACCTAGAT |

TABLE 3-continued

SSR loci

RIPPT64 LOBSEQ5-6-97AAAC2C4 (SEQ. ID. NO. 245)
ACGGGAAGGTGGTGAGGAGCAGCAGCGTAATCAGATGGTCATAGGCGTTGTGTCAAACTGCAGGCTCCGGACAAAAC
CCTAACCCCATCCTGTACGTTGTTTCCTCATCTTTGCTTTTTCCAAATCCAAGCATATATATAACCCAATGAGATGA
ATAGTTAAAAAACAAAAAAAACAAACAAACAAACAAACAAAAACATCCTAAAAAATAGCCAAAAATGTAAAATCTC
GAAATAATCCTTTTGAGGAGAGCTTTTCAATATCTTCAACTCGCCTTCCGGTGTAGTGGTTTAGG

RIPPT65 LOBSEQ5-6-97AAAC2F7 (SEQ. ID. NO. 246)
ACACGAACGGTCTACTTACACTTGACTGTATTGGATAATATACCTTCTATATATTCAATACTGTCCACCTATAACCA
ACAGCACTTACCCAAAAAAACCTCAAAAACATTTATATAAACAAACAAACAAACAAAAAAACCCTAAAAACACCTA
TAAACATAAACTAAGTCCAGGAAAAGATTTTAATTTTCTGATTTACTGGGCTTTCATGAGGCTGAGATTCTTCTAAA
ATTTAGAACGAAATGCATGATGTATACTTCCATAATGGGAAAGCACTTGGTTTTTTTGGTTGCTTATTTTTGTGCATA
CCGAATCGTCATATTTTAATCTTTGCTACTATGGC

RIPPT66 LOBSEQ6-5-97AAATE2 (SEQ. ID. NO. 247)
ATTATTTTTATGTAGGCTTTGATTATATTGGTTCCCCTTAGACTCCTATATATAGAAAGGAGGTCTTGTCATTTGTAT
CATCAAAAAATTATTCACTTATGTAATGTAAAGGAGGTTGCCTTCGAAGTGGCTTATTTTGAATTCGTTGATCCATC
TCTTCAATTTGCGAGTTGGTTTCATAACATGACTACCTTGGCACATTATTCCATGGCGTCTATCATGGATATTATTA
TATTATTTTTGTTGATAGAGTTTCATGTGGTGCAACATAGTCCTCCTCATTATCTCATTTGAAGAGATAAAAATAA
ATAAATAAATAAATAAATAAATAAATTGACTACAAAATTCTTCATCCATGTTAT

RIPPT67 LOBSEQ6-6-97AAATC7 (SEQ. ID. NO. 248)
ACAAGACTTCAAAGTTGTCTAACAGCCCTCCAAGACCAAGATTAATGCCTCAAAACAAGCCTATTAAAGTTTGCAA
ACAAAACGATAAGGATATGTTCACATCGGCTCCAAATAAATAAATAAATAAACAAAATGTATTAATATATGTCATGT
TGGTTTGATGCATAGACACATCGGTTCATAAGGTAATGTCGACTCAATTGTATGTGCACAGCCGTTATAAATACCCT
GTTGGGGTATTTGCAAATGGGCAAGAAAGAATTCACATGAAATCTTCGCATAAGGGAGCCATAATGAANGGAGCCA
CAATCAAGGTTGATGGANCCGTAATCCAGGTCAAAAACCACAGTTAGGGTATTGACTGCCCCGTGTTTTTGGGTTTT
ANGTGCAATCCATGG

RIPPT69 LOBSEQ6-5-97AAATE9 (SEQ. ID. NO. 249)
ATCAAGAATGGGGGATGATTCACCATTTTTGGAGTAAAAGGATAAAAATAAATAAATAAATAAAAATAAAACCTTAT
TTTCAACTCGTATTTTCAACTTATCTCTTTACGATTTTACTCAAATTTCAAGCAGAAGCAGTTGTTGGATGCAAAAT
TTAATTTTACATCCAAAAAATACCCATGTTGCATACTTTCAATGGACCCTACTACACAGAAAATGTGAAATACAAGA
AATAATGTGATTGTAATCATGTTTTTTCATGTATTTCATATTTTTCATGTAGTGGGGTCCATTGAAAGTATGCAACAT
GGGT

RIPPT71 AAAT1-A1 (SEQ. ID. NO. 250)
CCATCTTATATTATCCTCCAAAAAAATTTCCTCTCTATACTTTAGGAAAAAAATTATGTATCTACTCAAAGTGCTTG
GGCACATTTGCTAATATAAATATATGGTTAGTGTTATAAAAACAATTTATTTATTTATTTTATTTTTATTTATTTATT
TATTTATTTATTTTCGTGGGAATGAGCATGGCATTCAAGCCATCACGTGGATGCTTGCAAGAAGGAGAGTTGAATTT
TTAAGACGTGAAAAATGAGGTGGCTGAGCAGAAGATGTAATTGGGTGATTTGTTGGCAGATAGAAAGGGAAGGGGA
ACCCTCCATCTCTGCTAAATCTGCTAGAGAAGAGTAAAAGCAATGCAACAAAGGGACATAAACGAACAACTGGAAG
CAACTCAGATGTGGACCATGGTTTGGAGGAGGATAAGAACCAATTGGAGT

RIPPT77 AAT3-B5 (SEQ. ID. NO. 251)
ACGCACTATTAATGAACACCAACAATGTATATGTAGATTACTTGATTTTTCACAATTCTATAAATTTATCTAAATCA
TTATATTATTCGCCATACATTATGCAATAACCATGAGCAGTATCATCATAATAGAATATAAGCACATCATCAACACA
TCAACACAAAATTCATATTGACACCGGATACTGAGGTGGAAACCTTAATTTGGGAGAAAACCATTGTTGTTGTTGTCT
CTTATTATTATTATTATTATTATTATTATTATTATTATTATAAAGAAAAATTCTTCTTACATCTTGCACAATCACAGACTC
TTACGAGGTTGCGGGCTCCTACCTACGGGAGGCTACAACCTCTAAAAATTATCCAGCTCCAACTGGAAAGGAACTA
CTACTCCCTAATCAANTTTACCAGCTCCTACTGAAAGGAACTCTTACTCCCTCCCTAAAGGNTCCATCCCCATACC
TTTTNGGAAAAANTTCCTAATCTTAAAMCCNCTGGNGGCGGTACTATGGATCGAACCGNNCAACTGANCNNACTG
NATTTCCNATGTCCCAATACTGGGTANCNGGCNACTGTCCCTTTTAATGTT

RIPPT79 AAT5 (SEQ. ID. NO. 252)
ACTTTATATAGCATTTAAAAACACAATTTAAATGATGAAAAGTCACACATTGTATATTTAAAAAGACATAAGCACCC
TAGATTCATTAGGATCTATCAAGCCGTATGAGGGACACAATTTTTTTTTTCTAATTTTGCACTCTAAAACAGGTTTG
CACCCAATGTGATTTGATCCCTCTAGGCGCATGCTAGATCTGTGATTAAAATAGACCTATAATGGTATATTTTCCAT
TATTATTATTATTATTATTATTATTATTATTATTATATATCTGGTTAATTTTCACTATTCTCATATTGAATTTCTTTTC
AAGATTTCCAAAATATAAAATTAAAATGT

RIPPT80 AAT55 (SEQ. ID. NO. 253)
ACATCACACAACCAAAATTAAAACATTCATAAAAATTAATTAAATTAAATTATAATTTTATTATTATTATTATTATT
ATTACATAAACTAATGAATTAAATATATATACATTCAATAACACAATAATGACTAATTAAATTTTATTTTAAAATAA
ACCAACCTATCCACATTCTAATAATAATAATAATAATATCCATTTTTAAGGTCACAGCCAAGCCAGACACCAAATTG
GTGTATGAGACCCCCTTGTTTGTGGGACAAGGGACCCACCTCCGCGCAGCGATTTGACTGCTAAGTCTACGAAGGC
ATACATACTCTTTACCCCCTCTGGGTTTTGAACCCTGTGACTCCTTAGGAAGGAAACACTTGATCTTACCCTTTAGGG

RIPPT89 LOBSEQ8-19-97TTC3B9 (SEQ. ID. NO. 254)
CCTGGAACCCTAATGGTCAAGTGCCCCAGTTGAGAAGTGACATAAGTATAATGATGCATATGTTGTGTATATAGCAC
TATCACCTCCAAATTTATACGAAACCCCGAGTTGATAAAGTAAAGTTGGTAGCCCTAGGAGTTGCAACATCTTTGTT
GCAATACTGAGGTTCATCACTTTTCTTCTTCTTCTTCTTCTTCTTCTTCTTCCTTTTCTTCTGCCTCTATTTTGTTTGT
CTCTACTTCCTATTTTTCTTCTACTTCTTCTTCATCTTCTTCCTCTTCAACACTAGANGTANGGGTCCCACCATGTT
CAAGGGCTTAGG

TABLE 3-continued

| SSR loci |
| --- |

RIPPT101 pPT101.seq (SEQ. ID. NO. 255)
ATCTGGTAATTCTGTTATGATCATGATTATGCTGATGTTTATATATGTATACATGTAGGTGTGTATGTATGTCATGTT
TGATGGGGTCGTCATGGATCATGATTATTAACACTAACATTTGGTGTGTGTGTGTGTGTGTGTGTATGTATGTCGT
TGTCTGATGGGATGATGATTGTTTTATGCTAATGATTATATATGTATGTATCTATTTATCTATGTCATTGTTTGACAG
GATTGTCAGGGATTGTTCTTGTGGCGGTATTATTGCTTATGCAGGTGAATTGAATGAAGAAGTTCCTGGTTTATGAA
GACTCGTGTAGGAAGAGTAATCATGACAAATATATGAGGTCAATATCATGTGGTTATGAGTTGATATTATGTGATTA
TATTATGTATATGTTATGGATATGGTATATCGAGGGATACATCAACGAAATGAAAGAAGTGTGATCTACGACATGCT
TGGGAAAAAGCATGGATAAGACACNANAAGCAAGGTTTATTGGTAAGGATGGGGTGGTTTTAGATGTATGGTAATA
CTATTTTGCATATGTTGT RIPPT103 pPT103.seq (SEQ. ID. NO. 256)
CCAATCACCATATAGCCACCTGTCAGCTTCCATCGTTACCACNAAAATAGTCCCCATCTAAGCAGTTTTCCTCAGC
TTTGGAATTTGTGTCCCCAAATCAACTCATTTAATTTGATTAAGGTTATAATATTTATAATAATGGAAAATGCAACT
GGGATATTACAAACCTCTCCCCCTTGGTGGAACAACATACTTAGTGATCGATGACACCTATACAACACAAACAAAA
AAGATATGCTTAAAAGTCCAAACACAATTGAGATGGAGCTTTATATATAGATGTGTGTGTGTGTGTGTGTGTGTG
TGTGTGTGTGTGTGTGTGTGTGTGTATAGAGAGAGAGAGATACATCTCACTTTATAAATTCCGCCATTTTCCAAT
GGCCCCTTTTTGTAGTCTTCTAN RIPPT104 pPT104.seq (SEQ. ID. NO. 257)
GCTAGTAAGAATAACTAATTATGTGATCAAAATTGTGTCATGTAAATGTTCTAGTTTCTACCAAAATTTGAATCTTT
ATGTCTGCATTTCATTTTTGCGTGTATAATTTGTGATATGTGTGTGTGTGTGTGTGTGTGTGTGTGTGCGTGTGCG
TGTGTGTGTGTGTGTGTGTGTGTGTGTGTGTGTGTGTGTGTGTGTGTGTGTGTGTGTGTGTGTCTACATGTGTAAA
CTCTCCATGTCCTATGTCANTGTGTCTTTAGACTNTGGATGTGGGT RIPPT106 pPT106.seq (SEQ. ID. NO. 258)
CCTCTTCAATCCTTAAGAAAATGAGGATTTTCCCTTGAAAAAGGAGTCTTAAGCCTTAAGGCCAAATCGCAATCGGA
GGTTGCATGAGGGCAGACTTAAGGTTTGGGCCGTGGAACCCCCGATCACTAATCTCTGATCAAATCAGATTGGTGG
ATCGGAGGCAATCACCTTCAGTGGTCATATATATATATATCTATATATATATATATATGTGTGTGTGTGTGTGTGT
GCGTGTGTGTGTGTGTGTGTATAAATGGATATTAGCGAGTGGATAGTGTGATCAGTGATTAGCCGAATCGGCGAAAC
CCTTATCAGTCACCCGGGGCAACATATGTGGGCGATGCTGACGCGATCAGCTGACGCCGAT RIPPT117 pPT117.seq (SEQ. ID. NO. 259)
CTCATATCTTCTGACTAATGCAATATACAAATAGTAGGGGTTTTTAGCTGTGTAATGTGTTGATTGAATTCTTTCTCT
TGTATGCTTCATGATTTCTCGATCGATTAATTTTTTCCACTAATGAGTAGAGTAGATTCAAGTATTTTGTTTTAGTAA
ATTACAATTAGTAGTTTGAATCTACAAGGAATACACACACACACACACACACACACATTAACATAACCATGATCAC
AACACAATTACCATTGCTCATAAGTTCAAGGCTAAGAGAAATTCCTTTATCCACGCAGAGTATACATAATATTGAGA
ACGACAGTTCTCAACATAGCCAAGGCATTTGTTACCTCAAGCCCATGT RIPPT123 pPT123.seq (SEQ. ID. NO. 260)
ATCGGCGGTTCGCAATCGGTATTGGCATCAGCCATGCCATATGGGAAACCCCCGGCCCATGCGATACACGATTGCA
ATGTCGCAATATCGTGTCGAAACATTGGAAAGGAGCGGGGCCATTATATATATGTGTGTGTGTGTGTGTGTGTGTGT
GTGTGTGTGTGTGTGTGTGTGTGTGTGTGATGCGATGGCTAGACCCGACGGGGCTATAGGTGATAGTTGATATATTTTT
AAATATGCCCAACAACATTTTGCTATGTATTTCGCATATTTCGTTTGATAAATGAAATATGAAGGGAAGCACTGATG
CAATGAAAACAGGGCCCGAAAGGGTNTGTGAATGAAATCATATATCGCTTCAAGTCTGATATGGGTTGTTTTGCAAG
ATTTTCCAATGTTTTAATGCATTTCTCTGTGTAAACAGAGAATGGTTGTTCCAGGGATTTCAAAGGA RIPPT126 pPT126.seq (SEQ. ID. NO. 261)
CCTCAANGCTAAGANGGCTTTACTGTAAATCATACCGAGAGAGGTCTTTGTAAAAATCATGTGTGTGTGTGTGTGTG
TGTGTGTATATGTGTGTGTGTATGTATGTATATTAATATGGGTTACTCTGTTCGAGTAACTGTACTATTGTGTGGATT
GAACTTATGTTTATGTTAGAATAGATGTGGCAGGCACAAATTAAGCTCAAGAGGGATCAATGCTCATATGGAAGTAT
ATAACATCATCTTCATAGATATCAGAGCACACAACAGAGGGAGAAAGGTTACATAACCAAGATTGCAGTGTCAAGA
TCTTAAGACTGACTGTAAGGTCGAGGCATAACAGAGGAGGAATTTGTAGAATGGGTGGGAGAAATCTAGATTAAGC
CGAATCAGAGTGGTGCAACACAAGT RIPPT128 pPT128.seq (SEQ. ID. NO. 262)
CCAAGGCCTATGTTTTGTGATCGACCCTAGTCTCTTGTGCATGGTATCCTACACTTTTCATGTGTGTGTGTGTGTGT
GTGTGTGTGTGTGTGTGTGTGTGTTTTACATGTTCCTTGAGGGGTAAGAAATATTTTTTGGTCGTCGTTTATCATTTC
CATAGAGCATCGAGTTTCTACTCTGGCTTAGGGTCCAAAATTCTAGATAAAGTTATCGTACTAGTTGTTCTTTCAA
AAATTTTATTTTCACTCTGTAAATAGTCATATGGGTTTATAGGTTGCAATCTCTTGTTCATGAATTCCAATTATTACA
AATTGGTAATGAAATATTTTTGTTCTGGTCAAGGGTCCAAATCTTGGGGTATTGTCTANACGGTATTTTTGTTGGTC
AGGTTAGAGTGGTTTATAAGTTCTCTACCCCCTCTATAGAGAATGACAAGTTGATGAGGGGGTGCAAGAATATCTAC
TTCTCAATGT RIPPT132 pPT132.seq (SEQ. ID. NO. 263)
ACAAGCCTAGTTCCTACAGTTGGTCTCACTAGTGGTGTGATTCCTACTCCTCCCCTCATCCTGCTTCCACTCTGTAC
ACCATTAACACATTTTTTATTCTCTAAATCTCCCAAACAAGACACAATGTTGAAACCGTGGTGCTCTGATACCGCTT
GTAACATGCAAAGTCACCAACCAAACACACACACACACACACACACGCACACACACACATACATAATTGTCTCTAG
CTCTTGACTTGCACTATCACTTATTTATATTTTTTTTAGAGCATTTGAATTAATTGACACACAACTAAATTAATTGAC
CTAGTCATAGCTAGTCATGGATACACTTTATGTTCCTTATAAGTTGGTAAATATAACTTATAAGTGTGAATCCATTA
GCGACGAACCCACCTAATATTAATAGCACTAAGGGAACCACGCTATAATTGTTTGGATTAATATTTGGTTGTCATAT
TATAATATTGGGANGTGACCTACCTTAAAATGTTTCTCGAAGGGCTCTTTGGTCTCTAGCAATCATACAAAGANG TABLE 3-continued SSR loci RIPPT134 pPT134.seq (SEQ. ID. NO. 264)
ATCTGCACTTAGTGCTTGGCTATCTGGTCCTTACCAGACTTGGCCATTTTTCTTTTTTTTTTCCTTTTCTGTTTGTCT
TCTATAGCACAACCTAACTTCCCCCTTTTCTTCCCTTTTTCCTAGAAACCTTTCCAGTCAGGAGAGATAGTTAGGGT
TGTAATTACTGCAACTGCTTTTCCCAACTTCCCATTAAGAANTTGCCAGCATTTTTCCAAAAACATTTCTTATCTTA
TTAAAGAAATAATAAAAATATTATTAAACTCCAAAACAATTAATAATATCATATTCAATTTTTAACCACAGTAAATT
CAAATGTTTACATTTTCCTGGGGCATTACACACACACACACACACACACACACACACATATATAATTACAGTATGA
AACTGTTTTTTCTCTGAAAATCATAGAAATCATGGCAATATTTTGATAAATTATGGCAGGGATTTTTGTAAATCTAN
GTTATAGTTGTTAAAATTCAAGANTTTGGGTT RIPPT135 pPT135.seq (SEQ. ID. NO. 265)
ATCTTTTCAATATTTAACATTGAAAAGCATTAAAGAATAGCATTTTGACAACTAAGGGTGAATACCCAAATTCATAC
ACTCACGCATGAGCTGAGTCATAAGATCTAAATCTAGACTATATTGCTAAAACACTAGTCATCACTTTTGATTATG
ATTGTAGAAATTAAACTTTTAATATTGTTACTTTCATTGTGTGTGTGTGTGTGTGTGTGTGTGTGTGTGTGTGTGT
GTGTGTGTGTGTGTGTGTGTGTGTGTGTGTGTGTGTGTGTGTGTATGCTTAGCATAGTGGGAAACACAAATAGACTTTA
GTTTNNGACTTGTTGTATGAATTATCTCTCCATAATATAAATGCAGACAACT RIPPT139 pPT139.seq (SEQ. ID. NO. 266)
ATCATTTCACCATTACTGTGAACCAATTGGAAACTTTGCAAAAGGATGTAGGGAGCATCCACACGTCTACGGAGGT
CATTATGACGAGGCTACAAAATTTGGACCGAAAGGTCGAGAACCTCAATGAGAGGGTGGAGATTGTTGTGGTGCCT
ATCCTCAAAGAAGTTTTCGCACTTGAGGAGGGTGCACCAGTGATCACTTTGAAATGGGACTTCCCTCTCTAGAGCC
ACAATGCAAATGGAGATGCAGCAAGATGCGGAGCAACAGGAACCTAAGGTCGCAGGTCAATTGCGAGTTGTAGAAT
AGGAAGAAGTGGAAGATGAAGTGCAACAACCAACCGAGGGAGCTAAATTGATGCAATTCAAGAGTGGTTTTTTGTT
TGTGTGTGTGTGTGTGTGTGTGTGTGTGTGTGTGTGTGTGTGTTTTGAAAGTATGTTGAAGTGAATGTCGTTTTTTTGGA
GAACGC RIPPT158 pPT158.seq (SEQ. ID. NO. 267)
ACTAGAGGCACACAGTGGGAGTCTCAGATCGGATCCACCGACTACTTAGTAATGTTGCACGAGTTGTCTCGTGCTA
CCATGACCACCATGCTGAGTAGTTCCTAGGAATAGCACTTACATATTTTTCGAGGCCTGTGTGCCACGGATGTATGA
GGCTTACGAGCCACTAATGTTATTTTAGACACACATATTATTTTTGGGGTTCTGATATATCAAACATTCTCATCAT
ATATATATATATGTGTGTGTGTGTGTGTGTGTGTGTGTGTGTTGGCTTGTTGGGGCCTAACCTAGGTTTAGAAGAGGTTT
AGCCAAACAAATCCCACACTACTGGCCCTTTCAGCAACAATCCACAGAGCGTGGACTGAAGTCTCACCCGAGGTAN
TATGGGAGGGTGCTGGAACCAAGTTTCTCCACCCTTGGTATGTCTTGATGTGGTCTGGANGATCGCAAACCATTCTG
CACTCCTACACTTCTCTGCACAGAT RIPPT159 pPT159.seq (SEQ. ID. NO. 268)
ATCAACATTGGCCGTGCCATATGGCTTACCTCGGGTCCACGCGATATTGCGATGCGGCGATCAACATAATGGAGCA
GGTATATATGTGTGTGTGTGTGTGTGTGTGTGTGTGTGTGATGTGATACATATATCTGGACCCAATGGGTTTATGAATG
CAAATATATGATACTTCAAGTTCACCATAAGGTCCTCTGATGGGATTTTTCAATGTTTAATGTATTTTTAAAATAGA
AAGGGAACCCATGTAACAGGGCATTTGTGACAAGCGATAGCAATTTAAAAGGCAAACATAATGGAAAAAAATGTAG
AGTTCATAATTTTTGAAATCTGATAGACGCGTTTGGGCAAATTGTTACAGGCTTTCTGTGTATTTTCCAGTGTAAGC
CGAGAATTACCATCTTTGGGATTTCAAGGGCACTGATGGTCCATTCCATTACGGAATAAGTGG RIPPT165 pPT165.seq (SEQ. ID. NO. 269)
CCTTGTGGAAGCCACAATTTGTTGAGTATTGGCAATTATTGAAAAAACCCCTTTCAAGCTCTTGAATCTGTATTCGTC
CTCTTTTGAACGAGTCTCTCTCTCTCTCTCTCTCTCTCTCTCTCTCTCTCTCTCTCTCTCTCTCTCTCCACACACACA
CACACACACACACATATTCATGGGTATGTTCAACTTTGATGTGTTTGTTTTGTTGCATGGTTTTATTGCAATGACTTT
GCTTCCCTTTGCCAAGGTAAAGTTTAAATTGCTTATCCGTGTTTATCATATTTTCTCATGCTAGATTTCTTTACGAGA
ATCGGGGGTTAACTAAGGAATTCCTTTTGTCTCATCGCAGGTTAGTTTTGGCAATATGGGCACGTTGAATCCGACAA
GTTTTTTGGAACCAACTACTCATAATTCCTCTTCTTTCGCGCAACTATACATGTGCTTATCTATGTTTTTTGTTTTCT
TCAAGTCATAGAAGCCACTCANGGTTCCAACTCATACACTATATACGT RIPPT166 pPT166.seq (SEQ. ID. NO. 270)
TTGAGATGAGTAGTGTGGGTGGTGGTCTGTTGTAGGGAGCAGAACCCACCACAGTAGACAACTAGGTTTCTTTTTCC
GCTATTTTTGAGAGACATGTGTCTCAGATGTATCACGAACACATACTCTATTTTTTGACATACACACTATTTTTGAG
AATGTCCGTGCGCCACACGATATATATATATATACACACACACACACACACACACTATCTATGGTTTATTACTGTCTAA
ATGCTTGCATACAATGTTTTGATTATAAATTGCATAAATGTCTATCTAATACATGATTTTGCAATGCATCAGTTAAC
GTGTTTAATCTTCTTGGAATGTGTTTATATGTGATGAAATCAAAATTTCTTTCCAATAATCTAACACGCAAATACAA
CCTTAAAATATGAGGGTTTCTGATGGAATAATGCCCGTTAAGCTGCAGAGCGACAAGTTAAGAATCCAGGTTCACA
ACCAATGCATGAATATCGAGGTTAACAACCTCAGTCAATAGTTCAATGACAGTGCTATCAGCGACGTTGTTTGCGGT RIPPT171 pPT171.seq (SEQ. ID. NO. 271)
ATCTCTCCACAGCTTTAGAGACACATTGTGGGGGTATAGTCCTCTCATTATGAAGGACTCCTATGACATCTTTTTCA
TGTTCTTTTGTGTTATCACCAACATAGAGGAGATTAACTCCTTAGGATATTTTTTATGGGATATGTCTTTGCATATGT
ATTGGATTATGATCCTAAGCCTTAGAAACCCTTATTTTGACTAATGTATGCAAACTATATTTTTGTTGTAAAACTCTT
TTTTGATATATGTGTGTGTGTGTGTGTGTGTGTGTGTGTGTGCATGTGTTTTAGCTTCAATATTGTTCACTTGTGAATGT
TGTCTTATGATGTTTTCATTTAGGTTTCTAATGAATGTATCATATGCATGGGTGACAAAATTAATGTGACAAATGTC
AATATATGACACAATTAGCCAATGAATAAGCTAATGTTTTAGAGTCTAGTAATATAAATGTATGAAATGGTATAAAA
TCCCATTCTAGCAGATGT TABLE 3-continued SSR loci RIPPT179 pP179.seq (SEQ. ID. NO. 272)
ATCATTTATTTCAAAACATGTAAAAAAAATAAACATGTAGGAGCACAAGCCATTGATTATTTTCTCTATTTTTTAAA
GGAAGACATTTAACTTAAACATTTGTAGTCAAAATCAACTGACTTTCAATAGTATTTTTTAATTATTATTATTATTAT
TATTATTTATTATTATTACACTTTTTTCTATCAAACGGTCCAACTGTGTTAAGTGTCTAATACATATGCCTAATTTTT
ATATGCTAACATTGCAATACTACTTACTAATTTTGGTTGTGCTATCCATAGAAGCATTTGGTAAGTGTTCATCATGC
AATATTTTTACCATACACGTTATGATTGCATGTCCATTTTCAAGCAAGTTTTCAAAAGAGATGGTTATAGATATAAT
TCTCATATGAGTTGTAGGATAGTGTTCCAGCAGTTTGCACCCATGANGGAACTATCATTTACAATGAAACTACAAAA
CATGTTGGCATTATTGACTTGTTTAACACTACATTATTAATTGTTATATGAAAAATT RIPPT185 pPT185.seq (SEQ. ID. NO. 273)
ATCTTTCGATGTCTATTGGTATACTATTTCAACAGAGGGTGTTTGCAAATCATGGGGTAAAATAATAATAATAATAA
TAAAATAAGAATAAACTAACTTCAAGACAAAGTTCCTTAAAGAGGGAGAGTATGTAATGCCCCATAACAACAACAA
CAACAATAATAATAAATGACAATAAAGTAAATAAAATATTTTTAATATATAAATAGAATAATAATTAACAAAGAAAA
GATAAAATAACAATTAACAAGAAAAATACATGAATATAAAAATAAAATAACAAATAACGAAGAAAATATAATAATA
AATAAATAAACTAAAAATTGGCATGGACACTGGTGGGCTCCAGTATTGTAGCAATAATGCTATAACTCCTGGGACTC
CCTTCTTTACTTTTATCAACCTGGTAGTTCGTAACAAACTTGGAAGTGACAGTGTTGTATGCACAAGT RIPPT193 pPT193.seq (SEQ. ID. NO. 274)
ATAATGGCCTTGGTGGGCTTAATGGTTAAGAACATGTATTTCCTTGTAAGAGGTCATAGATTCAAATCTAGAGGGAA
GTAGAGAANGTAAACCTCCACAGACTTTAGTAGTCAAATCACTGTAAGGAGGCGGATCCCTTGTCCCAGAAACAAG
GGGTCTCATAAACCAATTTTGTGTCTGGCTTGGCCATGACCTAAAATTAGATTATTATTATTATTATTATTATTATTA
TTATTCAAAGGGAGAATCTAGCTCTGTTTGTAAAAAGTATCTAACCCAGGCATAACATCAACATAAAACCAACTTGT
AGTAGAAGTATGTTGAAGATTTGTTTTAATATA RIPPT211 pPT211.seq (SEQ. ID. NO. 275)
ACATTATGCAATAATAATATTACACAACCAAAGTAATAATATAACTTGAGTGGGCATAATGGTTAAGAGCATGTGTT
TCTTCCTAAGAGGTCACATATTCAAAACCAGAGGGGGGTAGAGTATGTATGCCTTCGTAGACTTAGTAGTCAAATCG
TTGCGCAGAGGTGGGTCCTGTGTCCCACAAACAAGGGGGAGGGGGTCTCATACACCAATTTGGTGTCTGACTTGGT
CGTGACATTAAAATTGGATAATAATAATAATAATAATAATAATAATAATAATAATATTGTCAACCCACCTAATTAAT
TATACTTCATTAGTTGATTCTCCAAGAAATACATCCTCTATGCACATTTTTCTAGTTTCATGAGTAAAAAAAGGG RIPPT255 pPT255.seq (SEQ. ID. NO. 276)
CTCCTGAGTGGTCCCATACTTAAAAATAAAATAAAATAAAATAAAATAAATAAATAATAAATAAATAATAATAATAA
TAATAATAATAAAATAAAAGGGCTCCAACAGGCCTCATATCCATCTTTGTTATCAATCAGTGCACCACTTTAGTCTC
CATGTATGCCCAACATTCTATATGTTAGAATCTTTTTANATTCGTGACAATGTTCACTANATCCCCATATTTCAAAT
ATTTCTTGTGCTAACAACCTCTTGATGATCTTTATTGCCATGGAATGAANAGTGCATCTCTTTTTCAAATTGAATTC
ATAAAC RIPPT263 pPT263.seq (SEQ. ID. NO. 277)
TATGTGTATTCAATGTTATGGACTAGGAAGGCTTCAACATCACTAGAATACCCAATTTTCTGAAGAAGAAAACGTAN
TCTANCAATGAATATTGTCAACTAAATTTGGATTGGACCTGAATCAATAGATTGTTCTTTATTCAAGCGAAAAAATA
AATAAATAAATAAATAAATAAAAATAAAAATAAAAATTGATGTGCTAGTTGTAGACAAGGACATTAAGATGAAATG
GAAAGAGGTCAATATGCATTTGCAGGAACTTTTGGGGAAAACCTCGAANACTGCCAAGTCTATCTGAACATTCACA
ATTCCAGCTTATATCGGATTGCATGCAAGCATCCCGTGTTCCCATGTGCAGACATGATACATTGGATCATCTCNCAC
NCTGATCTTGAGATGATGACNTTGAGAAGTGTCCTTGGGATAGAGATTGTTACCTTCAAGGCATAGGATTATCCNTA
GATGTTATCCATATGTCAAGACCCAGTAGTCACCCATGGAAGACACCCTTCANCATACCCCAACCAACAATGCCAA
CTCCAGGGGAT RIPPT274 pPT274.seq (SEQ. ID. NO. 278)
TAGTGTTCCTCTCAAGTGACCCCCTTTTCCTAAACAAATTTGAAGTATATCCCACATTTACCCTTGCATCCTGCACA
AGTATATCAACTTCCCTAATTTTATTTATTTATTTATTTTTATTTATTTATTTATTTTTTTCTGTCTTCTCTGGGTGGT
TCTGTGTGAGTGGATGTCTCCACTCTCTTCTCCTCAATTTGTGGCTTCTCCACAACTTCCCGAGGCTCATCCTCTAG
GGCTAAAATATCCTCTTCTGGTGGAATCTGAAGCTCCATCTTAAGAGAGCACTAAATTTCTTTCTCCTTATCAAACT
TTACATCCCTTTGCACAACTTCCATTATGAGGGAAGGTAAGT RIPPT287 pPT287.seq (SEQ. ID. NO. 279)
ATTCCATGTGAGGACTTTCAGTGAGAATATTTTAAAACTATATCATCTCCCACTTCTTGCAATGAAACCTTTCTAGT
TTTCCTTCCTTTTTTTTTGCTTTTTTTAACCAATTCTTTGACTAAAACATCGTTACCTTTCTCTATGAATTCCTCTAT
GGAATGTATTCCCGGTTCCTTCAAANATTTTATTTTATTTATTTATTTATTTATTTTTTCCTTTCAAACAAATCCTTT
GGATAATGCTCACATTTCTCTTCAGACAAATTCGGCAAATATCTCTCTACCCATTCATTGAGGAGGTCCACTAAAAC
ACTTTCTTCCTTGGAAAAATAATCATAATTATGTCTTATTAATCGAGCAACCTCCTCAATATCCGGGAGGTAAGTAA
CAATAATTTTCTCATTACCCCCTCTTCATATTGTGAAGTCTTCCTCTTCACCGGTTGCTTCATTTCCTTCACATTCTG
GGTTTGTTCCATCATCTATACATCATTTGGTTTCCTCTTTAGGGT RIPPT293 pPT293.seq (SEQ. ID. NO. 280)
ACCTACGGTTGTGAAAAANCGCTACTATTGGCCGAATCTAATAAATAAATAAATAAATAAATAAAGGAAGGTTGTT
GGTTTCATCACTAGGTGTTTGGATTGTCGATAGGTAAAAGTGGAGTTCAAGCATCCAAATGGTCTATTGCAACCAAT
TTCGATTCTAGAGTGGAAATGGGAGGCCATTTCCAGGGATTTCCTCACAGGTTTGCCAAGAACATCTANATAGCATG
ATTCCATCATGGTTGTGGTTGACAGGTTGACTAAGGTAGCTCACTTCATAATAGTTAATTCTACTTATATAGCTAGT
TAGGTAGCTCGAGTCGTCGTCAAGGATATAGTTAGGTTACATGGTATTCCTAAGAAGATATTTGACAAAGATACCAA
GTTCACTTCCAGGTTTTGGAAGGAATTATTTGCAGGTTTGGGTACAGAATTGCCCTTTAGT TABLE 3-continued

| SSR loci |
| --- |

RIPPT298 pPT298.seq (SEQ. ID. NO. 281)
GGATATCNAGANTCGAGGATCATGCATACTAGCTTGTCCAACGGGGNAGTTGGCGCTAGGGAACCGCAAGACTTGC
CAAAACAGCGGAGGCTTTANCCATGAGTGGACCCNGGTGAAGGGGATGATTGCCTTCACAAAATCTATAGGGGAATC
GAATATCCCCTTTTCCCTTTCCATGACCAACTACGGAGGTAGCATCGCCGTGAGCTTCAGTGGAAGATGAAGGACG
GGCTGGATCACGGGACCATACTTCTAAGACCTTCGGAATGCCAGGACAATCACGAAGAAGATGGTCCTCCTTCCAT
AAT
AGACAAGGAAACTTAACCTTCTGCGGAGGAGTGGGAAGGANTCAACTTCTAATGTCTGTGATGGAGCAACAGTTG
TGCATGTAGTCTCTGTTGTGTTGGTAGCCTCTCCCTTAGGAGACTTCTTCTTCTTGGTCTTCTTCTTCTTCTTCTTAG
CCACCTGGTTACTCGACTCGAAGACTTTCACCAAGGCGGAGTANGCTTGGCGTTAATCATGGTCATANCTGTTTCCT
GTGTTGAAATTGTTATCCGCTCACAATTCCACACAACATACNAGCCGGAAGCATAAAGTGTNNGCCTGGGGTGCCT
AATGAGTGAGCTAACTCACATTAATTGCGTTGCGCTCACTGCCCGCTTTCCNTTCGGGAAACCTGTCCTGCCANCTT
GCCTTGAATNAATCTGCCNCCCCCNGGGAAAAGCNGTTTCNTNTTTGGGCGCTCTTC RIPPT305 pPT305.seq (SEQ. ID. NO. 282)
TCAATCACCAATTATTTGGCTNTCTAGGTGTTTTTTTTCATATACCTAGATCGAGTCTTNNGCCTTTGAAATTCTTC
TTCTTCTTCTTCCTCTTCTTACTCTTCTCCTCCTCCTCCTCCTCCTTCATCTTCTTCTTACTCTTCTACATATTTGAA
ATCAGATTCTTCATCTTCATCTAATTTCTCCCCTTCTTTAGACTTTGTTATATGTGGCATAGTTTCATCCACTCCGAC RIPPT367 pPT367.seq (SEQ. ID. NO. 283)
CCTCTATTTGAAATGTGATCATCATATTGGACTTATAAGAGGTAACATATAACATACATTTCCAAAACTTTCGTAAG
GAGATCAACACTCTCCAAATAATTAGGAATCCCTCCTTCTAAGGTCAATCATAGGCATAAACCATGGATATAAATA
CAT
GATTGATAATATTAAGAWCTTATCAACATTCCATTCTTGTGGATGGTAATTCCATAGATGGGTTGTATAGATGGTTA
TCACCCACCCATGTCTATAGACTTGGTGACCCCTGAAGAGCCTCCAATACTCATACCACTCACTGCAATACCTCCA
ATGCATAATGCAACCACACATGTGGACATGTGGACATGTGTATGTGTGTGTGTGTGTGTTTGTGTGTGTGTGTGT
GTGTGTTCTCCTACCTAATGGATGAAGAAGCATTACCCTATGAAAGGTTTCCAGGAAACTCATTAACAAAAGTAACC
AACATTTGTATACCCACAAGTGGAGTGTCAATCAGACTGAGCACCATGGCTATAACCATCCATTCAAGCAAGGGTT
TCACCACGTCATCTCAACACTGAGACAACGT RIPPT369 pPT369.seq (SEQ. ID. NO. 284)
ATCAGATCATTTTTCAAATACTTAGACTAGATGGGCTAGATGCATGTTGTTAAGCATGCATTGTCATGGTTATGGTT
GTTGTGCACGAGCTTATTGTATGAAGTTAGTGTTATCATACATGATGTCGATATGTTGAAGTGAGTGTGTGTGTGTG
TGTGTGTGTGTGTGTGTGTAGATATCATGCTAATCTAGATTGATTTTGTAGGTGAGATAACCTCCCTTGAACTTCAC
TGATGTATGTTGATTATGGTTATGTTTGGTTTATCTAACAAGGTATATTTCAGGGAGAAGATCAAATATGACTAGC
ACAATGGTGGATTATAGTTCACGTGACTCTCCTTATAGGTCACATGAGGAGCGCAAAGATAAGTAGTGATGTGCCTC
ATAAATGGGT RIPPT376 pPT376.seq (SEQ. ID. NO. 285)
ATCATATAACTGCTCATTGCAATAAGGAATTGGTGATTCATGTGGTAATAAAATAATTGCCCACTACATCTTTGTGA
CTGCGATTAACCGCATCGATTAACACACACACACACACACACACACACACACATATATATATTGGTTATGTCTCAATA
TAACCATTTATAATATGATTTAACTTGGTCACATGGGTATACCAGGGCCGATTCTTTTATACTTGTTCTTTTAGCGAT
TCCACTATGCCATTATCACTTCTTCATCTTCCTTTTTATCTTTTTTTTGAAATATTTTCAAGTAATTCTTGAATGAAA
AATGAATACTACAGGCAACAAAAATGCATGTTACAATAGGTTCCATGCTCATTATTAATGGTCTTTTAGGTAAAAGC
ATGCCCTTCATGCTTCTAGGGCTGGTTGGGTCTGTGGATTTATTGTCACGAGTCAAAGGACTCAACATCATGTTGAT
AAGACCCTTCTCAGCAAAATGT RIPPT388 pPT388.seq (SEQ. ID. NO. 286)
ATCTTGTCCTTAGGCTCAAATCTGAACACAACACTCAAACATGCTCAATGTCTCTTCTCCTAAAGAACAAATCTGAA
TAAAGCACTCAAATATGCTCAATGTCTCTTCTCCTTACTCTATAACAACCTCTTTTTCTTTAATTCAATCATTGTTTC
TCACACAACACACACACACACACACACACACACAGAAACATCTATGTTTTTCTTAGTTGGGACCTCACATCCTCTTTTG
CATTAAAAGCATCACTTCAAATTTGTGTTTATCACCCCTACCTCCTGACATTCTCTAGGACTATGCTTCAACACTTA
TTTTTCTCACCATTCAAGTCCTCAAAGCCTCTTGTCACTCATCAACTTTGTTTCTTTCAACTATATCCAAATCCTCTT
TTACATTATATATCCTTTGTAGCATTTTTTTCCTTATCTCATCACCGTAGC RIPPT467 pPT467.seq (SEQ. ID. NO. 287)
ARKAAGCTTACACAACACTGCACACACAACACCAGTACTGCACATTCGAAGACCACACTATCTTTACCAAGCAACC
TTGCTTCTAGTGTCTTTCCACTATCCATACTTGTCCCAACATGCCACAAATCACAATGCTTTCATTCTGTTGATGTA
TCC
CTCAACATAGCATGTCCATTACATAAACATAGGCATAGTGTAAACACATAATATCAATCATATCCACATGATACTAA
CATCATAGATCTGTTAGGGATACTCTGCCCACTTGATTCCTCACGATACCAAGAACCTCTTCATGCTACTCACATGC
ATAAGCAATCATTCCTCCACAAGAATGATCCTTGGCGACCTTGTCATACAATGNCATACATACATACATATATACAT
ATAARCATCATCATAAAACAATCATGATCCCTAATGACCCAGTTAGACACACACACACACACACACACACACACAC
ACACACACACACATATATAAACATTAGCATAAAACAACCATGATCCCTAAGGACCCTGTCAGACAATGACATGCAT
ATATACATATATACATATATAGRCACCAGCATAATAATGATCACAACATAATTATCAGATAAGCTTGCATGCCTGCA
GGT RIPPT496 pPT496.seq (SEQ. ID. NO. 288)
CCTCCGTCCGCTTTGAATCCTCTTCCAAGCATTATACAATCATTGCTTAATGCCGAAAGGGGAGTYGGCCACCATTT
CTGTAATGTAAGAGTGCCTCGGGTCTGAYCCATCGGATCACCCATATAATTGTGTGTGTGTGTGTGTGTGTGTGTCC
CCGCTCCATTGTAACATGTCGATGCGATATTACAATGCGACTTATCGCAATCGCATATCGCATAAGCCCGCAGCCTT
CCCATATAACATGGTTTATTGCCAACGCCGATTGTGATTGCCGATCTACCTACCACCACCGATTGCGATTGTCGATC
TGCCAACAATTGCATGTCGCATTAGCCTCAACCTTTTGTTAAGTCCTCCCTTTGGCTTTTTGCGATGCGATAAAGCG
GTAATCGCATATCACAATGTTTT TABLE 3-continued

| SSR loci |
| --- |

RIPPT508 pPT508.seq (SEQ. ID. NO. 289)
GCATGATTTAATTTCCAGTAGTAATCTCCGTTTTTTATTGTTTGTTAAAATATATACGTATTTCAATATTCCTTTCCC
ACTTGAAACATCCTCAACTTAATATCCTGGGTTGGGGTCCGAGGATCTCCTTGCCAGTAGCAACTTGCAAATTGCAA
CAACCTTCACAANTTCAANATCCATTTAAACAAACCTGTCATACTCATCANAGGACACTTTACAAAATTGCCACTA
AGCAACTCTGGANATGGGTCAGTTTTGCATTATCTATACCAACTAGCATAGACCCGTCTTCACCCTACATCTATTAA
GCATTGGAAAGGGATAAAGAAAACAATGTGCAAACCACTTGGAANTTGGTGTTTAAAAAACCCAGGGTTAAAATGG
ATCTATGTTAGTTTCTTTTATTTACTTATTTTTTACACCACTTTTCTTGGCACAGGTTGGACATCTCTTATTCATTTT
AAGTTTATGCACATCACACACACACACACACACACACCTATGAAATCTCCCTTCACCACAAAAACTTGGCGTTAT
CATGGTCATAACTGTTTCCTGTGTTGAAATTGTTATCCGCTCACATTCCCCACAACATACAACCCGGAAACATNAA
NTTTTAAACCTGGGGTTGCCTAATGAATTAACTACTCCCATTAATTGCTTTGCCCCACNGCCCCTTTCCATCC RIPPT538 pPT538.seq (SEQ. ID. NO. 290)
GTAGGTCAGGTCATGCCATGGTAACTCTTCATCTCATGTTTACCCTGATAGGCCAGTGGAATTAGGTAACTTTTGGA
GGGTGTGTYACAAATTGGTATCATAGATTCCAAGTTCAAACACTTGGACTGGATGGGCGGGATGTGATTGTTATGCA
TGCATGTCAGTCATATGCATGCATTGTAGTAGCTATGGTTGTCATGTATGTATTCAGTGTTACTTTTTGATTTATCAT
GCATGATGTCGATGGGTAGATATGTTGGTGTCATTATATATATGTGTGTGTGTGTGTGTGTGTGTGTGTGTTGTTGCA
ACAAACATCCTCCAAAATTTTGTGT RIPPT540 pPT540.seq (SEQ. ID. NO. 291)
CCTTAGGACATTCTCTACTATTGTTATCTTAATGTTGTCATTAGTGGTAGGATCATTATTTTTAATTGTATACTTTGT
ATCTAATACACACMCACACACACACACACACACACTATGGATATTGTTCACACGAATCAATATTTATTAATAAGCG
GTAAGCTATAGARGAGGTTTCCTTTACAAAGAAACCWTTTWATTTAATCATATTTTAACATTCTCAACAAGTGACA
TCGCTTATTCTTTATATTATTATTTTTTAGGGTTA RIPPT548 pPT548.seq (SEQ. ID. NO. 292)
ACTAGATGTGTCCTCTAGTCCCATTGAACTACTTTTGTGGTCATTCGTTGGAAATTAATAAAATTATCTTATCTTAC
CTTTAATTACTCATTTATTGGCATTGAAATATTTTACTATGGTCGATGTGTGTGTGTGGGTGTGTGTGTGTGTGTGCG
AGTGAGCGCGTGCATGTGTGTGTGTGTGTGTGTGTGTGTGTGTGTGTGTGTGTGTGTGTGTGTGATTTGGAGATAAYTCTTC
CATGTWGAGTTTACAATTAGTTTGGAATTTTGTTAAGARAAAATCTCAACCTCCTTGTCTATTTTTGGAATCAATTG
GATCTCAATCCAACTATATATGTGTATCATATTTATGAATGAATAATCGTTTTWGATGTGTGAAAATTAGCTTTATT
TGTTGGTATCAAAGCCCTATGGGTCTGGGGAAACCTGGGCGTTAATCATGGTCATAGCTGTTTCCTGTGTGAAATTG
TTATCCGCTCACAATTCCACACAACATACGAGCCGGAAGCATAAAGTGTAAAGCCYGGGGTGCCTAATGAGTGAGC
TAACTCACATTAATTGCGTTGCGCTCACTGGCCCGCTTTCCARTCGGGAAACCTGTCGTGCCAGCTGCATTAATGAA
TCCGCCAACCCCCSGGGAAAAGCGGTTTGCCTTATTGGGCGCTCTCCGCTTCCTCGCTCAATGAATCCCT RIPPT556 pPT556.seq (SEQ. ID. NO. 293)
GTCTCTTAATTATGTTATGATCGTGATTACATTGCTGCCTATATTTGTGTGTGTGTGTGTGTGTGTGTGTGTGTATAG
ATATATATATGCCAATGTCTAATAGGGCTGTCAGGGATCATGATCTTTTATCATGATGTTTATATGTATATATGTATG
TCTGTATGTCATTTTCTGACAAGTATGGAAGCGATCATTGTTGTGGAGGAGTGATTTCTTATGTAGGTGAATGACAT
GAAGAAGCTCATGTTGTCAAGTGGGAAGAGTATCTCGAATAGATCTATGAGGTTAGTGGCATGTGGATATGAGTTTA
TATTATGTGATTATACTATCATAGGTAATGTCGAGGGATACATGAATGGAATGAGAAAGGTGTGATTTACAACATGC
TAGAAC RIPPT560 pPT560.seq (SEQ. ID. NO. 294)
ATCGCAATATAGCATTGGAACTTCACCGAAGGGCGAAGCTATACACACACACACACACACACACACACACACACAC
ACAAATATATATATATGCGATCTGATTGCTGGACCCAATAGCACCTTAACACTATATTCAATAAATATTTCAAATCT
AAGATAAAGCCATTATTATGGGATTTTGCAATATTTTAATGTATTTCTAAAATACAAATGGACAAGCCATTTGTGAC
TTTCGACAGTGACTTCTGGGTAGACCCAATAAGAGTATAGACTAGATTTAAGGACTTTTGAAGTTTGAAAGACTATG
TTTCGGTGGATTTTCACCATTTTGAATACATTTCTCCGTGTTAACAAAAAGCAGCTATTCTAGGGATTTTAAAGCCT
CGATGCACTCATCCATTTCAGTTTARGTKGCCATCTCCCCTGAATGTGTTTTGCAATGAWTGTTTAACGTTTTGAAA
GAAGAATTTGATTGGATAGAGGCCGGGAAAMARAAAGCCCAATAAGTTGGAAATGAATAAGGTTAAGAAATATTGG
CTTTAAAAGCCCTTGAAAARAAAAAAAAACCGAAGGGTTG RIPPT567 pPT567.seq (SEQ. ID. NO. 295)
CCTAGTTGACAACGTAATTAGTGTGCCATGAACAATCTATCACATGTGATTTGTATGATCCTCTTGTGGCAGCACCA
TCCAACTATATTGCAAAATCAACGTCATCCTGACATGTCTATCAATACACATGCCAACACATGCCAACTCCTCCAT
GACCAACATGCTACCATAAAGCTCCACCAATGCCATCATCTGATCAACATCAATGCCAATACATCYCAACACAAAC
CGTCATGAGTGATATCATATTATTGACATCAATGCCAACATAATCAATCCAATGTCAACTCAACTAGTAGCATAATG
ACCATGTTGACATTAATGCAAATACTATAATGTCAACACTATATKCTATAAATCTATATCGATCCCATCAATAGAGG
ATGCTAAGGGTTAGGTTGGTGAGGAGACTTGGGAGTTCATAGTGATGACACACACACACACACACACACACACACA
CACATGTTTTGTATTATTTTCTTAAATTTTCTTTTTCACATTGCTATTTTTTTTAATATTATACATATCATCCATATTG
GAATTGTTCTTAGGAAATTTTGTGTGTGTGTGCATGC RIPPT584 pPT584.seq (SEQ. ID. NO. 296)
TKTTACCCCGAACTCCAGAAAATGCAGAMATTGGGACGGCTCACATGGCTMTGGGGAGGGCTGGAGAAGCCCCAG
GAAGGCACAAGCCAAGCAATACAAATCGAAGATGAGCAGTCTGTAGAGGCCGAWATGGAAGAAGAAGACAATGAG
GAAGCATAGCAGGCTGCAGAGACAGAAACAGAAGAAGAATACGACTAGGAAGCAGAGCASTCTGCWGAGACAGAA
ACGGAAAMAGAAGATGTCGAGGAAGAAGAGCAGTCTGCAGAGGCTSAAGTAGAAGAAGAAGAAGAGGAGGCAGAG
CAGTCTAAAGAGGAAGGAGACGAGAAAAAAGAAGCTGAGCGGTCTKAGCASGAKGAAGGAATGGAACAACAGGAAG
GTAGCCCATTACCARACCCGTTAGGGGAAGATGAATTGGCCAACATTTTGGCCTATATGGGTGAATATGGAAAACC
CTG RIPPT609 pPT609.seq (SEQ. ID. NO. 297)
GTCGGCAGATCAGAACGGTGAAACAAAATGCAGAGGGGCTTAAACACACACACACACACACACACACATATACGCT
CGATCCAATGGTGCAATCATTGAAATCAACGGATAGCAATCAAAGCATTATAGAGGATTAGCCGATATGTTATAAGT
TATATACGTGATTCGATGGACTGGACTCGCTAACATTACAAGCCATATTGTATGGATCTTGAGATCCATCAAACACC TABLE 3-continued SSR loci CCTTTTTAACGTATTTTCACAGTTTCATTTGTTAAATGAAATGTGAAGGAGAAAGGCCAATTGTGACTTACGATAGC
GACCTACGGGTAGACCCGATAGGAAAATAAAGCATAGTTATGGGAATTTCAAGTCTGGAATTGTGTTTTATGCGGAC
TTTCCCATGTTTTCACAGCATTCTCTGTGTAACCAAAGAATGACTGTTACTAAGGGATTCCAAGTGCCGATTTCCCT
CATTCGTTGCAAAAACAAGTGGAAGCTTATCAGTAGCATATTATGGCTTTAACATTTGAAATATGCAAGCTCAAGTT
TTATTCTTCATGCTTAAGGGAAAAATTCTTATATACAATATANGTTCAAGATATGCCCTCTTTATTTAAGGCTTATTT
AATATGATATAGGTCATTTAAATTTTAGTATTTATCCTTTACACCATTAACATAACNTATTAATTGTGCATGTAACC
CATGGATAANTAGATTAA RIPPT619 pPT619.seq (SEQ. ID. NO. 298)
ATCACAACAGCTCTCTTAATAGCCTCGGTATATATGTGTGTGTGTGTGTGTGTGTGTGTGCGTGCTCCTTCATGG
TTTCAATATTGATGAAAGTAAAGTCACAGTCCTTATCTCATTGATCTCAGTATAATGAAAGGAAGCAGTATCACATG
CATTGTGATGTTTTAAAGACATTCTCTTCAGCGTTGCTATGTGCTACGCCATAGGCCATAGCACCATAGCTAGGACT
ACCTTGGGGCTATTGTATTAGGTCTATTTAGAGACATCATGGTGATGAAGTGCAACATAACATGATGGGTGCACTAG
TGTAATGAAGTACAGTATAATGATGAGTGTAGCGGTATGAAGGTTAGCAGCACCATGATGGTTGGATGCAGCATGAT
GACTGGATGCAGCATGGTTGATGTACCGCACTGTTGGGTGCAACATGGTGATGATGAGTGCAGCACAGTGATGATG
GACATGGTACGAAGGGTGCAACACAATGATGGGTGCAGCAAAGTGATAGGTATAGCTTGGTTCAAATCTGCTACCT
CAGGTGTCATCTTCTTAGAAAAGATCNCTGCTCTTATTTTGTCAAGTCTAAATGTTGACTTCTGAAGTATATGTT RIPPT621 pPT621.seq (SEQ. ID. NO. 299)
ACGTATATAGTGTATGAGTTGGACCTTGAGTGGCTTCTATGACTTGAAGAAAACAAAAAACATAGATAAGCACATGT
ATAGTTGCGCAAAAGAAGAGGAATTATGAGTAGTTGGTTCCAAAAAACTTGTCGGATTCAACGTGCCCATATTGCCA
AAACTAACCTGCGATGAGACAAAAGGAATTCCTTAGTTAACCCCCGATTCTCGTAAAGAAATCTAGCATGAGAAAA
TATGATAAACACGGATAAGCAATTTAAACTTTACCTTGGCAAAGGGAAGCAAAGTCATTGCAATAAAACCATGCAA
CAAAACAAACACATCAAAGTTGAACATACCCATGAATATGTGTGTGTGTGTGTGTGTGTGTGTGTGTGGAGAGAGAG
AGAGAGAGAGAGAGAGAGACTCGTTCAAAAGAGGACGAATACAGATTCTAGAGCTTGAAAAGGGTTTTTTCAATAA
TTGCCAATACTCAACANATTGTGGCTTCCACAAGGG RIPPT627 pPT627.seq (SEQ. ID. NO. 300)
GTGTTCTTTTATCTCTGTGATCTAGACGCACACCATATGACTATTACTTACTAGGATTTGGATGAATTCATGTGGCA
AAAAATCACTGCAGTTTGGATGAATTTATGTGTCAAAAAATCACAGTGGTTTTGATGAATTTATGTGACAAACAACC
CTTGCGTTTTGGAAAACAATAGTTACAGTTTGAGTGAATTTATATGGAAAATATTCATTGTGGTATGAGTGAGTTTT
ATAGAACTATATTTTGTGGCTCTTGCGCACGTGCACACACACACACACACACACACACACGCATGTTGGCTTGATG
GGTCCTGACCCAGGTTCAGAGTTAATTAGCCAAAAAAGTCCTTGT RIPPT629 pPT629.seq (SEQ. ID. NO. 301)
ATCTCCACTCTTAAAGAGAGGAATGACCACACTAGTAGTCCACTCTCTCGGAAAGCCGTCCTAGATGATCCCATTG
AAAATTCCTTTTAAATGAGGAGCAAGGAGCTTAGCTCCCCATTTTAGGAATTCAGCTTTAAGCTCGTCTATGTCCTC
TGCTTTACTGCTTGCTAGATTCTTTATTCTCTGCTTGATGTCATCCTCTGTGAATAGTTCCACTGAATTGTTCACTAT
GGGGGGTATCTTTCTCATGGACCCACTCATAAAGGAGCCTCACATACTCCAACCATTTGCCACCTATAATACTGTTT
TTAGTCTGCTTTATCCTTTGTTTTAGCTCTTTCCAAAATCCCTTGGGGTTGTGCTTTCCCAGAGAGATTAACTCCTTT
CTTCTTCCACACACACACACACACACACACACACACACATATATATTATACTAATTTTCCATATGTCTTCTTGTTTT
CTTGCTCCATTTTCTCACTTTTAGAGATCTCCTGGCTACCTTGCATTCTTCATCATACCATGGATTTGTTGGAAAAGT RIPPT630 pPT630.seq (SEQ. ID. NO. 302)
ACGCAAGCTTGATACAACGCTGCAATATATTTATATATGCAGGGAAAACAACACACACACACACACACACACACA
TATATATACATGCAATGGCACCATATATATACACAGCAATAGAGAAGATATTTACACGCTCAGCTTTCACACTCAGC
CAACATATATACATACACACAGTCAATATATATACACATAGTCAATTTATATAAACGCACAATATGCAGATATTCAC
GAGTAGTAGGGAATCAGAATAGTGATGCATGTTATAGTGATGCTCTGTCTATAGGGAATCAGATATTCACGGGTAGT
AGGCATGTTATAGTGATGCTTTGTCTACATAACTACAGTCAAGATCTGGTGAGAACAAATCCCGATGGATTTATAGAT RIPPT644 pPT644.seq (SEQ. ID. NO. 303)
AGTTTCTTGTCTTCGGTTAATTTTTGTTGCCTCTCATCTGTCACTCTTACAAGCCTCTAACTTGCATAATCATAAAAT
AATAGTCCAATTGTCCATGTATCTGGTTACGAGGATTAAAACAAAGCATAGGTTGTGATCCAAGTCCCCTGCAACAC
ACACACACACACACACACACACACACATATAATTAAGGGTTGAAAATAGAGACTGTAAAAGGAATGGCTTATGAGA
TTTATTCATAAATCCACTCTTGCCACACTCTAATTATTTTTATTAAATAAATACATCACTAAAGGTCACTCAAGATC
CAAGAGAATAGGACCGAATGGACCATTATTAGCATAATAGAAAAATTACAACAATTGGATAAATTTAATAGATTAC
ATGGCAATCAAAACAAACTCCTATCATAACAATCCCACTCATTAAGGAACCAACTCCTTTAATAAAATATTTTGACC
TCTCAGTCAATGGATTTTATGAATGCTCTTGTATCGT RIPPT647 pPT647.seq (SEQ. ID. NO. 304)
ACCTACAAAAACCACCATTATGCTGCTCAAAACCACCTTTGCGGATGAAAAACCACCTTGGAAAATTGTGTTCTGG
TATGGCAGGTTCGACACCTGCATAACAATTAAATAAAGTTTGGGCGGCTTGAATACCAAGCTCCACCGCTTGGTCTA
TTGGCCATCGAACTTGTGTTAAGGCGCTAGTATATATAGTGGGAGGTTGGCGGGTCGAAACCCCCACCCGACACTC
CAACATTTTACATGGAATTGATATGATATGATATGGATAGATATATGTGTGTGTGTGTGTGTGTGTGTGTGTGATATT
TTATATGGTTTAATACATATGTTTCAATACACATATTCTGGTAAGGTGACTGGTGGTCGTGGGGTTGACCCCGACCG
TCCGACCCTTTTTCGGTGGCCACATCCTGAAACATTAAATATAACCATATCCCTTCTGAT RIPPT649 pPT649.seq (SEQ. ID. NO. 305)
ACATATGTAGTGAGCTTTANGGCTTTAGAGAGTGATTTTCGATCCGATCCAATGGTTCCATATAAATATGTAAGCCT
ACAGGCAGAAAATAGGAGGCCACCAATAGTCGAATCGGGCCTGTACGTGTGTGTGTGTGTGTGTGTGTGTGTGTGTG
CGAGACCAAGGAGTCTCGGATGTNATCTATATTTTACATTAATATATGCAAGATTATTTCTTGTCTATGTCATGATG
CTTGAGAAGTAATTTATGTGTGAATTACTTGTGAATTTGTAGGCTTTGTTGTAGGTTGCAGGTANAATTTTGAAGGA
CACAGAGGAGCAAAGATGATTCAGAGAAATCATAGAGGGATCATTGAATCCNAGTGAAAGGTAGAGTTTCCTTGGA
GAGGGGTTGTGAAGCAAGAATTCGCTAAGGAATCTAGCGCAGAGAAAGCTGAACAATGGAAGTANAAGACAGAGTT
TGAATGACGCTGCTGGGAAAGAAATATGATTGGGAGAAATCATATTGATCCATTCGAGGGG TABLE 3-continued

| SSR loci |
| --- |

RIPPT658 pPT658.seq (SEQ. ID. NO. 306)
ATCATAGCTCTTAGGTTCAACAATTGGACTAGATGGGTGGAATGTATTTGTCATGCATGCATGTTAGTTCTATATGT
GTTCATTATGCATGCATTACAAATGTCATTGTTGTAAGTAGTTTCATCATGTAAAGGTTGATGATATTGATGTCGAG
ATGATAGATATGTTGATTTAATTATATATGTGTGTGTGTGTGTGTGTGTGTGTGTTTTGCTAATCTAGATTGATCTTG
CAAATAGGATAACGTCCTCTAAACTTCACTAAGGTATGTTGTTTATGTCTACGTTTGGTTGATTTAAAAGCGTATAT
TTTCATATTGGTAGAAGATCAAGGATGACAAGTAAAATTGTGGACTACAGTTCACATGATTCTCCATACCTATCAAA
TGAGTAGGATGGTGATGAGTAAGCTTCCAACCCGAATGTCCCCGATAGTCAGGCGTGTCACCCATCCTATTGATGTT
GTCACCCCTTATTANGAAAGGGGAGTGGTAACGANGANGANATTGTGAGGAACCTCGAGGGGTTGACTCATGGTAT
CCCGAANTATGCTCAGATAGGANACATGCCCTGACGANACCAGAAGCACACAGTGAGANTCTTAGATCGGATCCAC
CGACTGCTAAATCGAATTGCACAAGTTGTCTCATGCTACCATGANCACTATGCTCAGTAATTCCTANGTCCNACAC
TTACATATTTTTT RIPPT675 pPT675.seq (SEQ. ID. NO. 307)
ATCTTGATCTTTTATCTTTCATTGCAATCAAATATAACCATAGCTATCTTTGATATTGTGAAATAATATTTGATGTGG
TTGGTGTTTACAATCTCCTCCACACTTATGTTCTATGCATATAAGGATTTCTGATGGCTTGAAATGTATTCGTATATC
CTTCCAAAAACCTACAACGTTGCCTCTGAGATATAAGAATGCAAATCAATGAACGCATACCAAGGAAGCTATCAAA
TCGCCTGATGGATCCAGATAGGTTTTCATAGTCGGTGATTGTGTCTATCTTCGACCCTAACAGATGTCAAGGCCAAA
GGCAGAGAGCTATGCATTGTTTTCATAACTGTTGTTTTGATATATATATATGTGTGTGTGTGTGTGTGTGTGTGTGCG
TGTGGCTTTTAAATATTGTTTTGGCATATATATGTTGTTCAGCTTTGGCACACCATAGCGGGTAATTTGAATGCAGA
CATTGAGGGAGCTTTCTGATTTGCTAACCATTGCGAAAAGG RIPPT683 pPT683.seq (SEQ. ID. NO. 308)
GCAAGAGTTTTCCTGTGAAACCAATCCTTCTGCAATCTTTATTTCATCCATCGATATGTGTGTGTGTGTGTGTGTGT
GTGTGCTTCAACAGTGCAAGAGCAAGCATTATAAACGAGATAACCTTTTAATTAATATTGATAGAGCTGCAGCAGCA
AGAGGAGCCAAGGAGACCAAGAGGGCTGCGAGAAGCCAGAGGAATCAGGGAGTCATGAAGAGTCCTGGTGCAGAGT
TATCTATCTATACAATATCACCGAGCCTGCATAGCACTTAGTGAGTTTTCTTTTTGGTGAAGTCTTTCATTTAACGA
AACCCAGGACCATCAGTCGTCAACACTCATAACAGGGATTGCCCAAAAGCCCGTAATATTTACAAATTGCATTTTA
AAAAGCGTCGGGCACCAGAGAACGTCTATTAAAAGAATTGCAAGAAGACGAGAATTTTCATGTTGCCCAAGGCCAT
CAAGCCCAGAGGTAATTCGAATTGAGAGTCAGGCACACAAGTGGG RIPPT688 pPT688.seq (SEQ. ID. NO. 309)
ATGAGAGAAATCTCAAACACAACACAACACGCACACACACACACACACACACACACACACACACACACATATGTA
AGCATATGAACACTTATTTCAGTTATGCATTCACGAGCTAAGTCTAGGCTGAAGTAGCACAAGTTTAGGAGGGATAA
CACACACATTTGTTTTGAAAGCGACAAGTCGAATTGGGTTGAATACCTTCAGAAATCTCAGGAGGGATAACCCAGG
AGGACCTACATATATCATAGTATATATAAAGACTGCGCATCAGAG RIPPT689 pPT689.seq (SEQ. ID. NO. 310)
CTAAGTCCATCGAGAATGAGAAAGAGGACATATTTCCAAAGTAAAAGAACCTTAAAGAATTTGGGGGCTGAGCTCA
AGGACTTGGAAGATGAGTTAAATATCTGCAGGGAAGAACTTAGAAACCTCACTTGGGAATAGTGAGAGTTGATTGA
GTGGAATGTTTAACTATGAAAATAGTTGTGAGAAATGACATATAAAGATGAATCCTTGAAAAGGAAAAATGGAATTG
ACAGGAAGAGGTCTCGTGAGGTTGAATAGGAGAAGGGGATATTCTCCTATTGGTGTTGTGGAGAAGAAAATTTGAGA
AAGGACTATCCCCGTAGGAAGAATAAGAAAGAAACTTTCCCCTACGAGCCACAGGGGGAACATGTCNATGATGCAG
GATGCCCANAAANGCTGAGGGGGGACTCCTTCAAGCTCCTTGACACATATATATGTGTGTGTGTGTGTGTGTGTGTG
TTTGTTGAAAACATCACCTGTGAACTTTTGGGGAATGTNAGACTTCNNGGTTGCTGTGAGCCTTNTAAAGAAGTCTT
GAACTAATTTTGGTTTATGAATATGCATNTGT RIPPT690 pPT690.seq (SEQ. ID. NO. 311)
ACAATTCCCCACATCGTTGTAATCTCCTGCTTTGAGACCTTAATAACAATTCTATTATGGACTAAAACTCAATCGCT
CCATTATGTTTGTGTTGACGTAGTAAGTTGCGTCCATATTATAATCCCTACCCAACTATGTCCAACCTTCATAATAT
TTATTCCCATACAATAGTATATGATTCCTAGATGGACCTGGGGGTCAAGACAATCAACGCCGCTTTAGACAAGGTTA
TGGGTAATGCCAAGTAAATTATCATTCCACACACACACACACACACACACACACACACACACATATATAATTTGGT
GGGCTTATGTCGACAATACCAACGTTGTCTATCCCTCTAAGAACAAATCATTATATTATATGTAATGTATAAGATGG
GATCAACAATCTACATTGACTACCGTCAACATAATGGTGAACCGTGAGTTTCCATCACGGAGG RIPPT692 pPT692.seq (SEQ. ID. NO. 312)
ATCTTTGGGGCACAATCACTCACGGATTGAGATACACTGTCAGNAGATGTGAGGTTGCATGGTTATTCTGAATGTTG
ATTGGGTTGGAAGTGTAGTGGATCGCAAGAGCACTTATGGATGTTGTTTTTCTTTGGGCTCTGCTTTGATATCTTGG
ATGAGCGAGAAGCAAAAATCGGTTGCTTTGAGCACCATCGANGTTGAATACATAGCTGCTAGTATGGCCTCCTGTG
AAGCTGTCTGGTTGAGGAAGCTCTTCAGTGAGTTTTTTGGACATATGTTGGATCGTGATCCTCTGTGACAACCAGAG
TGGAATCTGATTATCAAATAATCTTGTGATTCATGATCACTCCAAGCACACACACACACACACACACACACACACA
CACACACACACATATATNTATATATCAACGACCTTCTCNTCAATCCCAATGTGATGGAAGCCTTATTTCTCCTCNTTGT RIPPT700 pPT700.seq (SEQ. ID. NO. 313)
ATCATATAACTGCTCATCGCAATCGGGAATCGGTGATTCTTATGGTAATAATGTAATTGCCTGCTGCATCTTTGCAA
TTGCGATTAACTGCATTGCTTAAAACACACACACACACACACACACACACACACACATATATATATTGGTTATGGCTC
CATATAACCATTTATAAGGTGATTTAACTTGGTCACATGGGTATACTAGGGTCAATTCTTTTATACTTGTGCTTTTAG
CGATTCGGCTATGCCATTATCACTTCTTCATCTTGCTTTTATCTTTTTTTGAAATATTTTCAAGTGATTATTGAGTGA
AAAATGAATACGATACGTAATAAAAATGCATGTTACAACAGAAGGTATGTCTAATTTCTCTCTAGATTTTGATTTCT
GTGAAAATTGTGTATTTGGGAAGCATAATCGGGTGAGTTTCCCCTCTAGTGCTAAGANGGCGAAACATATATTANAG
CTTGTGCACAGTGATGTGTTTGGACCTATGTCGGTTCCATCACTGGGTAAGTCTATGT RIPPT767 pPT767.seq (SEQ. ID. NO. 314)
ACATATGATTCTACAAATATCATTTAAGAACACACACACACACACACACACACATATACCACCATCATGATGTGAC
AAATGATGATCCTTCCCCGATTCATGTTATAATCTCCTTGATCCCTGACCAATCTCATCAACATGCATAGAAAGTCG
CCCTCTAGTTGATGCATGAGACTTAATTGATGCTACATCGCATTTACACCTCAAAGAATCAAGTGGTAACTGCTCAT TABLE 3-continued SSR loci GTGATGATCCAGACCCTCGTTCCATACATACATACATACATACATACATACATACATATATATATAATCTTTAAAAAAACC
CCAAGTTACCTCATGCATTTAAAATCTTTAAAATTGTTATTTAAAAACATCAAGAATTCAAAAAATTGATAAGACAA
GTAAATGTAACTATCCAAGGGTTTTCTTCAAAAAATTTTGATGTAAATTCTTTATTTCAAATATACTCAAGACTAAA
AACACAAATTCTGAAGTGCACATTTTGATAATTAAATACATTTTTTTAAAACATGTCAAATTCACCAAGTTGAAAGA
AACACATGGTCATTAAAAACATACACATATCAAAGAT RIPPT789 pPT789.seq (SEQ. ID. NO. 315)
ATCAATTGAAATATACAAAAGAAGATACTGAAAGGAAGGACATTGACCACAAACAAAAATATAAGAAGAATGTAGA
TTTATTGAACAAGCTATGGCAATAAATAGCCAATTTGAGAGAAAATTATGAAAGAAAAATTTGATAGCTCTAACAAG
GATCAAAGGATGTGTCTGTTTTATTGCCCAAATGATCACATGTCTCCACAGAAGGAAAGATACACTCTTATTCTCAA
GAGGAGGGCTTGTAGAATCATCCCAAGCATCCTCAAGTTTCAAAATAGCAATTTTTAGGTGTTGTATCTATGTAGAC
ACATTTCAACATGTCACACACACACACACACACACACACACACACACACACACATATATATTCTTGTTAACATGCATTAT
ATATCATTATATTTTCCATTAAACCACATTTTTGAATAAATTTCTAGTCTTTTTTGAGGATTTACACTTATGTCTCCT
TCATGGAGTTTTTATCTGGTTGTGGTCTCATTGGGATCTAGTTACTCTTTTATTTTTGGACAATGTNATGGAATTTTA
TAAACTGATAGCTTATTGAAGTGAGAAATCGGTGTTATGGAATGT RIPPT790 pPT790.seq (SEQ. ID. NO. 316)
ACTTTGTATTTATCATTCTTTTTCATATGAATGTAAAAGCATGATTTACCTATTTTATTGTTCAGCAATAGCCTGTTG
TAGATGGGAATGTTTATAAGTTTTCTAGAATGTTATCATTCCATTTTGTGTGTAGTTCTGTTAAATGTTGCATGATGT
GAATGCCTTCACTTCATGTTTACTCGTTAATGCGCTTACTAGCTTTTTTTCCTCATGAGAAATATGTTTAAATTTGTG
AATTGTGTCCATGGGAACAGGGTCACCTTCGGGCTCAAACCCTAAATCATTAAAGTTAGTTACTCTGTTGCTATTTT
GGTCTCGCACACACACACACACACACACACACACACACACACACACACACACACACACACACACATATATATATATTGCTTCAC
ATTTCGTGTTTAAGCCTCACCGATTCTTGGCCTGTAATTCATTGCTCCGGCTACGGA RIPPT791 pPT791.seq (SEQ. ID. NO. 317)
ACTATATTTATTGATTTGAAATATTAAGAAGAGCATCTGACAAAGAATAAAGAGGTTAGAAAAGAGAAGTANGCTG
AGAAGTANGAGGGAAAGTATGTGCTAAAGCTAAGGTAGAAGCCATGACGCANAAGCATGGTAAAAGGGACAATATG
GAAGGATCCACAACCAATGGATGCAACAAAGAGAATCCATGAGAAGTGGGGCGACGGAAGATGACTAGTGACCAAT
AAAGCATACATATATATGTGTGTGTGTGTGTGTGTGTGTGTGTGTGTGTGTTTGTGTAAACACTCCAAATACATAGACC
AGCAACAAGCCCCNAGGCAAAGAATTAGATAAAGGAGCNAGAAGAGCATGAAGGCTAGTTGAGGAATACNAAGGG
AGAAGCAGAAGGGAGGCGAAATGAGACCAGAGGGCTAAAGAAAGAGAGTAGTTGTANAAAATGATATTATTCTAAG
AGTGGACCNACAATGTTGTGCCCNAAGCCTGCTACTAGGGAACAAAGAAACNAACTATGGAAGCGAAAAGG RIPPT792 pPT792.seq (SEQ. ID. NO. 318)
ATCTAATACCACAGAATGGTATCGGAACTCTAAGGTTCAACACTAGGACTGGATGGGCTGAATGTGTTTTTCATGCA
TGCACGTTAGTTGTATATGTGTTCATTATGAATGCCTAGTGATTTTCATTATTGTGAGTAGTGCAGTCATGTAGAGGT
TGATGATGTCGATGTTGAGATGATTGATATATTGATATATGTGTGTGTGTGTGTGTGTGTGTGTGTGTGTGTGTGTGC
GTGTGTGTGTGTTGTGCTAATACATATTGATCTTGTAGATGAGATAGCCTCCCTTGAACTTCTCTAAGGTATGTTGA
GTATGTTTGTATTTGGTTTATCTAACATGCTGTGTTTGCAAGAAGTAGAGGATCAAAGTTGACAAGTAAAATGGTGG
ACTATAGTTCACGTGATTCTCCCTAAAGATAAAATGAACAACATAGTGATGAGT RIPPT799 pPT799.seq (SEQ. ID. NO. 319)
ATCTCTCCACAGCTNNANAGACANATTGTGGGGGTAGAGTCCTCTCATTATGANAGACTCCTATGACATCTTTTTC
ATGTTCTTTCGTGTTATCACCAACATANAGGAGATTAACTCCTTANGATATTTTTTATGGGATATGTCTTTGCATAT
GTATTGGATTATGATCCTAAGCCTTAGAAACCCTTATNTTGACTAATGTATGCTAAGTATATTTGTGTTGTAAAACT
CTTTTGTGATATATAATGTGTGTGTGTGTGTGTGTGTGTGTGTANGTGCATGTGTTNCAGCCTCANTATTGTACACTTG
TGAATGTTGTCTTATGATGTTNGCATTCAGGTTTCTACTGAATGTATCATATGACATGGGTGACAAANTTANTGTGA
CAAATGTCCANATATGACATNNTTANCCCATGAATAACCTAATGTCTTAGAATCNAGTAATATAAATGTNTGAAAN
GGTGGTGAATCCCATTCTAGCANANGT RIPPT814 pPT814.seq (SEQ. ID. NO. 320)
ATCAAGAGAATAAGTTTGCCCAAATTTGAACAAGCTGTAGCATGAAGATCACTGGTAGTAGCAACAGATGCACACA
CTAAATCAACCTTCCCTTCAATTGAATCAACACTGAAGCACTGAATCAATCTTGGCTCACCAAGTTCTACTCTTACT
CTCCAAGTCTCTCCCTCACAACCTTCTTCAACTCTCTCCAACCCTCTCTCAAGTTTGAATTCTTCTTTCACAATGCG
CAAGTAGTGAGGGAAAAAAGAATGAGGCGCACACATACACACACACACACACACACACACAGAGATATATATATAT
ATATATAGGAGGAGCAACGAATCAATGCCATAAACGGGGATTAACTCGCATGCCAAGAGGGAGAGTAACATATGCC
CTTTTAGGAAATGTAACTCATGCCATTAAGAAGGT RIPPT815 pPT815.seq (SEQ. ID. NO. 321)
ACTTCATTTAGGTTTTAACATTTTTCAATAAATTAGCAAAGGAATGAAAACGAACAAGCCATGGTTAATTTACTAGA
AATAACTCTCTCTCTCTCTCTCACACACACACACACACATGCATGCAAGTAAACACTAAACTCTCTCTCTCTCTC
TCTCTCTCTCTCACACACACACACACACACGCACACATGCATGCAAGTAAACACTAAACTCTCTCTCTCTCTCTCT
CTCTCTCTCTCTCACACACACACACACACACACACACACACACACACACACACAAGTAAACACTAAATCTACAACC
GTAAAATATATGTCAATAATAATGCTAAGTAGAGAGG RIPPT841 pPT841.seq (SEQ. ID. NO. 322)
ATCAAATTCACTGAGATAAAATCGTAATAGATGTTGATTCAGGTGCATGGTGGTGATGTTACAGGTTTAGCTTCTTC
GTTGGGCACTAAGATGCTTAGAGTTGAAGCCCTAAAGAGGGCTGAGTCCTTCCTCACTTCAAAATAGACATTGCATT
GCTCAGATATTCACAAGAGTGATACCACAAGGCTGGGCATTGAAGTCATGCTTTAAACGTGCTTCCCTTGCTTCAGA
CTTGGCCTTACAGCATAGTGTCATATGCGTCAACTTAGGTTCAGAGGAATCCATAGATCATGCTCAGAACAACGAA
ACCAACTCTGTTTTTATCTCAGAAACTCGTGGATGATTAGAAGCGGCCACACACACACACACACACACACACACAC
ACACATGTATATACCCAAAGTTTGCATTTGC RIPPT846 pPT846.seq (SEQ. ID. NO. 323)
ACCTCATAGATTTTAGACCATATACTAATCCAATGGATGAGAGAGATTATACAATCAACGTATCCGATTTAATTACA
TGCCCCCCTCCTCCCTGTGACATCACCGAGGGGGGTGTCACATTCATGGTTCCAATGTGGGATTCCACCTACATATA
TATATATATATGTGTGTGTGTGTGTGTGTGTGTGTGTGTGTGTGTTATAATTATCACGAGATCCACGCTTATCATTATAC TABLE 3-continued

| SSR loci |
|---|

AACCATAGGTATAATTACTTATAGATTGGGTCCCTTGCTCCACTTAATTACATCCCCCATGTATATGTGGATGTGAC
AATCACAAGACCCCTATTTTAGTTATCCATATATGTATATATGACCTTAATATTTGTGGACCCCCTCTTTACCTTTA
TATGACTTAATGCTAATAGAAACGACATAGTGAGGGCCCACCTTC

RIPPT852 pPT852.seq (SEQ. ID. NO. 324)
ATCTATGTAGATCGCATACCACATAGAAAATACCCTGGTTTATATTAGAATAAGTTAATTAGAAGATTTGCATGATA
GAATAGGTCATTTAGATTATCATTATTTTATTTGCAAGCGGTTATGAACCGCCCACTCTCATATTAAAACCCACACT
AGGAAATTGGTCCCATTATCCCCAGTCGGAGCCACCACTTTAAACGAAAAAGGAGTTGTCTTAAGGTCCAGATCGG
GTAGTTATCCCCCATGTTGTTGCAACGATTTTTGAGGCCCCAACAGAACCCTTCCAATCCTTTAACATATTTGGCTT
CCTCTCTTAAAGGTCAGATGAGTTTGCACTCTCTAGTCACTTCTATATAAAACTTCNTATGTGTGTGTGTGTGTGTG
TGTGTGTGTGTGTGTGTGTTTATTTCTCTCGTCNAGGNAATGAAAGCATAGTGCTTCTACCCNGAAATTAAGT RIPPT860 pPT860.seq (SEQ. ID. NO. 325)
GNAGAATATTGAGCAGACATCATCAACACTAAGTAATGTCTAACAAGGACCCTCAATAATTCTCATATGTTTTTTAC
TTATAACCATGAGTCTTGTAGATAGAGAGTGCATCTGTGTGTGTGTGTGTGTGTGTGTGTGAGTGTATGAGTGTTTG
AAAGAGTGGTTGTAATCTGTGCTTTGAGAGACTAGAGACTAGAAAGCTCTACTCTTTGAGGCATAACCTGGTATGTA
ACAATTTTCTTGAATTAATACTGAAGCCTACTGGGCTGCCTGTCTGAGGACAGTTTGTTTCGAGATCATCTAAAAGC
GAGATTTTAAAGCGAGTTGGAGAAGCGAAAGAGTTGCGTGTCCTCGTATTTCTCGAGCTGGTGTGAGGAATTTCAGC
ATACTCTTCAGAGGTTCAAGTAAGTTATTGACTCCATCATGTTGT RIPPT905 pPT905.seq (SEQ. ID. NO. 326)
ATCTAAACTTTTGTGCAAATGTAACACGGATCTCTGGAAACCATGAACTACACACACACACACACACACACACACA
CACACATGTTGGAAATAATACTGATAGGGGGGGTGAATCAGTATTATCAAGTCAGATATTCCTTTTCCAAAATCAAT
TGATATACGCTACTTCAGTTAATTAAACCCGCGTATATACGCAACTATTCTGAGGGAAACCAGCGTATACAAAGCA
AACTATTGATATAATTTATCTTTTTGATGTTGATTGTTAATCTGTGTTTCCATAATCAAATAACCAGTAACTAGAAAT
AGTAAAACAAAGCAGAAAGACAATTGCACACAAGAACACAAGATATAAGGTGGAAACCCAATGTGGGTGAAAACCA
CCTGCTGCAATTCGTCTCTATCTTCCTTTAAATTAGAAACTTCTTTTACAATGC RIPPT921 pPT921.seq (SEQ. ID. NO. 327)
GCTCAAATAGAGAATATGGAAATTTTCCGCAAACTATGTGACAACCCTAAGTTATAGAAAGGTATGTTGACACCTTT
TGAGATCCTATACCTGATGCATGAAAAGTGGGAACCTATGATGACAATATTGTAAGCTAGAAAAAGGATAGTTTGAG
GAAACATGAATACATCTAACAATGAAAGTGTATGTTAACATCTTAAGGATTTTGTTTTCCTCATAATCACCTAAAGA
ATTTCTAATGAGTATNGGGAGATGTCNTAAAAAATGTCTGACATGTCACAACACACACACNCACACACACACACAC
NCACATATATATTCTACATATAGAAAGAAAGAAAATCGATCAAATAAAATTCCGATAACCGNGAATGTCNTCGTAT
GATGTGTTGACATGGAAAGTGGCATATGCTATGCCCTAAAT RIPPT932 pPT932.seq (SEQ. ID. NO. 328)
ATCTCGTCTGCAAGACCGACTGGATTAGCACAACACACACACACACACACACACAAACATAATCAAATCAACATATAG
TCATCATTCCAACCATTGTCAAACTATCAATGTATGAGCATACCCACCACATATCATGACCTCATGCATGGTAACTA
CTACCATATCACTGTACGCATAACAACATGTGTATGAAACGCACACATACCNCTGTGTTATGTGTGTGTGTGTATGT
ATAGGTGTATATGTGTGTGTGTGTGCGTGTGTNTGTGTGTGTACAACGACACCATCAAATTTCACATGGTGACACGA
CTAAAACCATACCCAAGACCATGCATACACAACCAATACATAGACCATAAACATAAGAACACATATGCAACCAACA
TGAATGCATGACCAACACAACACCCATTCAATCCAAGGGGCGAAACATGCTATGATACCACTCTATTACACCCTCT
TCCCACATCTACCCAAGTAACCGACTAACCAGGGTAAAAATGTGATGAGAGGCTACTATGATCTAAGTAACCTCCC
CATGT RIPPT941 pPT941.seq (SEQ. ID. NO. 329)
CCATCTTTGATAGGATTGTTGTGGAAATTGTGTGGGGTCCAAAGTTGCCCATTCGAGTCGCCAGACATCTGCACAAG
TTGTGTGAGTGAGCAATGCCGTAACCCACCAAGCCACCGTTCGAAAAGGAGTCGCTAATTTTCATCATGCATCACG
TCGTGTGGGGAAGAAAGAGAACAAATAAAATGTGTATTTATTTTCATTCATTTGGGATGTAGAAATTCTAGACTAC
AAACATCGTGATCGCATGATCTCAGGAGCCAAGAAAATTTTATTTTGAACCCAAAGTTGAAGCAAATTCAACCGTG
GACCTGGCGTTGTATCGAATCTCTGTTTGTGGTAGCTTGGATGTCCTTAGTGAACTAAGGCTGCGTAGCAAATCACT
GGANGTTGTGTGCGTTAAAAGGTAGTGGAGAAGTGCGTATGATATATATATATGTGTGTGTGTGTGTGTGTGTGTAT
GTTACAGTGTGAAAACCAATACATAGAGAAGTCAATTGTTGATCCCACATCAGATCACATCATTAGT RIPPT947 pPT947.seq (SEQ. ID. NO. 330)
CCCACAAACTCTTGGTGTTCCATCTCCTAGGGTTAGGGTTTTGGTTGTTTAGGTTTCCCTTTGTAGTTCAATAATAA
AAATTCCCTTGAGCCTCATTGTAGCACAATTCAAAGGCATGTGGCTGCCACATCACTTCTCAGAGATAAGCTACCAT
TGCCCGAGCTAGTTTATTTCCATCATGTGTGTAAGCATCTTTTAGTTCTTTGATATTAGTGAAATGAAGTTTTATTCC
TACTACATCTTTGTGTTTATGTTTATGTATGTATTTTATTTTGTTTCTACATAAGTCCAGATCAATAAACACGCACAC
ACACACACNCACACACACATTTGGTCCAATGGTTGGGCCTTGGGTCCAATATAACATTGGCATGTAACCATGAATT
AATTTCCACGCTATGAACCTTGATCACTTGGGGCTTACACATTGTCCATATGACTTTATCTTTGCAGGTAATTAACC
AGCCACATGGTGACATTAGCATTATGTCATCATGCCACATGATGGCTAGTGAAGANGTGCCACATGTCACCTGGAA
AACAAGTTGATTGGTCACTCGAGCTACCATTTGT RIPPT958 pPT958.seq (SEQ. ID. NO. 331)
ACATTGTANGATTGCAAAATGTGACTTTAGAGGATAGACATGAGTTTTTTCTAACAAGTCCAATCACCAACTATTAG
TGATTTTATACTTATCTTGGAGTCTCGAACACTGTGGGAACACACACACACACACACACACACACACACATATGTT
GGCATTATGGTGTGCAAGGATCCAACTANTTGATGTTGCCATTGGGATGATTGTGTTGGCATTGATGTGAACGATAT
GTTGGCATTGGGAAATGATGATTGCCACACTAGTTGATTGGGAACTAGGTCTTCANGCTTATGTTCGTGGAGATGAC
TTCTTGCGTGTTAGGTAAACTTGACTCAGGATANAGTCNAAGTTGACCANGTTAAACAGTGATGGTTTTGGGGCACA
TGGTATTGTGCGCCCATAGTATTCTGCCCATGGTATTATATGTAATGGGAGCTTATAAAAGGATGGAAGGACTTCNT
TGTCATGTATGCCTGCANGTGAGCGGTGAACGCTCACTTGGTCAGATTGGCTAGGGTTTTTGGCCANTGCTAATGAA RIPPT960 pPT960.seq (SEQ. ID. NO. 332)
ATCAACCCACTATCACAATCTTCCTTTTAATTATTCCTATCAAAGGTGTCCCACCACTTGCACCTAAGAAATAACAC
ATTTGAATGAAGATAAGTCCACTTGAAATTATATCTTGTATCTTTCCAACGTAACCTAATGTCCCCTGCATTATGTT TABLE 3-continued

| SSR loci |
| --- |
| TTGATCTTGGTGTCTAAACACGACTAGATTGGTCAAACTCGACTTCCACTCCATAGTCTTGTGTCATGCATCCATCTT CAGCATCCTTCACGCAACAATTATGTCCATATGCCCACATACATGGGAATAAATGCACCTATAAAAAAGTAAAAAA ATCATAGTGTCATGTGTCTAATAACCCAAACACACACACACACACACACACACACACACACACACAGATATATATG TTACATTTCAAAGGTGTCGTATGAAGTTAAAAATGT |
| RIPPT961 pPT961.seq (SEQ. ID. NO. 333) ATCAATCCACGAGGTCGATAAATTAAAATAACAATCCAAAATCATAAATAAGTAGCCCCCAAGAGTCCTCTTAATC TATATGAGCTCAAAGTCCATGGAACTATCAACCATTAGACAAGTGCGCATGCACACACACACACACACACACACAC ACACACACGCACACACACACACACACACACGCACACACACACACACACACACACACACACACACACACACACATA TATATCAAGGAGCTTGAGGGAGTATGCCCTCCTCCTCCTCAACATCTTTCTTATTCACTCTCTTTTTCTTCGGTTGG GGAAATTCCTTTTTCAATGCTCTTACCCACAACACCAACAAGATATTATTTTCTCCCCCTCTTCAGCTCCACATAGG TTTTTCCTTTTTGAGGAATCAACCAAGT |
| RIPPT968 pPT968.seq (SEQ. ID. NO. 334) ATCTTATGCTCACTTACTTTCTTACCACACTATGAAACCCAACCTAAAATCAATCATACTAACAGAATGCTCTACTA CCAAGCTAAATGAATCTTCATGAGGAATACCCTTAATAGGTCACTCTAAAGTATGGGTTGTTACCCCAACACCCCTT CCTAAGGCACACTTCGATTAAAGAATCATAAGCACCTTGAATCTTCTTAACACTAATTACAAAACTAGGATCAAAC CCAACCTAATACATATCATAAACTACTATAGATATCTACGACAAAACCACGTAGTGTTTCATACAATCCAACCTAA GCATGTGTGTGTGTGTGTGTGTGTGTGTGTGTGTGTGTGTGTGTGTGTGGATNACTACTTCCNAAGCTACATCCCATTC ACTTCTCANGGAAGATAAAAATATCNAAACCAACTTAATACCTACCATTTACTAATATAGATATATGCCACAAAGC CACATGCTNTTTTATAAAAACCACTCTAAAAAATTCAAAACCAACTTAGCAAGCTTNTCTATCGAGTATTANGGGG CGGGATTGANAGGCCAGTCCGATCTATGCTCTGCAGGGAATATCTTGAAACGTATTTCCTACCGACCACCCGAGCG TTCNGATCCCGAANTCAATGAAAACTNAATCA |
| RIPPT984 pPT984.seq (SEQ. ID. NO. 335) ACCACTTATAACATACCTTAACCACCTGCTAGTTTATTCCAACCTCTTGTTGGGTCCCAATTTCGTGTTAGAAACCC CTGGGAAACCTGTGACCTGAAAATTCCCCTTTCTATTAAAAATTTGTCTGATGAAATGCACATCTAACTGCATGCTA AAATGTAATACATGTGCATATGTATGTTCTAACATGATTATCTTATTTCAATTAACTTGTGTGTGTGTGTGTGTGTGT GTGTGTGTGTGTGTGTTGTNGCANTGGAATAAAGACAAATACTGCTCTTTTAATTTATGGAACTGGTTGCAAGCCTT TGACGTNTAACCTANCCAAAGACCATGTTGTTCATTTCCTTCAAGANCAAGCCACCCCCGAGTTGGGGCTTTGAGT CCATGGGGAATCAACAATAACTCTCCTAAAACCTANC |
| RIPPT990 pPT990.seq (SEQ. ID. NO. 336) ATCACTGGAAAGCTCTTAATGAGCTAAACACGATGGTAATTTTTTTTTAAAGTTTTGATGAGTTTGGAAAAAAGATG ATTTTTGCAACCCCATCTTCATAATAGATTGCGAGGGTAAGTTTAAGTTATAAGTAACACCCTCCACAACCCAAGAA TAACCCAAGCGGGCGGGAGCGACTATTACAAAATGGTATTAGAGAATGGTTCAACACTAGACCTAAAGAGGTTCAC GCGCACACGCACACACACACACACACACACACACACACACACACACACACACACACACACACTTAGGATAAACATGT TNGCTGCTATTTCCAATATTGTATACATATGAGGGTTGATTTTAAGTTACAAATGATATAATTGTTGACTTCNCNAA ATATTGATAAGTTATTTTATCCTTTAATCTGCATACTAACCCAAGATTTGATGATTTAGCTGGTTTCACATCNACAT GGTTATTGAAAACATGCCNAGATGATGGGTNNATATGTTTATNTACATTTTTATTTGATGAAGTGTTATGTGTGTGT GATAACACCTCAGAAGACACCANTGAAACGTCGAAAAAAATTCCNAAATGAA |
| RIPPT1013 pPT1013.seq (SEQ. ID. NO. 337) ACATCCCTGTGGGGATGAGTTATGTGTGTGTGTGTGTGTGTGTGTGTGTGTGTGTGTAAAAGCNAAANGCAAANATGTG TGTAAGGACTTCTANAGGTANACATANAACATTTGATGCTTAAGAGGCATAACNAATCACATGCTATANCAAACCA CATGCTAACAAAGATTAGTAACATATTAAGGAATAAACAGAACTCAATACATGTCATGGTCAAGCCNTGANAGGTT GGATCAAACTNGAAANATAGTGGGTTTTGAGAC |
| RIPPT1023 pPT1023.seq (SEQ. ID. NO. 338) ATCACGCTTGATCACTTAGCCTACTANGTTTGAGTTACTCGTCTCTTCCAATCCCTAATATTCTACCCTTATAGCTT AAGTAATATGTGAATTACTTGGGCCTTTCTACCCTCAGAGCATGGTCGCAATGGTTTTATTGTCCAAGGCTTTATTA CGACTTAGTGTCTGAGCCGTTATGTTATTGAGACTTAGCCTCCACTTGGTGCATATGCACATAAATATGCATAAGGC TTGAACCCGATGGATTTTCAAATGAAGTCAGCCTAGTCTTGGTTGTAGTGGTTTTGTTCCCAATTTGACCTAAGAAT AGTTTTATGAGGCCCCTTGGCCTCCAACCTACACACACACACACACACACACACACACACACACACATATAATTGT TAATCCTCCTGAGCTTACAGTTTGTAAACCAAGG |
| RIPPT1027 pPT1027.seq (SEQ. ID. NO. 339) CCTTAGATTCTAATCGTACTGTGTATAATACAAAAGCATGTGTTACAGTGTTGATTGTGTGCCAGTATGTATTTCAT ATATATGTGTGTGTGTGTGTTTGTGTGTGTGTGTGTGTGTGTGTGTTAATGGCTTGAANTCCTGTGTTTATAAGTGTA TTGATTGACCATCGATCACTGTAGCATCGATGGTGATCCAAAGATATTTGAGTTAACTGTTGTATGGAGTGATGGCA TGCTTAAACAGAGTGTTTCCAAATTGTGGCAGATCTGTGTTTTTAATGCAGAGATCCATCANAATGATCAANATTG ATTTAAGGAAGAAATGGACAAGAACACATAGAAACCGTCAGATCTGGAAGATCAATGTTCCANATCAAATCGCATG GAGCANAACCTTTTTATCACATCGGCAAAAATCCCNTGGGTGAT |
| RIPPT1035 pPT1035.seq (SEQ. ID. NO. 340) GCTCAACAGTTTTGTAAGTGTCGAGGCATATCTTTGCTATGGTCTTAGTCATTGGGATTTCAAAAACAAAACTACCC CATTTTCATTTTTGTCTGCATTTTTCCGTAATCTTGGTGTGCTAAACCAAGGGCATGCTGGTTTTGGAAACTTTATCC ATATTTGGTAACACAAACTCTCAAGAAAATACTGATTAAGGATGTCTAATACATAATGGAAGGTAACCCAAGACTC AGTGAACTAGCTTTGATTTTGAAAGCATAATGAGCCCTTCTCGTTACTCATAATTTATAAATTGGCAGGTGTGTGTG TGTGTGTGTGTGTGCGTGTACACATTACCATGCAAAGGAACGCCGATGACTTTAAATGGAGGCTAAGGTGTTTAACA NAGGGGAGTGTTGTGTTAAATGGGGGGGAGGGACACATATTCTTGATATGGAAGTGTGTGACACCTCTTCNAGATTT TGTGAGGAACAATGAATCTGAACAATGTCNTGANGATAAACTCGACNATAAAAAATGCCACAATGTAATAAAATGC ATTGGT |
| RIPPT1036 pPT1036.seq (SEQ. ID. NO. 341) CCTTGTTATATCTAGCTTCATCGAANGTGGTCGTTACCTCCTTACCCTCGAATACCTAGACTCAAGGTGTTAATTAA AAGGTAATTTAGTTAGAAACATAACCAAGCTAGCAAGAGGAGTAGCATCACTAGATATCCGAGACTTTGAACCTTG |

TABLE 3-continued

| SSR loci |
|---|
| GATTAACGAGAAACACACATAATTCTATATTTTTATGATACAAAGGTTTCTTTTCTTGCAGGTCAATAGAGTGCATG GTTGTGCGAGATCACAATATGTTTGCAACTATGCTAGATTAGTAGGAAGTTTTGAGATCATCGACAACCGTGTGTGT GTGTGTGTGTGTGTGTGTGTGTGTGTGTGTGTGTGTGTGTGTGTGTGTGTGCATTGTCCANTCAATTGGGTTTATTTT AGGTGGTTAGTTGTAGTGATTGGGATCCTCCCCACCCAATTTCAATTCCCTCAAGTGACATGATTAGCTTTGATATA ATGGTTTAGACCCTTGTTGTTGAGAATGAATANTCCCTAAGATTAACGGGAT |
| RIPPT1037 pPT1037.seq (SEQ. ID. NO. 342) ACAAATGCTCAATATAGACCACTTGCATCATATTTGTTTGTTGATCTAGATGAATGATGGTGCGCGCGCGCACACAC ACACACACACACACACACATGTATGAGATAGTTAACAANGTTGATGACAGGTTGATTATTCCTTTTGTTGAATTATG GCTATTTGATTGAGAGAATTTTGTTGAAGGATTTTAGTANTAAGATGTGTTGTTGAGTTAGAGTTGTATGAATGCTTA AGATTGAGAGTATGGATGAGGACAAAGTATGCTACTGCCAAATCATATGATGTTAACATTGATGTCTAAGTATATGT TGATGATGGAGAGTGATTTTGTGGTTTAATGCTGCTAGATTTTGTATTGCAGCAAGTTTTTGGAGTCTCGGTATAAA AGATAAGGGAAAAGAGAA |
| RIPPT1040 pPT1040.seq (SEQ. ID. NO. 343) ACATACATGTCATGTAGGCTTGAGGTGGATATGTCCAAAAGTCATGTCTCCTCAAGGAATTCATTGGAGCCACATGT GAATATATATGTGTGTGTGTGTGTGTGTGTGTGTGAGGTTATTAGACCATCCAAGAGAAACATTTCATAGAGAGATCAT CTCCAATGGTAGCCACAACACAAGAAGGAAGGGGTCGAGGAGAACAAGGGAAAATTTGAGGTATGTTTTATGGGTT TGATATGGCCAAAGTGTAGAAGAGGATAGCCAAGTGAATTATGGGCAGTAAGGTGCATATTTTAGGGTGTAATTCTC CTTGTTTTGGAGGGCCACAAGCTCTGTGGGACATGGTAGATACCGTGGGATTTTTTTGGGATTACTGGAGGGGTCAT AAGG |
| RIPPT1066 pPT1066.seq (SEQ. ID. NO. 344) ATCCTTAGTAACAGTTGTTCTCTGTTTACACAGAGAACATTGTGAAAACATGGGAAATTTCGTAGAAAACATAGCTC CTAGACTTGAAATTCTCATAACACCACTTTATAGTGCCATCGGGTCCGTCTATTGGTTGTCGTCGCTTATTGCAATG GCTCTTTCTCCTTCACATTTCGTTTAAGAAATGAAATTGTGAAAATACATTAAAAAGGGGGTGTTTGATGGATCTCG AGATCCATATAATATGGCTTGTAATATTATCGGGTCCAATCCATCGGATCACCCATATATATATATGTGTGTGTGTG TGTGTGTGTGTGTGTGTGTGTGTGTGTGNGCATGCATGTCTATCCCTGCTTTGNTGTGTTCGCTGATTTCGATCCGN CAATATCGGNGATCATGGTATCGNATCAGCATC |
| RIPPT1072 pPT1072.seq (SEQ. ID. NO. 345) ATCACCTAGTCTGCCCCTAGTGTGATGTTTCTTATCTCCAAAGAGTCTTCCTTGTAAACGAGACTCACAAAGTGAAT TTTTTCACTCTTTATTTACTAATTTGAAGTTTTCATGACCTTGGAGTGGATTCACACACACACACACACACACACA CACACATATTTTTTTACAAAATGTTAATATTTTATGTATTTTTTGGTTGACTAGTCCAGTTTTGATGACATTGTTGAG GAAGTTGTGACTGTTATTGCGAAATATAACATCGCAGTGCAAAGTTCACTAAGCACTCTAGAATAGGAGCAACAAT GGGATCAATCACCAGTGTAAGCGTAGCAACCATTCCCCCGCTATTCTGTGGTTGGATATTATCCCCACAAGGGAGT CTTCCCTAGTAGAATTTAGGGACTATATAATGTTAAGCCCTTAATAAGCCTCATGTTACCCATAAACCTCTTATTAA GCCCTAGATATTGAGTGATTACTTATCTATTGGTATATTGGTATGTAGGCTATAACCCCTCATGGT |
| RIPPT1076 pPT1076.seq (SEQ. ID. NO. 346) GCTAGCATGTAAATGTGTAAACCCAGGCTAGGCTGAGGCACATTTAAGCATAGGAGGGATAACACTCGTTTGTATCT TTATACATAATATGTGCGTGTGTGTGTGTGTGTGTGTGTGTGTGTGTGTGTGTGTGTGTGTGTGTGTGTGTGCAGGCTAC AGTTNGAGGGGCTTTGTGAAATCATATGTATGACAAGCCAAATTTTGGAGTAAGACCCCAAATTCATACCAATAAC CACTACATCTAATACTTGGACTAANTCCNTCGAAAAACCACTGGGTTCAAGCCTTATGCATATCTATGTGCATATGC ATCAATCGGGGGTNGAGTCTCTGTTGGCATTATGGCATATGTTNGATGCTATGGCTCTGGTGTTGTCCTNGATGGCA ACTCAACTTGGTGACAAATCCCAGATCAGGCACCCAGAAAGAAGAAAAAGTCATATACGCNGGTTCATCTANACAA AGACGTGT |
| RIPPT1077 pPT1077.seq (SEQ. ID. NO. 347) ATCTCTCTTCGTTGGGCATATTTCCTACCATAAATCACAGCCCAAGTCTATGACCTACTGTAACATTCTAGCATGCC CCACATATTTTTATCAAACACAGGTCTCGCAATACATCTAATTACAGATTAAGGAATTGGATTACATTTTGCCATGA AGTGGAAAATTTTACTTTGTTCACCGCACAATAGTCATATTCAAATTCTTACCTTCCTTTTGTGTGTGTGTGTGTGTG TGTGTGTGTGTGTATATATATATATATAAAGAGGAGAGACATCCACCACAAAGAAACTATTGGATTTCCTCTTAGAACT TAAAAAAAAAAACATTAACAATTTCAATTAAGGACAAAGAGAAATAATTTTTCTTTTTTGCCACACCTATTGAAAAT AGAAACAAGAAAATGCTAAAAATAGAAGTGCTAAAAATAACACTTCTATAAATCGCAATTTGGGT |
| RIPPT1125 pPT1126.seq (SEQ. ID. NO. 348) CCTTGTGAGGCTAAAAAGGAGAAGAGGAATTTTTTTTTATGGTGTTGTGGAGAAGAGAATTTGAGAAAGGATTGTCC CTGAAGGAAGAAGATGAAATAAGTTAGCCACTATGAGCCACACAAACATGCATCAACGATGCAGGATGTTGAGAAN GAGGACGGGGCTTCCCCTCAAGCTCCTTCACACACACACACACACACACACACACACACACACACACACACACACAC ACACACACACACACACACACACACATATACATATTTGTGTGTGTGTGTGTCGAAAATATCCCTCGTGAACTTTTGGG AAATGTAAGACTTCNAGGTTATTGTGAGCCTTGTGAANAANTCTTGATGTGATTTTGGTATATGATTATGCGTATGT |
| RIPPT1137 pPT1137.seq (SEQ. ID. NO. 349) ACAATCACTCCTGTATTAATTAGAAGAGTCAAAATTCTCTTAAGCAATGTATCTATCTATCTATCTATCTATCTATC TATATATATATATCCAAAAATTCCTCAGCAATTGATCCCTACAAATGAGGCATGAGGGTGAAGCTTATCACAATGCA CAAAGAGAAGGCAAGATTTACCTTGGGAAAACCCACTAAGGGGAAAAAACTAACAACCTTTTCAATAGAGAAATGC TTTTGTTCAACAAGGGACACACCTAGACCCTTCTAGTCATTAAATAGTTCACACTTGGTCAAACCATCTAAGTCAAG CCTCCCAATCTAATCCAACACTTGGCATTTACAGATCTACCCAAAATTTCAACCCTCTTGCAACTGCTAGATTCCCA AAATTTCGGCCCCATGCAACTGCCTAGAATTTCAGCACCTACAATGGAAACTGCTCATAAATATGTGAACTATCGAT AGATAGATAGATAGAGATAGATAGATAGATAGATAGATAGATAGAGAGAGAGAGAGAGAGAGAGAGAGAGAGAGAGAG AGAGTATCCCACGTGCGAGCTTGAGAGAGAGAGAGAAATAGAGATGCCANT |
| RIPPT9058 lobseq3-11-97clone249 (SEQ. ID. NO. 350) CCCGCTCCTATTCAAGATCAAAAGAAGGATATGTTAAAGGTCAAGTGCTTCATTTGTCAAAACTTTGGACACTATGC ATCAACAACCAATGTTGTTGTTGATGATGATGATGATGATGAGCATCCACCTCAAAAGAAGTCAAAGGAATTCTTCC TTTAGGAGCTACTACCAATAATGCTTGAGGGTAATTATGCCTCTAGGCGCCTGATCGGTTTCCAAGATTCTCTTATA |

TABLE 3-continued

| SSR loci |
|---|
| GGTTTTTAGGGARGGAGTTGACAATCCTCAACAATTTCTTCCTTAATCAACAGATAAGTATGTCATATTTTTCTCTT GATTATT |
| RIPPT9104 lobseq3-7-97ATCclone71 (SEQ. ID. NO. 351) CCTTTCTGAATGACAAAAGGGCTTCTACGNCCTTCCTATCGTCAGCGTCCATGGATGATGATGATGATGNAAATTCA GGNTGCTCCACAGTGCCTTCATCGTCCTTCAAAAGAGATTGAAGAGAAGCACTTCCACCAGTCGTGCGCTCATACA GATGATCATGGTGTAAAGCATGACCCCTGTGAACATGNGAGTAATGATATGGCTTCATGGAATAACTAATAGTTGCC AGGAGAAGAAGCCACACTAGTATGATTATCGACACAGCACTTTTCTCCTTTCTCTCTTTATCTCAATTCGAAAGAAN TCNAAGANTGGCCTGTGATTNCCTTGTTTGCGGGCNCC |
| RIPPT9138 lobseq5-2-97ATC187 (SEQ. ID. NO. 352) ATTGAAACCAATTTTTCCCCTTTTTAATGTAAAAAATATCAAAATAAATAACAAATTATATAATAATTCATTATAAA ACAATATAAATTTTAACATATATATGAACTTTGAAATAAACCTTAATGGTGATGATGATGATGATGGTGGTGGTTAA CGTCCACTGAGACCAAATTGGTCTATCGGACCTATAATTTCTTAGTTTTTACTTATCTGGCTCCTTGTCTTTCTTGGC GAGATTAGTGTTGTAGCTTTCTTTTTTTTCTCTACAGTCTTCCAACTTCCTTTATCTTGCATCTCCCTCCACTCCTCT CGTTCCTTGGGAAATTGGTGTCTNACTTCCCAANCCATNGTGTTTCATCCTTTGAAGG |
| RIPPT9238 lobseq8-19-97TTC2D1 (SEQ. ID. NO. 353) CCCTGAGACATCCAATCCATGTGTTTTTCTACCATTTATTTATCATTTTATTTTCCTTCTTCTTCATAATTTGATTAG TCTTCTTCTTCTTCTTCTTCTCCGCCCAACTCATGTAAAGTATCATCTAAGAGCACTACATTATCACCATCACCATC ATTTAAGGTTGAAGGTTTTTCTAGTTTTTCTATATTTTATTTAGAGTCTAACTATTCAAGGGTGGTAAGAACCAACTC TTCAACTGTTGACACCATTATCCTANTGGGGGTGGTTTGGTTCTNATTCACAAAATACGGAAAAGTTTCTATTCTGG ATCCTTTAGA |
| RIPPT9315 lobseq12-4-97AC1-G8 (SEQ. ID. NO. 354) CCTCTTCCTAGTAGGGGGATTACTTGGAGGAGGATCCGAGGGGTCCATAGGGTCCATGCGATCATCATCAACCTCC TTTTTCGGCTTAGGCATAGAGGGACCCTCTAGTAGGTCCATAGCATTATCTTTTTTCTAGTAGGTCTCTAGCTAATC CAAAGGAAACATATCCATCGAAAGTTACATCCTTGATAAACTCGATCTTCCTTTTGCTATATGTGTGTGTGTGTGTG TGTGTGTGTGATTTAGAGTTTTCACAATATCCAACAAACATATCTTTCTTTATGGTGGCTTCCAACTTGTTCCTCTTG TCCTTCNGCACATGGAAATATACGGGACAACCAAATATCAT |

The PIC and H values are presented in Table 4 for the 18 polymorphic loci amplified from the first 89 primer pairs that were synthesized.

TABLE 4

Allelic diversity data for SSR loci in 20 *Pinus taeda* trees

| RIPPT locus | SSR repeat in cloned allele | # alleles | allele size range, bp | PIC | H |
|---|---|---|---|---|---|
| 1 | $(A)_6$ . . . $(ATG)_7$ (SEQ ID NO:390) | 4 | 199–260 | 0.297 | 0.331 |
| 6 | $(ATG)_6$ . . . $(C)_6$ (SEQ ID NO:391) | 17 | 273–315 | 0.892 | 0.949 |
| 11 | $(CAT)_6$ . . . $(A)_6$ (SEQ ID NO:392) | 3 | 156–169 | 0.427 | 0.542 |
| 22 | $(ACC)_6(ATC)_4$ (SEQ ID NO:355) | 3 | 243–249 | 0.368 | 0.426 |
| 24 | $(TTG)_4(TC)_2$ $(TTA)_{12}$ (SEQ ID NO:356) | 3 | 146–152 | 0.282 | 0.320 |
| 31 | $(C)_5$ . . . $(ATT)_{19}$ (SEQ ID NO:393) | 15 | 225–267 | 0.859 | 0.916 |
| 32 | $(TAT)_7$ . . . $(A)_5$ (SEQ ID NO:394) | 6 | 173–189 | 0.586 | 0.653 |
| 33 | $(TAT)_8$ (SEQ ID NO:357) | 3 | 169–178 | 0.410 | 0.484 |
| 64 | $(A)_6C(A)_5(AAAC)_5$ $(A)_5$ (SEQ ID NO:358) | 11 | 233–261 | 0.751 | 0.818 |
| 65 | $(AAAC)_5(A)_7$ (SEQ ID NO:359) | 9 | 130–139 | 0.816 | 0.879 |
| 66 | $(AAAT)_8$ (SEQ ID NO:360) | 3 | 98–110 | 0.577 | 0.685 |
| 67 | $(AAAT)_4$ (SEQ ID NO:361) | 3 | 217–225 | 0.340 | 0.392 |
| 69 | $(AAAT)_4$ (SEQ ID NO:362) | 2 | 140–148 | 0.319 | 0.420 |
| 71 | $(AAAT)_{11}$ (SEQ ID NO:363) | 14 | 219–260 | 0.853 | 0.917 |
| 77 | $(ATT)_{11}$ (SEQ ID NO:364) | 5 | 154–180, null | 0.581 | 0.691 |
| 79 | $(ATT)_{12}$ (SEQ ID NO:365) | 8 | 130–161 | 0.723 | 0.765 |
| 80 | $(ATT)_7$ (SEQ ID NO:395) . . . $(AAT)_6$ (SEQ ID NO:396) | 4 | 247–263, null | 0.438 | 0.525 |
| 89 | $(TTC)_{10}$ (SEQ ID NO:397) . . . $(T)_5$ | 3 | 220–223 | 0.327 | 0.386 |
| mean | | 6.4 | | 0.547 | 0.617 |

null - PCR amplification could not be observed in one or more samples from trees that were assumed to be homozygous for a "null" allele.

Referring to Table 4, most loci had stepwise allele size differences, i.e., the minimum size differences were multiples of the unit length of the major repeat motif. Loci RIPPT1, RIPPT6, RIPPT32, RIPPT64, RIPPT65, RIPPT71, and RIPPT80, however, had minimum size differences among some alleles of a single base pair. For all these loci, except RIPPT71, the 1 bp allele size differences may have originated in short, mutable mononucleotide stretches found near or adjacent to the target SSR and included in the PCR amplified region. The RIPPT71 locus had no repeats other than $(AAAT)_n$.

SSR Markers in Other Pines

The results of testing *P. taeda* SSR primer pairs for amplification of marker loci in other pine species are presented in Tables 5 and 6. Table 5 includes individual species results for RIPPT1 through RIPPT90, while Table 6 is a summary of success of amplification of single loci patterns in other species for all RIPPT primer pairs. As described above, polymorphism among species was scored from high resolution agarose gels, so the number of polymorphic SSR loci amplified among species may have been underestimated. Details of the agarose gel marker phenotypes are given only for the 49 primer pairs that amplified single loci in *P. taeda* among RIPPT1 through RIPPT90 (Table 5).

TABLE 5

SSR marker phenotypes among various pine species, using primer pairs that amplified single loci in *P. taeda*.

| Locus (SSR motif) | marker size (bp) | *P. caribaea* | *P. ponderosa* | *P. radiata* | *P. resinosa* | *P. strobus* | *P. sylvestris* | PAS |
|---|---|---|---|---|---|---|---|---|
| RIPPT1* (ATC) | 260 | –[d] | (+)[e] | (+) | – | (+) | (+) | y |
| RIPPT2 (ATC) | 185 | – | (+) | (+) | (+) | (+) | (+) | y |
| RIPPT4 (ATC) | 145 | – | – | – | – | – | – | n |
| RIPPT6* (ATC) | 290 | – | 3[f] | 1 | 1(+) | 1(+) | 2 | y |
| RIPPT7 (ATC) | 105 | 1 | 4 | 1 | 2 | 1 | 2 | y |
| RIPPT9 (ATC) | 120 | 1 | 1(+) | 1 | 1 | (+) | 1 | y |
| RIPPT11* (ATC) | 170 | 1 | (+) | (+) | 1(+) | (+) | 1(+) | y |
| RIPPT13 (ATC) | 105 | 2 | 1 | 2 | 3 | 1 | 3 | y |
| RIPPT16 (ATC) | 220 | 1 | 1 | 1 | 1 | 1 | 1 | n |
| RIPPT19 (ATC) | 105 | 1 | 2 | 1 | 1 | 1 | 2 | n |
| RIPPT20 (ATC) | 110 | 1 | 1 | 1 | 1 | – | 1 | n |
| RIPPT21 (ATC) | 185 | – | 1 | 1 | 1 | 1(+) | 1 | n |
| RIPPT22* (ACC) | 245 | – | 1 | 1 | 1 | – | 1 | y |
| RIPPT24* (AAT) | 150 | 1 | 1 | – | 1 | – | – | y |
| RIPPT26 (AAT) | 190 | 1 | 2 | 1 | 1 | 1 | 1 | n |
| RIPPT27 (AAT) | 130 | 1 | 1 | 2 | – | 1 | – | y |
| RIPPT29 (AAT) | 210 | – | 2 | 1 | (+) | 1(+) | 1(+) | y |
| RIPPT30 (AAT) | 215 | 1 | 1(+) | 1 | 1(+) | 1(+) | 1(+) | y |
| RIPPT31* (AAT) | 245 | 1 | 1 | 1 | 2 | (+) | 2 | y |
| RIPPT32* (AAT) | 180 | 1 | 1 | 1 | 1 | 1 | 1 | y |
| RIPPT33* (AAT) | 170 | – | 1 | 1 | 1 | – | 1 | y |
| RIPPT35 (AAC) | 270 | – | 1 | 1(+) | 1(+) | 2 | 1 | n |
| RIPPT37 (AAC) | 110 | 1 | 1 | 1 | 2 | 1 | 2 | y |
| RIPPT38 (AAC) | 270 | 1 | 1 | 1 | 1 | 1 | 1 | n |
| RIPPT40 (AAC) | 190 | 1 | 1 | 1 | 1 | 1 | 1 | n |
| RIPPT42 (AAC) | 230 | 1 | 1 | 1 | 1 | 1 | 1 | y |
| RIPPT43 (AAC) | 145 | 1 | 1 | 1 | 1 | 1 | 1 | y |
| RIPPT44 (AAC) | 210 | 1 | 1 | 1 | 1 | 1(+) | 1 | n |
| RIPPT51 (AAG) | 260 | 1 | 1 | 1 | 1 | 1 | 1 | n |
| RIPPT52 (AAG) | | 1 | 1 | 1 | 1 | – | 1 | n |
| RIPPT54 (AAG) | 175 | 1 | 1 | 1 | 1 | 1 | 1 | n |
| RIPPT56 (AAG) | 390 | – | – | – | – | 2 | 2 | y |
| RIPPT58 (AAG) | 235 | 1 | 1 | 1 | 1 | – | – | y |
| RIPPT64* (AAAC) | 345 | – | 1 | 2 | 1 | (+) | 1 | y |
| RIPPT65* (AAAC) | 135 | – | 1 | – | 1 | – | – | y |
| RIPPT66* (AAAT) | 105 | 1 | 1 | 1 | 1 | 1 | – | y |
| RIPPT67* (AAAT) | 220 | – | 1 | 1 | 1 | 2 | 1 | y |
| RIPPT69* (AAAT) | 145 | – | 1 | 1 | 1 | 2 | 1 | y |
| RIPPT71* (AAAT) | 240 | 1 | 3 | 1 | 1 | 2 | 1 | y |
| RIPPT74 (AAT) | 130 | 1 | 1 | 2 | (+) | – | – | n |
| RIPPT75 (AAT) | 205 | 1 | 1 | 1 | 1(+) | – | 1 | y |
| RIPPT77 (AAT) | 175 | 1 | 3 | 1 | 3(+) | 3(+) | 2 | y |
| RIPPT78 (AAT) | 220 | 1 | 1 | 1 | 2 | – | 1 | y |
| RIPPT79* (AAT) | 155 | 2 | 1 | 1 | 1 | – | 1 | y |
| RIPPT80* (AAT) | 250 | 2(+) | 3 | (+) | 1 | 1 | (+) | y |
| RIPPT86 (ACC) | 260 | 1 | 2 | – | (+) | – | – | y |
| RIPPT88 (AAG) | 235 | 1 | 1(+) | – | (+) | (+) | (+) | y |
| RIPPT89* (AAG) | 225 | 1 | 1(+) | – | 1 | (+) | 1(+) | y |
| RIPPT90 (AAC) | 150 | 2 | 1 | 1 | 1 | (+) | 1(+) | y |

bp = approximate allele size for *P. taeda* tree 7–56.
PAS = Polymorphic Among Species
*= an asterix indicates that the locus was polymorphic in *P. taeda*
(–) = a dash indicates that no PCR amplification was observed.
(+) = indicateds that one or more fragments were amplified outside of the expected size range, which is ±100 bp from the marker size in *P. taeda*.
[f]integers indicate the number of PCR fragments observed in the expected size range.

TABLE 6

Summary of *P. taeda* SSR primer pairs in other pine species

| | *P. caribaea* | *P. ponderosa* | *P. radiata* | *P. resinosa* | *P. strobus* | *P. sylvestris* |
|---|---|---|---|---|---|---|
| # primer pairs tested | 566 | 118 | 498 | 119 | 566 | 566 |
| # amplifying single locus | 168 | 47 | 127 | 38 | 84 | 138 |

The 54 unique loci that were polymorphic in *P. taeda* were also polymorphic among species, but the primer pairs did not always amplify just one locus in the other pine species. The frequency of PCR amplification was lowest in *P. strobus* (eastern white pine). This was expected, because of the species examined is the most distantly related to *P. taeda*, and is the only species examined from the Strobus subgenus. AR other species, including *P. taeda*, are classified in the Pinus subgenus (Little and Critchfield 1969, Subdivisions of the genus Pinus (Pines) (USDA Forest Service, Misc. Pub. 1144).

For all single RIPPT loci, 12 were monomorphic in *P. taeda*, but were polymorphic among species (Table 7). Loci that are monomorphic within a species but polymorphic between species may be useful as species-specific markers.

TABLE 7

Marker information for SSR loci that were monomorphic within *P. taeda*, but polymorphic among seven pine species.

| Locus | forward and reverse primer sequences | | SSR sequence | allele size *P. taeda* 7–56 |
|---|---|---|---|---|
| RIPPT2 | CCCTAGGGAAAGGTTTCCAC<br>GGTCCCATAGACCAATTTGG | (SEQ ID NO:366)<br>(SEQ ID NO:367) | $(ATG)_7$ | 188 |
| RIPPT7 | GATCAATCATCAAATTCATCACC<br>GTTGCAGATGAGGCTAAGGC | (SEQ ID NO:368)<br>(SEQ ID NO:369) | $(CAT)_6$ | 113 |
| RIPPT9 | CCAATTTGGTCTCAGTGGATG<br>GAGATGCCCCTAGGTTCTCC | (SEQ ID NO:370)<br>(SEQ ID NO:371) | $(ATC)_6$ | 125 |
| RIPPT27 | TCCACAGCCATCACCACTTA<br>TGGGTCCGATAGACCAATGT | (SEQ ID NO:372)<br>(SEQ ID NO:373) | $(ATT)_6(GAT)_6$ | 132 |
| RIPPT29 | TAAGGTTTCACCAAGGGCTG<br>TCATGGGGTCAATTCTCCTC | (SEQ ID NO:374)<br>(SEQ ID NO:375) | $(ATT)_{15}$ | 189 |
| RIPPT30 | ATGGATGGAAAATTTCTATAGCC<br>ATGTTTCCAATTAAAGGATTTCC | (SEQ ID NO:376)<br>(SEQ ID NO:377) | $(ATT)_{13}$ | 236 |
| RIPPT58 | GCCTTGCAAAGTGACCTCTC<br>TCCATGACAACCCAGTTCAA | (SEQ ID NO:378)<br>(SEQ ID NO:379) | $(AGG)_4$ | 240 |
| RIPPT81 | GAGAACGCGCGACTGTATTA<br>TTTCCCATCTGGTTCATGTG | (SEQ ID NO:380)<br>(SEQ ID NO:381) | $(ATT)_4$ . . .<br>$(ATT)_5$ . . .<br>$(ATT)^9$ | 178 |
| RIPPT86 | CCAATTCTTTGAAGTATTATAG<br>GATCGCGAAGCTAAGACACC | (SEQ ID NO:382)<br>(SEQ ID NO:383) | $(ATG)_5(GTG)_7$ | 262 |
| RIPPT90 | TCGATCACAGTGTTGGCATT<br>GCCAAGCCCATTCAGTTTA | (SEQ ID NO:384)<br>(SEQ ID NO:385) | $(TTG)_7$ | 150 |
| RIPPT314 | AGAGGTTGCAGGAAGCAAAA<br>ATTGGTTTCTCCATCGTTGC | (SEQ ID NO:386)<br>(SEQ ID NO:387) | $(GAA)_4$ | 142 |
| RIPPT914<br>1 | AGGCGAAGCTTATGGAACAA<br>TGTTTCCCGATCCTCTGTTC | (SEQ ID NO:388)<br>(SEQ ID NO:389) | $(GAT)_4$ | 143 |

What is claimed is:

1. An isolated polynucleotide consiting of SEQ ID NO: 246.

2. An isolated polynucleotide that hybridizes under stringent conditions to the polynucleotide of claim 1, wherein said polynucleotide comprises at least one SSR motif.

3. The isolated polynucleotide of claim 2, wherein said polynucleotide is a maximum of about 500 nucleotides long.

4. An isolated polynucleotide having at least about 85% homology to SEQ ID NO: 246, wherein said polynucleotide comprises at least one SSR motif.

5. An isolated polynucleotide having at least about 85% identity to SEQ ID NO: 246, wherein said polynucleotide comprises at least one SSR motif.

6. An isolated polynucleotide comprising a SSR motif and having the property of being amplifiable from a genomic DNA using PCR and two primers, wherein the first primer consists of SEQ ID NO: 19 and the second primer consists of SEQ ID NO: 20.

7. The polynucleotide of claim 6 wherein said genoinic DNA is from a pine.

8. The polynucleotide of claim 6 wherein said genomic DNA is from a species of the Pinus subgenus.

9. The polynucleotide of claim 7, wherein said pine is selected from the group of *P. taeda, P. caribaea, P. pcrnderosa, P. radiata, P. resinosa, P. strobus*, and *P. sylvestris.*

10. The isolated polynucleotide of claim 6, wherein said polynucleotide is a maximum of about 500 nucleotides long.

11. The isolated polynucleotide of claim 6, wherein said SSR motif is selected from the group consisting of AC, AAC, AAG, AAT, ACC, ACG, AGG, ATC, AAAC, AAAT, AGAT, and all complements and permutations of said motif.

12. The isolated polynucleotide of claim 6, wherein said SSR motif forms a compound repeat, which may be perfect or otherwise, selected from the group consisting of: (A)n . . . (ATG)n; (ATG)n . . . (C)n; (CAT)n . . . (A)n; (ACC)n . . . (ATC)n; (TTG)n . . . (TTA)n; (C)n . . . (ATT)n; (TAT)n . . . (A)n; (ATT)n . . . (AAT)n; (TTC)n . . . (T)n; and (A)n (AAAC)n(A)n.

13. A method of detecting the presence of a SSR locus comprising a SSR motif of the sequence (N1, N2 . . . Ni)n, wherein: N represents nucleotides A, T, C or G; i represents the total number of the nucleotides in the SSR motif; and n represents the number of times the SSR motif is repeated in the SSR locus; said method comprising the steps of:

(i) isolating genomic DNA from a subject;

(ii) analysing the isolated genomic DNA for the presense of said SSR motif by using the polynucleotide of claim 1.

14. The method of claim 13, wherein said step (ii) comprises:

(a) amplifying DNA molecules from the genomic DNA by polymerase chain reaction;

(b) resolving the amplified DNA molecules by electrophoresis;

(c) detecting the amplified DNA molecule.

15. The method of claim 13, wherein said SSR motif is selected from the group consisting of AC, AAC, AAG, AAT, ACC, ACG, AGG, ATC, AAAC, AAAT, AGAT, and all complements and permutations of said motif.

16. The method of claim 13, wherein said SSR motif forms a compound repeat, which may be perfect or otherwise, selected from the group consisting of: (A)n . . . (ATG)n; (ATG)n . . . (C)n; (CAT)n . . . (A)n; (ACC)n . . . (ATC)n; (TTG)n . . . (TTA)n; (C)n . . . (ATT)n; (TAT)n . . . (A)n; (ATT)n . . . (AAT)n; (TTC)n . . . (T)n; and (A)n (AAAC)n(A)n.

17. The method of claim 13, wherein said subject is a plant.

18. The method of claim 17, wherein said plant is a pine.

19. The method of claim 18, wherein said pine is selected from the group of *P. taeda, P. caribaea, P. ponderosa, P. radiata, P. resinosa, P. strobus*, and *P. sylvestris.*

20. A method of genetic characterization of an individual comprising determining the presence of a SSR locus, said locus comprising a SSR motif of the sequence (N1, N2 . . . Ni)n, wherein N represents nucleotides A, T, C, or G, i represents the number of the last nucleotide in the SSR motif, and nrepresents the number of repeats of the SSR motif present in the SSR locus; said method comprising the step of comparing the SSR locus of said individual with the polynucleotide of claim 1.

21. The method of claim 20, wherein said genetic characterization is a genetic mapping study.

22. The method of claim 20, wherein said genetic characterization is a population genetics study.

23. The method of claim 20, wherein said genetic characterization is an inheritance study of a commercially important trait in a plant breeding program.

* * * * *

SEQUENCE LISTING

<160> NUMBER OF SEQ ID NOS: 397

<210> SEQ ID NO 1
<211> LENGTH: 19
<212> TYPE: DNA
<213> ORGANISM: Pinus taeda L.

-continued

```
<400> SEQUENCE: 1

gcatgccaaa agatctcaa                                                   19


<210> SEQ ID NO 2
<211> LENGTH: 20
<212> TYPE: DNA
<213> ORGANISM: Pinus taeda L.

<400> SEQUENCE: 2

agtgaactcg ggaggcttct                                                  20


<210> SEQ ID NO 3
<211> LENGTH: 20
<212> TYPE: DNA
<213> ORGANISM: Pinus taeda L.

<400> SEQUENCE: 3

tttggacaag tggcttgttg                                                  20


<210> SEQ ID NO 4
<211> LENGTH: 20
<212> TYPE: DNA
<213> ORGANISM: Pinus taeda L.

<400> SEQUENCE: 4

atgtttgatt gcatggggat                                                  20


<210> SEQ ID NO 5
<211> LENGTH: 21
<212> TYPE: DNA
<213> ORGANISM: Pinus taeda L.

<400> SEQUENCE: 5

ggcttctctc caagcttttt g                                                21


<210> SEQ ID NO 6
<211> LENGTH: 20
<212> TYPE: DNA
<213> ORGANISM: Pinus taeda L.

<400> SEQUENCE: 6

gaatgagcct cccaactcaa                                                  20


<210> SEQ ID NO 7
<211> LENGTH: 23
<212> TYPE: DNA
<213> ORGANISM: Pinus taeda L.

<400> SEQUENCE: 7

ctcagtttca taatctttgt cgc                                              23


<210> SEQ ID NO 8
<211> LENGTH: 24
<212> TYPE: DNA
<213> ORGANISM: Pinus taeda L.

<400> SEQUENCE: 8

ttttagaaaa gaaggaaatc ttca                                             24


<210> SEQ ID NO 9
<211> LENGTH: 20
<212> TYPE: DNA
<213> ORGANISM: Pinus taeda L.
```

<400> SEQUENCE: 9
gacaccggat actgaggtgg 20

<210> SEQ ID NO 10
<211> LENGTH: 20
<212> TYPE: DNA
<213> ORGANISM: Pinus taeda L.

<400> SEQUENCE: 10
cccgcaactt cgtaagagtc 20

<210> SEQ ID NO 11
<211> LENGTH: 20
<212> TYPE: DNA
<213> ORGANISM: Pinus taeda L.

<400> SEQUENCE: 11
ccaaccaatg tggttcatca 20

<210> SEQ ID NO 12
<211> LENGTH: 24
<212> TYPE: DNA
<213> ORGANISM: Pinus taeda L.

<400> SEQUENCE: 12
aggaaaatag aagggaataa gacc 24

<210> SEQ ID NO 13
<211> LENGTH: 20
<212> TYPE: DNA
<213> ORGANISM: Pinus taeda L.

<400> SEQUENCE: 13
tagcaggtta caacctgggg 20

<210> SEQ ID NO 14
<211> LENGTH: 20
<212> TYPE: DNA
<213> ORGANISM: Pinus taeda L.

<400> SEQUENCE: 14
agcccaattg atgggaaatt 20

<210> SEQ ID NO 15
<211> LENGTH: 20
<212> TYPE: DNA
<213> ORGANISM: Pinus taeda L.

<400> SEQUENCE: 15
ttggagaaca tgcttgcaag 20

<210> SEQ ID NO 16
<211> LENGTH: 20
<212> TYPE: DNA
<213> ORGANISM: Pinus taeda L.

<400> SEQUENCE: 16
tggagcattt tccacaaaat 20

<210> SEQ ID NO 17
<211> LENGTH: 20
<212> TYPE: DNA

-continued

```
<213> ORGANISM: Pinus taeda L.

<400> SEQUENCE: 17

gcagcgtaat cagatggtca                                                   20


<210> SEQ ID NO 18
<211> LENGTH: 20
<212> TYPE: DNA
<213> ORGANISM: Pinus taeda L.

<400> SEQUENCE: 18

cggaaggcga gttgaagata                                                   20


<210> SEQ ID NO 19
<211> LENGTH: 20
<212> TYPE: DNA
<213> ORGANISM: Pinus taeda L.

<400> SEQUENCE: 19

ccaacagcac ttacccaaaa                                                   20


<210> SEQ ID NO 20
<211> LENGTH: 20
<212> TYPE: DNA
<213> ORGANISM: Pinus taeda L.

<400> SEQUENCE: 20

agcctcatga aagcccagta                                                   20


<210> SEQ ID NO 21
<211> LENGTH: 23
<212> TYPE: DNA
<213> ORGANISM: Pinus taeda L.

<400> SEQUENCE: 21

gttgatagag tttcatgtgg tgc                                               23


<210> SEQ ID NO 22
<211> LENGTH: 23
<212> TYPE: DNA
<213> ORGANISM: Pinus taeda L.

<400> SEQUENCE: 22

tggatgaaga attttgtagt caa                                               23


<210> SEQ ID NO 23
<211> LENGTH: 20
<212> TYPE: DNA
<213> ORGANISM: Pinus taeda L.

<400> SEQUENCE: 23

agccctccaa gaccaagatt                                                   20


<210> SEQ ID NO 24
<211> LENGTH: 20
<212> TYPE: DNA
<213> ORGANISM: Pinus taeda L.

<400> SEQUENCE: 24

ccatttgcaa ataccccaac                                                   20


<210> SEQ ID NO 25
<211> LENGTH: 20
```

-continued

<212> TYPE: DNA
<213> ORGANISM: Pinus taeda L.

<400> SEQUENCE: 25
tcaagaatgg gggatgattc 20

<210> SEQ ID NO 26
<211> LENGTH: 20
<212> TYPE: DNA
<213> ORGANISM: Pinus taeda L.

<400> SEQUENCE: 26
ttgcatccaa caactgcttc 20

<210> SEQ ID NO 27
<211> LENGTH: 20
<212> TYPE: DNA
<213> ORGANISM: Pinus taeda L.

<400> SEQUENCE: 27
ctactcaaag tgcttgggca 20

<210> SEQ ID NO 28
<211> LENGTH: 20
<212> TYPE: DNA
<213> ORGANISM: Pinus taeda L.

<400> SEQUENCE: 28
ccccttccct ttctatctgc 20

<210> SEQ ID NO 29
<211> LENGTH: 20
<212> TYPE: DNA
<213> ORGANISM: Pinus taeda L.

<400> SEQUENCE: 29
acaccggata ctgaggtgga 20

<210> SEQ ID NO 30
<211> LENGTH: 20
<212> TYPE: DNA
<213> ORGANISM: Pinus taeda L.

<400> SEQUENCE: 30
ggttgtagcc tcccgtaggt 20

<210> SEQ ID NO 31
<211> LENGTH: 20
<212> TYPE: DNA
<213> ORGANISM: Pinus taeda L.

<400> SEQUENCE: 31
tgatttgatc cctctaggcg 20

<210> SEQ ID NO 32
<211> LENGTH: 27
<212> TYPE: DNA
<213> ORGANISM: Pinus taeda L.

<400> SEQUENCE: 32
aatcttgaaa agaaattcaa tatgaga 27

<210> SEQ ID NO 33

<211> LENGTH: 25
<212> TYPE: DNA
<213> ORGANISM: Pinus taeda L.

<400> SEQUENCE: 33
cacacaacca aaattaaaac attca 25

<210> SEQ ID NO 34
<211> LENGTH: 20
<212> TYPE: DNA
<213> ORGANISM: Pinus taeda L.

<400> SEQUENCE: 34
cacaaacaag ggggtctcat 20

<210> SEQ ID NO 35
<211> LENGTH: 20
<212> TYPE: DNA
<213> ORGANISM: Pinus taeda L.

<400> SEQUENCE: 35
acgaaacccc gagttgataa 20

<210> SEQ ID NO 36
<211> LENGTH: 20
<212> TYPE: DNA
<213> ORGANISM: Pinus taeda L.

<400> SEQUENCE: 36
taagcccttg aacatggtgg 20

<210> SEQ ID NO 37
<211> LENGTH: 20
<212> TYPE: DNA
<213> ORGANISM: Pinus taeda L.

<400> SEQUENCE: 37
atgtttgatg gggtcgtcat 20

<210> SEQ ID NO 38
<211> LENGTH: 20
<212> TYPE: DNA
<213> ORGANISM: Pinus taeda L.

<400> SEQUENCE: 38
catcatccca tcagacaacg 20

<210> SEQ ID NO 39
<211> LENGTH: 20
<212> TYPE: DNA
<213> ORGANISM: Pinus taeda L.

<400> SEQUENCE: 39
ccccttggtg gaacaacata 20

<210> SEQ ID NO 40
<211> LENGTH: 20
<212> TYPE: DNA
<213> ORGANISM: Pinus taeda L.

<400> SEQUENCE: 40
ttggaaaatg gcggaattta 20

-continued

<210> SEQ ID NO 41
<211> LENGTH: 20
<212> TYPE: DNA
<213> ORGANISM: Pinus taeda L.

<400> SEQUENCE: 41
tgcatttcat ttttgcgtgt 20

<210> SEQ ID NO 42
<211> LENGTH: 23
<212> TYPE: DNA
<213> ORGANISM: Pinus taeda L.

<400> SEQUENCE: 42
aggacatgga gagtttacac atg 23

<210> SEQ ID NO 43
<211> LENGTH: 20
<212> TYPE: DNA
<213> ORGANISM: Pinus taeda L.

<400> SEQUENCE: 43
atcagattgg tggatcggag 20

<210> SEQ ID NO 44
<211> LENGTH: 20
<212> TYPE: DNA
<213> ORGANISM: Pinus taeda L.

<400> SEQUENCE: 44
tgactgataa gggtttcgcc 20

<210> SEQ ID NO 45
<211> LENGTH: 20
<212> TYPE: DNA
<213> ORGANISM: Pinus taeda L.

<400> SEQUENCE: 45
gcttcatgat ttctcgatcg 20

<210> SEQ ID NO 46
<211> LENGTH: 21
<212> TYPE: DNA
<213> ORGANISM: Pinus taeda L.

<400> SEQUENCE: 46
tctgcgtgga taaaggaatt t 21

<210> SEQ ID NO 47
<211> LENGTH: 20
<212> TYPE: DNA
<213> ORGANISM: Pinus taeda L.

<400> SEQUENCE: 47
tcgtgtcgaa acattggaaa 20

<210> SEQ ID NO 48
<211> LENGTH: 20
<212> TYPE: DNA
<213> ORGANISM: Pinus taeda L.

<400> SEQUENCE: 48
tatcacctat agccccgtcg 20

-continued

<210> SEQ ID NO 49
<211> LENGTH: 21
<212> TYPE: DNA
<213> ORGANISM: Pinus taeda L.

<400> SEQUENCE: 49
tcataccgag agaggtcttt g 21

<210> SEQ ID NO 50
<211> LENGTH: 20
<212> TYPE: DNA
<213> ORGANISM: Pinus taeda L.

<400> SEQUENCE: 50
gagcttaatt tgtgcctgcc 20

<210> SEQ ID NO 51
<211> LENGTH: 20
<212> TYPE: DNA
<213> ORGANISM: Pinus taeda L.

<400> SEQUENCE: 51
cgaccctagt ctcttgtgca 20

<210> SEQ ID NO 52
<211> LENGTH: 20
<212> TYPE: DNA
<213> ORGANISM: Pinus taeda L.

<400> SEQUENCE: 52
ttttggaccc taagccagag 20

<210> SEQ ID NO 53
<211> LENGTH: 20
<212> TYPE: DNA
<213> ORGANISM: Pinus taeda L.

<400> SEQUENCE: 53
aaccgtggtg ctctgatacc 20

<210> SEQ ID NO 54
<211> LENGTH: 23
<212> TYPE: DNA
<213> ORGANISM: Pinus taeda L.

<400> SEQUENCE: 54
tgcaagtcaa gagctagaga caa 23

<210> SEQ ID NO 55
<211> LENGTH: 20
<212> TYPE: DNA
<213> ORGANISM: Pinus taeda L.

<400> SEQUENCE: 55
gtttacattt tcctggggca 20

<210> SEQ ID NO 56
<211> LENGTH: 21
<212> TYPE: DNA
<213> ORGANISM: Pinus taeda L.

<400> SEQUENCE: 56
gatttacaaa aatccctgcc a 21

-continued

<210> SEQ ID NO 57
<211> LENGTH: 21
<212> TYPE: DNA
<213> ORGANISM: Pinus taeda L.

<400> SEQUENCE: 57
cacgcatgag ctgagtcata a 21

<210> SEQ ID NO 58
<211> LENGTH: 22
<212> TYPE: DNA
<213> ORGANISM: Pinus taeda L.

<400> SEQUENCE: 58
tgtgtttccc actatgctaa gc 22

<210> SEQ ID NO 59
<211> LENGTH: 20
<212> TYPE: DNA
<213> ORGANISM: Pinus taeda L.

<400> SEQUENCE: 59
accaaccgag ggagctaaat 20

<210> SEQ ID NO 60
<211> LENGTH: 22
<212> TYPE: DNA
<213> ORGANISM: Pinus taeda L.

<400> SEQUENCE: 60
aaaaacgaca ttcacttcaa ca 22

<210> SEQ ID NO 61
<211> LENGTH: 20
<212> TYPE: DNA
<213> ORGANISM: Pinus taeda L.

<400> SEQUENCE: 61
gtgtgccacg gatgtatgag 20

<210> SEQ ID NO 62
<211> LENGTH: 20
<212> TYPE: DNA
<213> ORGANISM: Pinus taeda L.

<400> SEQUENCE: 62
ttgctgaaag ggccagtagt 20

<210> SEQ ID NO 63
<211> LENGTH: 20
<212> TYPE: DNA
<213> ORGANISM: Pinus taeda L.

<400> SEQUENCE: 63
atatggctta cctcgggtcc 20

<210> SEQ ID NO 64
<211> LENGTH: 20
<212> TYPE: DNA
<213> ORGANISM: Pinus taeda L.

<400> SEQUENCE: 64
cataaaccca ttgggtccag 20

<210> SEQ ID NO 65
<211> LENGTH: 20
<212> TYPE: DNA
<213> ORGANISM: Pinus taeda L.

<400> SEQUENCE: 65
tggaagccac aatttgttga 20

<210> SEQ ID NO 66
<211> LENGTH: 21
<212> TYPE: DNA
<213> ORGANISM: Pinus taeda L.

<400> SEQUENCE: 66
tgcaataaaa ccatgcaaca a 21

<210> SEQ ID NO 67
<211> LENGTH: 19
<212> TYPE: DNA
<213> ORGANISM: Pinus taeda L.

<400> SEQUENCE: 67
ttttgagaat gtccgtgcg 19

<210> SEQ ID NO 68
<211> LENGTH: 20
<212> TYPE: DNA
<213> ORGANISM: Pinus taeda L.

<400> SEQUENCE: 68
tgatgcattg caaaatcatg 20

<210> SEQ ID NO 69
<211> LENGTH: 22
<212> TYPE: DNA
<213> ORGANISM: Pinus taeda L.

<400> SEQUENCE: 69
tgatcctaag ccttagaaac cc 22

<210> SEQ ID NO 70
<211> LENGTH: 21
<212> TYPE: DNA
<213> ORGANISM: Pinus taeda L.

<400> SEQUENCE: 70
ttttgtcacc catgcatatg a 21

<210> SEQ ID NO 71
<211> LENGTH: 20
<212> TYPE: DNA
<213> ORGANISM: Pinus taeda L.

<400> SEQUENCE: 71
tgtaggagca caagccattg 20

<210> SEQ ID NO 72
<211> LENGTH: 20
<212> TYPE: DNA
<213> ORGANISM: Pinus taeda L.

<400> SEQUENCE: 72
aacacagttg gaccgtttga 20

<210> SEQ ID NO 73
<211> LENGTH: 20
<212> TYPE: DNA
<213> ORGANISM: Pinus taeda L.

<400> SEQUENCE: 73
tgtttgcaaa tcatggggta 20

<210> SEQ ID NO 74
<211> LENGTH: 20
<212> TYPE: DNA
<213> ORGANISM: Pinus taeda L.

<400> SEQUENCE: 74
ccagtgtcca tgccaatttt 20

<210> SEQ ID NO 75
<211> LENGTH: 20
<212> TYPE: DNA
<213> ORGANISM: Pinus taeda L.

<400> SEQUENCE: 75
gatcccttgt cccagaaaca 20

<210> SEQ ID NO 76
<211> LENGTH: 20
<212> TYPE: DNA
<213> ORGANISM: Pinus taeda L.

<400> SEQUENCE: 76
tgttgatgtt atgcctgggt 20

<210> SEQ ID NO 77
<211> LENGTH: 20
<212> TYPE: DNA
<213> ORGANISM: Pinus taeda L.

<400> SEQUENCE: 77 gaggggtct catacaccaa 20

<210> SEQ ID NO 78
<211> LENGTH: 24
<212> TYPE: DNA
<213> ORGANISM: Pinus taeda L.

<400> SEQUENCE: 78
tgcatagagg atgtatttct tgga 24

<210> SEQ ID NO 79
<211> LENGTH: 20
<212> TYPE: DNA
<213> ORGANISM: Pinus taeda L.

<400> SEQUENCE: 79
tcctcctgag tggtcccata 20

<210> SEQ ID NO 80
<211> LENGTH: 20
<212> TYPE: DNA
<213> ORGANISM: Pinus taeda L.

-continued

<400> SEQUENCE: 80
atggatatga ggcctgttgg 20

<210> SEQ ID NO 81
<211> LENGTH: 20
<212> TYPE: DNA
<213> ORGANISM: Pinus taeda L.

<400> SEQUENCE: 81
ttggattgga cctgaatcaa 20

<210> SEQ ID NO 82
<211> LENGTH: 20
<212> TYPE: DNA
<213> ORGANISM: Pinus taeda L.

<400> SEQUENCE: 82
ttggcagtct tcgaggtctt 20

<210> SEQ ID NO 83
<211> LENGTH: 20
<212> TYPE: DNA
<213> ORGANISM: Pinus taeda L.

<400> SEQUENCE: 83
tgttcctctc aagtgacccc 20

<210> SEQ ID NO 84
<211> LENGTH: 20
<212> TYPE: DNA
<213> ORGANISM: Pinus taeda L.

<400> SEQUENCE: 84
cttcagcttc ccaccagaag 20

<210> SEQ ID NO 85
<211> LENGTH: 20
<212> TYPE: DNA
<213> ORGANISM: Pinus taeda L.

<400> SEQUENCE: 85
ggaatgtatt cccggttcct 20

<210> SEQ ID NO 86
<211> LENGTH: 20
<212> TYPE: DNA
<213> ORGANISM: Pinus taeda L.

<400> SEQUENCE: 86
ctcccggata ttgaggaggt 20

<210> SEQ ID NO 87
<211> LENGTH: 20
<212> TYPE: DNA
<213> ORGANISM: Pinus taeda L.

<400> SEQUENCE: 87
cgctactatt ggccgaatct 20

<210> SEQ ID NO 88
<211> LENGTH: 20
<212> TYPE: DNA
<213> ORGANISM: Pinus taeda L.

<400> SEQUENCE: 88
ctgtgaggaa atccctggaa 20

<210> SEQ ID NO 89
<211> LENGTH: 20
<212> TYPE: DNA
<213> ORGANISM: Pinus taeda L.

<400> SEQUENCE: 89
cttttccctt tccatgacca 20

<210> SEQ ID NO 90
<211> LENGTH: 20
<212> TYPE: DNA
<213> ORGANISM: Pinus taeda L.

<400> SEQUENCE: 90
gagtcgagta accaggtggc 20

<210> SEQ ID NO 91
<211> LENGTH: 21
<212> TYPE: DNA
<213> ORGANISM: Pinus taeda L.

<400> SEQUENCE: 91
tcaatcacca attatttggc t 21

<210> SEQ ID NO 92
<211> LENGTH: 21
<212> TYPE: DNA
<213> ORGANISM: Pinus taeda L.

<400> SEQUENCE: 92
ggagtggatg aaactatgcc a 21

<210> SEQ ID NO 93
<211> LENGTH: 20
<212> TYPE: DNA
<213> ORGANISM: Pinus taeda L.

<400> SEQUENCE: 93
ccaatgcata atgcaaccac 20

<210> SEQ ID NO 94
<211> LENGTH: 20
<212> TYPE: DNA
<213> ORGANISM: Pinus taeda L.

<400> SEQUENCE: 94
tagccatggt gctcagtctg 20

<210> SEQ ID NO 95
<211> LENGTH: 20
<212> TYPE: DNA
<213> ORGANISM: Pinus taeda L.

<400> SEQUENCE: 95
ggttgttgtg cacgagctta 20

<210> SEQ ID NO 96
<211> LENGTH: 22
<212> TYPE: DNA

-continued

<213> ORGANISM: Pinus taeda L.

<400> SEQUENCE: 96
tcagtgaagt tcaagggagg tt 22

<210> SEQ ID NO 97
<211> LENGTH: 21
<212> TYPE: DNA
<213> ORGANISM: Pinus taeda L.

<400> SEQUENCE: 97
aggaattggt gattcatgtg g 21

<210> SEQ ID NO 98
<211> LENGTH: 20
<212> TYPE: DNA
<213> ORGANISM: Pinus taeda L.

<400> SEQUENCE: 98
ataaaagaat cggccctggt 20

<210> SEQ ID NO 99
<211> LENGTH: 22
<212> TYPE: DNA
<213> ORGANISM: Pinus taeda L.

<400> SEQUENCE: 99
cacaacactc aaacatgctc aa 22

<210> SEQ ID NO 100
<211> LENGTH: 20
<212> TYPE: DNA
<213> ORGANISM: Pinus taeda L.

<400> SEQUENCE: 100
aagaggatgt gaggtcccaa 20

<210> SEQ ID NO 101
<211> LENGTH: 20
<212> TYPE: DNA
<213> ORGANISM: Pinus taeda L.

<400> SEQUENCE: 101
cttggcgacc ttgtcataca 20

<210> SEQ ID NO 102
<211> LENGTH: 20
<212> TYPE: DNA
<213> ORGANISM: Pinus taeda L.

<400> SEQUENCE: 102
gggtccttag ggatcatggt 20

<210> SEQ ID NO 103
<211> LENGTH: 20
<212> TYPE: DNA
<213> ORGANISM: Pinus taeda L.

<400> SEQUENCE: 103
gtaagagtgc ctcgggtctg 20

<210> SEQ ID NO 104
<211> LENGTH: 20

-continued

<212> TYPE: DNA
<213> ORGANISM: Pinus taeda L.

<400> SEQUENCE: 104
ggtggtaggt agatcggcaa 20

<210> SEQ ID NO 105
<211> LENGTH: 20
<212> TYPE: DNA
<213> ORGANISM: Pinus taeda L.

<400> SEQUENCE: 105
ggcacaggtt ggacatctct 20

<210> SEQ ID NO 106
<211> LENGTH: 20
<212> TYPE: DNA
<213> ORGANISM: Pinus taeda L.

<400> SEQUENCE: 106
gtggtggaag ggagatttca 20

<210> SEQ ID NO 107
<211> LENGTH: 20
<212> TYPE: DNA
<213> ORGANISM: Pinus taeda L.

<400> SEQUENCE: 107
aaacacttgg actggatggg 20

<210> SEQ ID NO 108
<211> LENGTH: 20
<212> TYPE: DNA
<213> ORGANISM: Pinus taeda L.

<400> SEQUENCE: 108
tttggaggat gtttgttgca 20

<210> SEQ ID NO 109
<211> LENGTH: 23
<212> TYPE: DNA
<213> ORGANISM: Pinus taeda L.

<400> SEQUENCE: 109
tgttgtcatt agtggtagga tca 23

<210> SEQ ID NO 110
<211> LENGTH: 22
<212> TYPE: DNA
<213> ORGANISM: Pinus taeda L.

<400> SEQUENCE: 110
aagcgatgtc acttgttgag aa 22

<210> SEQ ID NO 111
<211> LENGTH: 20
<212> TYPE: DNA
<213> ORGANISM: Pinus taeda L.

<400> SEQUENCE: 111
ttttgtggtc attcgttgga 20

<210> SEQ ID NO 112

-continued

<211> LENGTH: 23
<212> TYPE: DNA
<213> ORGANISM: Pinus taeda L.

<400> SEQUENCE: 112
tcacatggaa gattatctcc aaa 23

<210> SEQ ID NO 113
<211> LENGTH: 20
<212> TYPE: DNA
<213> ORGANISM: Pinus taeda L.

<400> SEQUENCE: 113
tcgtgattac attgctgcct 20

<210> SEQ ID NO 114
<211> LENGTH: 20
<212> TYPE: DNA
<213> ORGANISM: Pinus taeda L.

<400> SEQUENCE: 114
tccacaacaa tgatcgcttc 20

<210> SEQ ID NO 115
<211> LENGTH: 20
<212> TYPE: DNA
<213> ORGANISM: Pinus taeda L.

<400> SEQUENCE: 115
cattggaact tcaccgaagg 20

<210> SEQ ID NO 116
<211> LENGTH: 20
<212> TYPE: DNA
<213> ORGANISM: Pinus taeda L.

<400> SEQUENCE: 116
gtgctattgg gtccagcaat 20

<210> SEQ ID NO 117
<211> LENGTH: 20
<212> TYPE: DNA
<213> ORGANISM: Pinus taeda L.

<400> SEQUENCE: 117
gttggtgagg agacttggga 20

<210> SEQ ID NO 118
<211> LENGTH: 23
<212> TYPE: DNA
<213> ORGANISM: Pinus taeda L.

<400> SEQUENCE: 118
aagaacaatt ccaatatgga tga 23

<210> SEQ ID NO 119
<211> LENGTH: 20
<212> TYPE: DNA
<213> ORGANISM: Pinus taeda L.

<400> SEQUENCE: 119
gcgagacaga aacggaaaag 20

<210> SEQ ID NO 120
<211> LENGTH: 20
<212> TYPE: DNA
<213> ORGANISM: Pinus taeda L.

<400> SEQUENCE: 120
ctctgctaga ccgctcagct 20

<210> SEQ ID NO 121
<211> LENGTH: 20
<212> TYPE: DNA
<213> ORGANISM: Pinus taeda L.

<400> SEQUENCE: 121
caaaatgcag aggggcttaa 20

<210> SEQ ID NO 122
<211> LENGTH: 20
<212> TYPE: DNA
<213> ORGANISM: Pinus taeda L.

<400> SEQUENCE: 122
ccagtccatc gaatcacgta 20

<210> SEQ ID NO 123
<211> LENGTH: 21
<212> TYPE: DNA
<213> ORGANISM: Pinus taeda L.

<400> SEQUENCE: 123
cagctctctt aatagcctcg g 21

<210> SEQ ID NO 124
<211> LENGTH: 20
<212> TYPE: DNA
<213> ORGANISM: Pinus taeda L.

<400> SEQUENCE: 124
gcacatagca acgctgaaga 20

<210> SEQ ID NO 125
<211> LENGTH: 20
<212> TYPE: DNA
<213> ORGANISM: Pinus taeda L.

<400> SEQUENCE: 125
gcaaagggaa gcaaagtcat 20

<210> SEQ ID NO 126
<211> LENGTH: 21
<212> TYPE: DNA
<213> ORGANISM: Pinus taeda L.

<400> SEQUENCE: 126
ttcgtcctct tttgaacgag t 21

<210> SEQ ID NO 127
<211> LENGTH: 20
<212> TYPE: DNA
<213> ORGANISM: Pinus taeda L.

<400> SEQUENCE: 127
gacaaacaac ccttgcgttt 20

<210> SEQ ID NO 128
<211> LENGTH: 19
<212> TYPE: DNA
<213> ORGANISM: Pinus taeda L.

<400> SEQUENCE: 128
gacccatcaa gccaacatg 19

<210> SEQ ID NO 129
<211> LENGTH: 20
<212> TYPE: DNA
<213> ORGANISM: Pinus taeda L.

<400> SEQUENCE: 129
ggttgtgctt tcccagagag 20

<210> SEQ ID NO 130
<211> LENGTH: 20
<212> TYPE: DNA
<213> ORGANISM: Pinus taeda L.

<400> SEQUENCE: 130
gaatgcaagg tagccaggag 20

<210> SEQ ID NO 131
<211> LENGTH: 20
<212> TYPE: DNA
<213> ORGANISM: Pinus taeda L.

<400> SEQUENCE: 131
cgcaagctat gatacaacgc 20

<210> SEQ ID NO 132
<211> LENGTH: 20
<212> TYPE: DNA
<213> ORGANISM: Pinus taeda L.

<400> SEQUENCE: 132
tgttggctga gtgtgaaagc 20

<210> SEQ ID NO 133
<211> LENGTH: 20
<212> TYPE: DNA
<213> ORGANISM: Pinus taeda L.

<400> SEQUENCE: 133
gttgtgatcc aagtcccctg 20

<210> SEQ ID NO 134
<211> LENGTH: 20
<212> TYPE: DNA
<213> ORGANISM: Pinus taeda L.

<400> SEQUENCE: 134
tggtccattc ggtcctattc 20

<210> SEQ ID NO 135
<211> LENGTH: 20
<212> TYPE: DNA
<213> ORGANISM: Pinus taeda L.

<400> SEQUENCE: 135
tggccatcga acttgtgtta 20

<210> SEQ ID NO 136
<211> LENGTH: 20
<212> TYPE: DNA
<213> ORGANISM: Pinus taeda L.

<400> SEQUENCE: 136
cacgaccacc agtcacctta 20

<210> SEQ ID NO 137
<211> LENGTH: 20
<212> TYPE: DNA
<213> ORGANISM: Pinus taeda L.

<400> SEQUENCE: 137
tagtcgaatc gggcctgtac 20

<210> SEQ ID NO 138
<211> LENGTH: 20
<212> TYPE: DNA
<213> ORGANISM: Pinus taeda L.

<400> SEQUENCE: 138
ttgctcctct gtgtccttca 20

<210> SEQ ID NO 139
<211> LENGTH: 20
<212> TYPE: DNA
<213> ORGANISM: Pinus taeda L.

<400> SEQUENCE: 139
tgcatgcatt acaaatgtca 20

<210> SEQ ID NO 140
<211> LENGTH: 21
<212> TYPE: DNA
<213> ORGANISM: Pinus taeda L.

<400> SEQUENCE: 140
cgcttttaaa tcaaccaaac g 21

<210> SEQ ID NO 141
<211> LENGTH: 20
<212> TYPE: DNA
<213> ORGANISM: Pinus taeda L.

<400> SEQUENCE: 141
acagatgtca aggccaaagg 20

<210> SEQ ID NO 142
<211> LENGTH: 20
<212> TYPE: DNA
<213> ORGANISM: Pinus taeda L.

<400> SEQUENCE: 142
ctgcattcaa attacccgct 20

<210> SEQ ID NO 143
<211> LENGTH: 20
<212> TYPE: DNA
<213> ORGANISM: Pinus taeda L.

<400> SEQUENCE: 143

```
tgaaaccaat ccttctgcaa                                                   20


<210> SEQ ID NO 144
<211> LENGTH: 20
<212> TYPE: DNA
<213> ORGANISM: Pinus taeda L.

<400> SEQUENCE: 144

ctgattcctc tggcttctcg                                                   20


<210> SEQ ID NO 145
<211> LENGTH: 21
<212> TYPE: DNA
<213> ORGANISM: Pinus taeda L.

<400> SEQUENCE: 145

ttcagttatg cattcacgag c                                                 21


<210> SEQ ID NO 146
<211> LENGTH: 20
<212> TYPE: DNA
<213> ORGANISM: Pinus taeda L.

<400> SEQUENCE: 146

gtcctcctgg gttatccctc                                                   20


<210> SEQ ID NO 147
<211> LENGTH: 20
<212> TYPE: DNA
<213> ORGANISM: Pinus taeda L.

<400> SEQUENCE: 147

gaaactttcc cctacgagcc                                                   20


<210> SEQ ID NO 148
<211> LENGTH: 20
<212> TYPE: DNA
<213> ORGANISM: Pinus taeda L.

<400> SEQUENCE: 148

ttccccaaaa gttcacaggt                                                   20


<210> SEQ ID NO 149
<211> LENGTH: 20
<212> TYPE: DNA
<213> ORGANISM: Pinus taeda L.

<400> SEQUENCE: 149

attcctagat ggacctgggg                                                   20


<210> SEQ ID NO 150
<211> LENGTH: 20
<212> TYPE: DNA
<213> ORGANISM: Pinus taeda L.

<400> SEQUENCE: 150

cgacataagc ccaccaaatt                                                   20


<210> SEQ ID NO 151
<211> LENGTH: 20
<212> TYPE: DNA
<213> ORGANISM: Pinus taeda L.

<400> SEQUENCE: 151
```

tggatcgtga tcctctgtga 20

<210> SEQ ID NO 152
<211> LENGTH: 20
<212> TYPE: DNA
<213> ORGANISM: Pinus taeda L.

<400> SEQUENCE: 152
gcttccatca cattgggatt 20

<210> SEQ ID NO 153
<211> LENGTH: 20
<212> TYPE: DNA
<213> ORGANISM: Pinus taeda L.

<400> SEQUENCE: 153
ttgcaattgc gattaactgc 20

<210> SEQ ID NO 154
<211> LENGTH: 20
<212> TYPE: DNA
<213> ORGANISM: Pinus taeda L.

<400> SEQUENCE: 154
ataatggcat agccgaatcg 20

<210> SEQ ID NO 155
<211> LENGTH: 20
<212> TYPE: DNA
<213> ORGANISM: Pinus taeda L.

<400> SEQUENCE: 155
tgcatagaaa gtcgccctct 20

<210> SEQ ID NO 156
<211> LENGTH: 20
<212> TYPE: DNA
<213> ORGANISM: Pinus taeda L.

<400> SEQUENCE: 156
atgcatgagg taacttgggg 20

<210> SEQ ID NO 157
<211> LENGTH: 20
<212> TYPE: DNA
<213> ORGANISM: Pinus taeda L.

<400> SEQUENCE: 157
catcccaagc atcctcaagt 20

<210> SEQ ID NO 158
<211> LENGTH: 24
<212> TYPE: DNA
<213> ORGANISM: Pinus taeda L.

<400> SEQUENCE: 158
tcaaaaatgt ggtttaatgg aaaa 24

<210> SEQ ID NO 159
<211> LENGTH: 20
<212> TYPE: DNA
<213> ORGANISM: Pinus taeda L.

-continued

<400> SEQUENCE: 159
ttgtgaattg tgtccatggg 20

<210> SEQ ID NO 160
<211> LENGTH: 20
<212> TYPE: DNA
<213> ORGANISM: Pinus taeda L.

<400> SEQUENCE: 160
atcggtgagg cttaaacacg 20

<210> SEQ ID NO 161
<211> LENGTH: 20
<212> TYPE: DNA
<213> ORGANISM: Pinus taeda L.

<400> SEQUENCE: 161
atggaaggat ccacaaccaa 20

<210> SEQ ID NO 162
<211> LENGTH: 20
<212> TYPE: DNA
<213> ORGANISM: Pinus taeda L.

<400> SEQUENCE: 162
gggcttgttg ctggtctatg 20

<210> SEQ ID NO 163
<211> LENGTH: 21
<212> TYPE: DNA
<213> ORGANISM: Pinus taeda L.

<400> SEQUENCE: 163
ggttgatgat gtcgatgttg a 21

<210> SEQ ID NO 164
<211> LENGTH: 21
<212> TYPE: DNA
<213> ORGANISM: Pinus taeda L.

<400> SEQUENCE: 164
ttcttgcaaa cacagcatgt t 21

<210> SEQ ID NO 165
<211> LENGTH: 22
<212> TYPE: DNA
<213> ORGANISM: Pinus taeda L.

<400> SEQUENCE: 165
tgatcctaag ccttagaaac cc 22

<210> SEQ ID NO 166
<211> LENGTH: 24
<212> TYPE: DNA
<213> ORGANISM: Pinus taeda L.

<400> SEQUENCE: 166
ttgtcaccca tgtcatatga taca 24

<210> SEQ ID NO 167
<211> LENGTH: 20
<212> TYPE: DNA
<213> ORGANISM: Pinus taeda L.

<400> SEQUENCE: 167
aaaaagaatg aggcgcacac 20

<210> SEQ ID NO 168
<211> LENGTH: 20
<212> TYPE: DNA
<213> ORGANISM: Pinus taeda L.

<400> SEQUENCE: 168
cccgtttatg gcattgattc 20

<210> SEQ ID NO 169
<211> LENGTH: 20
<212> TYPE: DNA
<213> ORGANISM: Pinus taeda L.

<400> SEQUENCE: 169
gaaaacgaac aagccatggt 20

<210> SEQ ID NO 170
<211> LENGTH: 22
<212> TYPE: DNA
<213> ORGANISM: Pinus taeda L.

<400> SEQUENCE: 170
tgtttacttg catgcatgtg tg 22

<210> SEQ ID NO 171
<211> LENGTH: 20
<212> TYPE: DNA
<213> ORGANISM: Pinus taeda L.

<400> SEQUENCE: 171
gtgcttccct tgcttcagac 20

<210> SEQ ID NO 172
<211> LENGTH: 20
<212> TYPE: DNA
<213> ORGANISM: Pinus taeda L.

<400> SEQUENCE: 172
gcaaatgcaa actttgggta 20

<210> SEQ ID NO 173
<211> LENGTH: 20
<212> TYPE: DNA
<213> ORGANISM: Pinus taeda L.

<400> SEQUENCE: 173
cattcatggt tccaatgtgg 20

<210> SEQ ID NO 174
<211> LENGTH: 20
<212> TYPE: DNA
<213> ORGANISM: Pinus taeda L.

<400> SEQUENCE: 174
tgataagcgt ggatctcgtg 20

<210> SEQ ID NO 175
<211> LENGTH: 20
<212> TYPE: DNA

<213> ORGANISM: Pinus taeda L.

<400> SEQUENCE: 175
gttatccccc atgttgttgc 20

<210> SEQ ID NO 176
<211> LENGTH: 24
<212> TYPE: DNA
<213> ORGANISM: Pinus taeda L.

<400> SEQUENCE: 176
gggtagaagc actatgcttt catt 24

<210> SEQ ID NO 177
<211> LENGTH: 22
<212> TYPE: DNA
<213> ORGANISM: Pinus taeda L.

<400> SEQUENCE: 177
ttgagcagac atcatcaaca ct 22

<210> SEQ ID NO 178
<211> LENGTH: 20
<212> TYPE: DNA
<213> ORGANISM: Pinus taeda L.

<400> SEQUENCE: 178
ccaggttatg cctcaaagag 20

<210> SEQ ID NO 179
<211> LENGTH: 20
<212> TYPE: DNA
<213> ORGANISM: Pinus taeda L.

<400> SEQUENCE: 179
cacggatctc tggaaaccat 20

<210> SEQ ID NO 180
<211> LENGTH: 20
<212> TYPE: DNA
<213> ORGANISM: Pinus taeda L.

<400> SEQUENCE: 180
cgctggtttc cctcagaata 20

<210> SEQ ID NO 181
<211> LENGTH: 23
<212> TYPE: DNA
<213> ORGANISM: Pinus taeda L.

<400> SEQUENCE: 181
ggattttgtt ttcctcataa tca 23

<210> SEQ ID NO 182
<211> LENGTH: 20
<212> TYPE: DNA
<213> ORGANISM: Pinus taeda L.

<400> SEQUENCE: 182
gggcatagca tatgccactt 20

<210> SEQ ID NO 183
<211> LENGTH: 20

<212> TYPE: DNA
<213> ORGANISM: Pinus taeda L.

<400> SEQUENCE: 183
gcaagaccga ctggattagc 20

<210> SEQ ID NO 184
<211> LENGTH: 21
<212> TYPE: DNA
<213> ORGANISM: Pinus taeda L.

<400> SEQUENCE: 184
gaggtcatga tatgtggtgg g 21

<210> SEQ ID NO 185
<211> LENGTH: 20
<212> TYPE: DNA
<213> ORGANISM: Pinus taeda L.

<400> SEQUENCE: 185
ctgcgtagca aatcactgga 20

<210> SEQ ID NO 186
<211> LENGTH: 21
<212> TYPE: DNA
<213> ORGANISM: Pinus taeda L.

<400> SEQUENCE: 186
tgatctgatg tgggatcaac a 21

<210> SEQ ID NO 187
<211> LENGTH: 20
<212> TYPE: DNA
<213> ORGANISM: Pinus taeda L.

<400> SEQUENCE: 187
ccattgcccg agctagttta 20

<210> SEQ ID NO 188
<211> LENGTH: 20
<212> TYPE: DNA
<213> ORGANISM: Pinus taeda L.

<400> SEQUENCE: 188
ttatattgga cccaaggccc 20

<210> SEQ ID NO 189
<211> LENGTH: 20
<212> TYPE: DNA
<213> ORGANISM: Pinus taeda L.

<400> SEQUENCE: 189
tggagtctcg aacactgtgg 20

<210> SEQ ID NO 190
<211> LENGTH: 20
<212> TYPE: DNA
<213> ORGANISM: Pinus taeda L.

<400> SEQUENCE: 190
aatcatccca atggcaacat 20

<210> SEQ ID NO 191

-continued

<211> LENGTH: 20
<212> TYPE: DNA
<213> ORGANISM: Pinus taeda L.

<400> SEQUENCE: 191
gcatccatct tcagcatcct 20

<210> SEQ ID NO 192
<211> LENGTH: 22
<212> TYPE: DNA
<213> ORGANISM: Pinus taeda L.

<400> SEQUENCE: 192
ttcatacgac acctttgaaa tg 22

<210> SEQ ID NO 193
<211> LENGTH: 20
<212> TYPE: DNA
<213> ORGANISM: Pinus taeda L.

<400> SEQUENCE: 193
ccattagaca agtgcgcatg 20

<210> SEQ ID NO 194
<211> LENGTH: 20
<212> TYPE: DNA
<213> ORGANISM: Pinus taeda L.

<400> SEQUENCE: 194
tgaaaaagga atttccccaa 20

<210> SEQ ID NO 195
<211> LENGTH: 22
<212> TYPE: DNA
<213> ORGANISM: Pinus taeda L.

<400> SEQUENCE: 195
tctacgacaa aaccacgtag tg 22

<210> SEQ ID NO 196
<211> LENGTH: 20
<212> TYPE: DNA
<213> ORGANISM: Pinus taeda L.

<400> SEQUENCE: 196
catgtggctt tgtggcatat 20

<210> SEQ ID NO 197
<211> LENGTH: 20
<212> TYPE: DNA
<213> ORGANISM: Pinus taeda L.

<400> SEQUENCE: 197
tgtgacctga aaattcccct 20

<210> SEQ ID NO 198
<211> LENGTH: 20
<212> TYPE: DNA
<213> ORGANISM: Pinus taeda L.

<400> SEQUENCE: 198
ggcttgcaac cagttccata 20

```
<210> SEQ ID NO 199
<211> LENGTH: 20
<212> TYPE: DNA
<213> ORGANISM: Pinus taeda L.

<400> SEQUENCE: 199

gacctaaaga ggttcacgcg                                               20


<210> SEQ ID NO 200
<211> LENGTH: 24
<212> TYPE: DNA
<213> ORGANISM: Pinus taeda L.

<400> SEQUENCE: 200

tcaaatcttg ggttagtatg caga                                          24


<210> SEQ ID NO 201
<211> LENGTH: 20
<212> TYPE: DNA
<213> ORGANISM: Pinus taeda L.

<400> SEQUENCE: 201

atccctgtgg ggatgagtta                                               20


<210> SEQ ID NO 202
<211> LENGTH: 22
<212> TYPE: DNA
<213> ORGANISM: Pinus taeda L.

<400> SEQUENCE: 202

tgcctcttaa gcatcaaatg tt                                            22


<210> SEQ ID NO 203
<211> LENGTH: 20
<212> TYPE: DNA
<213> ORGANISM: Pinus taeda L.

<400> SEQUENCE: 203

gaacccgatg gattttcaaa                                               20


<210> SEQ ID NO 204
<211> LENGTH: 21
<212> TYPE: DNA
<213> ORGANISM: Pinus taeda L.

<400> SEQUENCE: 204

caaactgtaa gctcaggagg a                                             21


<210> SEQ ID NO 205
<211> LENGTH: 20
<212> TYPE: DNA
<213> ORGANISM: Pinus taeda L.

<400> SEQUENCE: 205

cagtgttgat tgtgtgccag                                               20


<210> SEQ ID NO 206
<211> LENGTH: 20
<212> TYPE: DNA
<213> ORGANISM: Pinus taeda L.

<400> SEQUENCE: 206

tctgccacaa tttggaaaca                                               20
```

<210> SEQ ID NO 207
<211> LENGTH: 20
<212> TYPE: DNA
<213> ORGANISM: Pinus taeda L.

<400> SEQUENCE: 207
agcataatga gcccttctcg 20

<210> SEQ ID NO 208
<211> LENGTH: 20
<212> TYPE: DNA
<213> ORGANISM: Pinus taeda L.

<400> SEQUENCE: 208
agaatatgtg tccctccccc 20

<210> SEQ ID NO 209
<211> LENGTH: 20
<212> TYPE: DNA
<213> ORGANISM: Pinus taeda L.

<400> SEQUENCE: 209
tggttgtgcg agatcacaat 20

<210> SEQ ID NO 210
<211> LENGTH: 20
<212> TYPE: DNA
<213> ORGANISM: Pinus taeda L.

<400> SEQUENCE: 210
ttgagggaat tgaaattggg 20

<210> SEQ ID NO 211
<211> LENGTH: 22
<212> TYPE: DNA
<213> ORGANISM: Pinus taeda L.

<400> SEQUENCE: 211
tgctcaatat agaccacttg ca 22

<210> SEQ ID NO 212
<211> LENGTH: 22
<212> TYPE: DNA
<213> ORGANISM: Pinus taeda L.

<400> SEQUENCE: 212
agccataatt caacaaaagg aa 22

<210> SEQ ID NO 213
<211> LENGTH: 20
<212> TYPE: DNA
<213> ORGANISM: Pinus taeda L.

<400> SEQUENCE: 213
tcaaggaatt cattggagcc 20

<210> SEQ ID NO 214
<211> LENGTH: 20
<212> TYPE: DNA
<213> ORGANISM: Pinus taeda L.

<400> SEQUENCE: 214
tttggccata tcaaacccat 20

<210> SEQ ID NO 215
<211> LENGTH: 20
<212> TYPE: DNA
<213> ORGANISM: Pinus taeda L.

<400> SEQUENCE: 215
aaagggggtg tttgatggat 20

<210> SEQ ID NO 216
<211> LENGTH: 20
<212> TYPE: DNA
<213> ORGANISM: Pinus taeda L.

<400> SEQUENCE: 216
gatcgaaatc agcgaacaca 20

<210> SEQ ID NO 217
<211> LENGTH: 20
<212> TYPE: DNA
<213> ORGANISM: Pinus taeda L.

<400> SEQUENCE: 217
tttcatgacc ttggagtgga 20

<210> SEQ ID NO 218
<211> LENGTH: 20
<212> TYPE: DNA
<213> ORGANISM: Pinus taeda L.

<400> SEQUENCE: 218
attgatccca ttgttgctcc 20

<210> SEQ ID NO 219
<211> LENGTH: 20
<212> TYPE: DNA
<213> ORGANISM: Pinus taeda L.

<400> SEQUENCE: 219
tgtgtaaacc caggctaggc 20

<210> SEQ ID NO 220
<211> LENGTH: 20
<212> TYPE: DNA
<213> ORGANISM: Pinus taeda L.

<400> SEQUENCE: 220
atgatttcac aaagcccctc 20

<210> SEQ ID NO 221
<211> LENGTH: 20
<212> TYPE: DNA
<213> ORGANISM: Pinus taeda L.

<400> SEQUENCE: 221
aacattctag catgccccac 20

<210> SEQ ID NO 222
<211> LENGTH: 20
<212> TYPE: DNA
<213> ORGANISM: Pinus taeda L.

<400> SEQUENCE: 222
ttgtggtgga tgtctctcct 20

<210> SEQ ID NO 223
<211> LENGTH: 20
<212> TYPE: DNA
<213> ORGANISM: Pinus taeda L.

<400> SEQUENCE: 223
gagccacaca aacatgcatc 20

<210> SEQ ID NO 224
<211> LENGTH: 20
<212> TYPE: DNA
<213> ORGANISM: Pinus taeda L.

<400> SEQUENCE: 224
tttcccaaaa gttcacgagg 20

<210> SEQ ID NO 225
<211> LENGTH: 20
<212> TYPE: DNA
<213> ORGANISM: Pinus taeda L.

<400> SEQUENCE: 225
cccatgcaac tgcctagaat 20

<210> SEQ ID NO 226
<211> LENGTH: 18
<212> TYPE: DNA
<213> ORGANISM: Pinus taeda L.

<400> SEQUENCE: 226
aagctcgcac gtgggata 18

<210> SEQ ID NO 227
<211> LENGTH: 20
<212> TYPE: DNA
<213> ORGANISM: Pinus taeda L.

<400> SEQUENCE: 227
cccgctccta ttcaagatca 20

<210> SEQ ID NO 228
<211> LENGTH: 20
<212> TYPE: DNA
<213> ORGANISM: Pinus taeda L.

<400> SEQUENCE: 228
aggcgcctag aggcataatt 20

<210> SEQ ID NO 229
<211> LENGTH: 20
<212> TYPE: DNA
<213> ORGANISM: Pinus taeda L.

<400> SEQUENCE: 229
ttcctatcgt cagcgtccat 20

<210> SEQ ID NO 230
<211> LENGTH: 20
<212> TYPE: DNA
<213> ORGANISM: Pinus taeda L.

<400> SEQUENCE: 230
gttcacaggg gtcatgcttt 20

<210> SEQ ID NO 231
<211> LENGTH: 21
<212> TYPE: DNA
<213> ORGANISM: Pinus taeda L.

<400> SEQUENCE: 231
tgaaaccaat ttttcccctt t 21

<210> SEQ ID NO 232
<211> LENGTH: 20
<212> TYPE: DNA
<213> ORGANISM: Pinus taeda L.

<400> SEQUENCE: 232
ccaagaaaga caaggagcca 20

<210> SEQ ID NO 233
<211> LENGTH: 20
<212> TYPE: DNA
<213> ORGANISM: Pinus taeda L.

<400> SEQUENCE: 233
ccctgagaca tccaatccat 20

<210> SEQ ID NO 234
<211> LENGTH: 20
<212> TYPE: DNA
<213> ORGANISM: Pinus taeda L.

<400> SEQUENCE: 234
actttacatg agttgggcgg 20

<210> SEQ ID NO 235
<211> LENGTH: 20
<212> TYPE: DNA
<213> ORGANISM: Pinus taeda L.

<400> SEQUENCE: 235
ggcttaggca tagagggacc 20

<210> SEQ ID NO 236
<211> LENGTH: 20
<212> TYPE: DNA
<213> ORGANISM: Pinus taeda L.

<400> SEQUENCE: 236
aacaagttgg aagccaccat 20

<210> SEQ ID NO 237
<211> LENGTH: 413
<212> TYPE: DNA
<213> ORGANISM: Pinus taeda L.
<220> FEATURE:
<221> NAME/KEY: unsure
<222> LOCATION: n at 341.
<223> OTHER INFORMATION: n is a or g or c or t/u, unknown or other.

<400> SEQUENCE: 237
attaattttt tttgaaaaaa aaagagtttt gagaaaaagt ctaatatata cttggtggca 60
tgccaaaaga tctcaaaaat tcctttcata tatttgatta gacaagaaaa tatattatat 120

-continued

```
tataatcgtt taacttttta taattttaaa aaatatatta taattatttt aagtttatga    180

tgatgatgat gatgatggtg gttaacgtcc actgagacca aataatgatc atcggaccta    240

aaaagacaaa ttatttattt tgatttaaga ttttattcct atgctcaaaa agcttgcaga    300

gaagcctccc gagttcacta taattttggc attgtaaaag gntaggaaag gtcattggtg    360

gttacaaagg gtggtgaaat tgaaatctaa tgttggtgtt tgccggggct tcc           413


<210> SEQ ID NO 238
<211> LENGTH: 650
<212> TYPE: DNA
<213> ORGANISM: Pinus taeda L.
<220> FEATURE:
<221> NAME/KEY: unsure
<222> LOCATION: n at 293, 295, 327, 343, 366, 375, 397, 399, 401, 403, 422, 431, 434, 443, 461, 471,
<223> OTHER INFORMATION: n is  a or g or c or t/u, unknown or other.

<400> SEQUENCE: 238

ccgagaccaa gcaggcttgt aacagggcta caggtgagtg gctcctcaag accggtggtg     60

tcttcaggaa ctgaactttc atgatgatca tgatgatgat gatgatgact ggctagccgt    120

gttccaaata acgagtccac actcgccccc cgatgatcga ttctcgtcgt ccgatggacg    180

cgacggacga tacgagatct ctgtctaggc gggatcgaac gatcgatgga cgagcttgca    240

ctaccaaatg tacctgcggt ttcatatctc acggtggctt cgacactggt cgncnaaact    300

gactttgttc ttctgtgttg ttctgttngg tttttttgg gangttggtc ccggacaatt    360

tttcgncatc ttgtnaaaaa tgtggancnt ncnccgaagg tccgcgttgg ctttaaagcc    420

cnctgggcgg gncgntccaa acnttgcatc taaagggccc nttccncctt ntagttaatt    480

cctnttncaa tccccngggc cggcngtttt cancgtcgtn atgggaaaac ccgngttncc    540

cacttnatcn cttgcannna tccccttccc actggngtat accaaaaggc cgcccnttnc    600

ctcccnangt tggncncctg antggaangg cnnccttttg gggctnancc               650


<210> SEQ ID NO 239
<211> LENGTH: 405
<212> TYPE: DNA
<213> ORGANISM: Pinus taeda L.
<220> FEATURE:
<221> NAME/KEY: unsure
<222> LOCATION: n at 44, 137, 146 and 341.
<223> OTHER INFORMATION: n is  a or g or c or t/u, unknown or other.

<400> SEQUENCE: 239

gcgcaatttg ttattcctcc tatttcacag cttgatcaaa gtgntctagc tgcactgcct     60

gatgctatac gagatcaaat tttgaagaag caagcaggca gtgccaacct gacctctgtc    120

gccaagcatg aagaagngaa agaagntttg tcaatgcaaa gtccatcatc atcatcatca    180

tctgtgacaa tcacacccaa aaagcaacga ataattgatc catttgaacg aatgcgtgca    240

gcttcaatta caccaacgaa aaaaggaaaa ttgaaaaaag ttacaattaa ttcagctcct    300

tctacaccaa gtggatcaca aaaacgttgc aaatgttaga naatcatggg aacctacatg    360

gtcgccagtt gattccaaag ttttatccga actaccgata gaaat                    405


<210> SEQ ID NO 240
<211> LENGTH: 266
<212> TYPE: DNA
<213> ORGANISM: Pinus taeda L.

<400> SEQUENCE: 240

acaaccacat tagatctcag tttcataatc tttgtcgcaa tactgacctt cctagccttt     60
```

```
tacgatgtca taattatagt gagctcggga ggcttctctc caagcttttt gagcatagga    120

ataaaatctt aaatcaaact aaataatctg tttctttagg tctgatagac caaagtttgg    180

tctcagtgga tgttaaccac caccaccacc accatcatca tcatcatatc ttttgagaaa    240

atgaagattt ccttcttttc taaaat                                         266


<210> SEQ ID NO 241
<211> LENGTH: 425
<212> TYPE: DNA
<213> ORGANISM: Pinus taeda L.
<220> FEATURE:
<221> NAME/KEY: unsure
<222> LOCATION: n at 342, 377 and 413.
<223> OTHER INFORMATION: n is  a or g or c or t/u, unknown or other.

<400> SEQUENCE: 241

acgcactatt aatgaacaca aacaatgtat atgtagatta cttgattttt cacaattcta     60

taaatttatc taaatcatta tattattcgc catacattat gcaataacca tgagcagtat    120

catcataata gaatataagc acatcatcaa cacatcaaca caaaattcat attgacaccg    180

gatactgagg tggaaaccta atttgggaga aaaccattgt tgttgttgtc tcttattatt    240

attattatta ttattattat tattattata aagaaaaatt cttcttacat cttgcacaat    300

cacagactct tacgaagttg cgggctccta cctacgggaa gntacaacct ctagaaatta    360

tccagctcca ctggaangaa gctactactc cctaatcaag tttaccagct ccnactgaaa    420

ggaac                                                                425


<210> SEQ ID NO 242
<211> LENGTH: 528
<212> TYPE: DNA
<213> ORGANISM: Pinus taeda L.
<220> FEATURE:
<221> NAME/KEY: unsure
<222> LOCATION: n at 375, 382, 408, 445, 467, 471...472, 485, 514 and 521.
<223> OTHER INFORMATION: n is  a or g or c or t/u, unknown or other.

<400> SEQUENCE: 242

attgttcttc tggattaatt acactagtaa tttttcaaat caaagtttca aaccaaccaa     60

tgtggttcat catcaaaata tagatgaggg aggttgaact aagccatcga gattgataag    120

aggactggca atctgaacat agataatggg tggaaaatta ggagtagttg gattcctacc    180

ctgacttctt aggtggcttt gtccccccatc taaaatttaa tttaattatt attattatta    240

ttattattat tattattatt attattatta ttattattat tactattttg gtcttattcc    300

cttctatttt cctagcttaa tttatgatta ttacatataa ttatttactt ctagtttaac    360

cctcttcctt ttttnatttc tntctttatt tctttcctat ttttttatnt tccatatctc    420

tagttaataa tttattatta attanttcaa ggatgtttta attatanttc tnnaagttta    480

acatntccta atttatattt tatttcccaa ctcncaatcc nttactaa                 528


<210> SEQ ID NO 243
<211> LENGTH: 400
<212> TYPE: DNA
<213> ORGANISM: Pinus taeda L.
<220> FEATURE:
<221> NAME/KEY: unsure
<222> LOCATION: n at 369 and 387.
<223> OTHER INFORMATION: n is  a or g or c or t/u, unknown or other.

<400> SEQUENCE: 243
```

-continued

```
acttgtagtc agttcaagag ttaacgcaag ggaaacctag caggttacaa cctggggtca      60

atcggattgg tagctacctg ttcgagatat tctgatttca cattaaaaag tgaaaagtga     120

gtgttttaag tctattatta ttattattat tatttatgac cttctcaatt atgcctaaaa     180

catcttgtct atttccagaa tctgaaattt cccatcaatt gggctatact acagactcct     240

ctgcatacac cttcctcact ttgaacatcg agagttcaac tacagaaaat ttgcaccttc     300

cactttgaga gttcaactac agaaaatttg caggctggcg gtggaaaaca gtcaaggtat     360

gcatacgant ccatggtgct gtttttnccg gaagaaatta                           400


<210> SEQ ID NO 244
<211> LENGTH: 284
<212> TYPE: DNA
<213> ORGANISM: Pinus taeda L.

<400> SEQUENCE: 244

attacaattt tcttcttact taattggaga acatgcttgc aagttgcaat ttgtaaatga      60

gatttttact cgagaaataa aaaggactag gtgaagaaca tgctccaacc attagggaat     120

ataaggtggt tgggtataat cctagtgaat atattattat tattattatt attattttta     180

actgattttg tggaaaatgc tccatttttt atacatgtta cttttctctt aaatccactt     240

atataagtga ctataaattg aagaaactgt gactttacct agat                      284


<210> SEQ ID NO 245
<211> LENGTH: 294
<212> TYPE: DNA
<213> ORGANISM: Pinus taeda L.

<400> SEQUENCE: 245

acgggaaggt ggtgaggagc agcagcgtaa tcagatggtc ataggcgttg tgcaaactgc      60

aggctccgga caaaacccta accccatcct gtacgttgtt tcctcatctt tgctttttcc     120

aaatccaagc atatatataa cccaatgaga tgaatagtta aaaaacaaaa aaaacaaaca     180

aacaaacaaa caaaaacatc ctaaaaaata gccaaaaatg taaaatctcg aaataatcct     240

tttgaggaga gcttttcaat atcttcaact cgccttccgg tgtagtggtt tagg            294


<210> SEQ ID NO 246
<211> LENGTH: 343
<212> TYPE: DNA
<213> ORGANISM: Pinus taeda L.

<400> SEQUENCE: 246

acacgaacgg tctacttaca cttgactgta ttggataata taccttctat atattcaata      60

ctgtccacct ataaccaaca gcacttaccc aaaaaaacct caaaaacatt tatataaaca     120

aacaaacaaa caaaaaaacc ctaaaaacac ctataaacat aaactaagtc caggaaaaga     180

ttttaatttt ctgatttact gggctttcat gaggctgaga ttcttctaaa atttagaacg     240

aaatgcatga tgtatacttc cataatggga aagcacttgg tttttttggt tgcttatttt     300

tgtgcatacc gaatcgtcat attttaatct ttgctactat ggc                       343


<210> SEQ ID NO 247
<211> LENGTH: 363
<212> TYPE: DNA
<213> ORGANISM: Pinus taeda L.

<400> SEQUENCE: 247

attattttta tgtaggcttt gattatattg gttcccctta gactcctata tatagaaagg      60
```

```
aggtcttgtc atttgtatca tcaaaaaatt attcacttat gtaatgtaaa ggaggttgcc    120

ttcgaagtgg cttattttga attcgttgat ccatctcttc aatttgcgag ttggtttcat    180

aacatgacta ccttggcaca ttattccatg gcgtctatca tggatattat tatattattt    240

tttgttgata gagtttcatg tggtgcaaca tagtcctcct cattatctca tttgaagaga    300

taaaaataaa taaataaata aataaataaa taaattgact acaaaattct tcatccatgt    360

tat                                                                  363
```

<210> SEQ ID NO 248
<211> LENGTH: 398
<212> TYPE: DNA
<213> ORGANISM: Pinus taeda L.
<220> FEATURE:
<221> NAME/KEY: unsure
<222> LOCATION: n at 298, 324 and 385.
<223> OTHER INFORMATION: n is a or g or c or t/u, unknown or other.

<400> SEQUENCE: 248

```
acaagacttc aaagttgtct aacagccctc caagaccaag attaatgcct caaaacaagc     60

ctattaaagt ttgcaaacaa aacgataagg atatgttcac atcggctcca aataaataaa    120

taaataaaca aaatgtatta atatatgtca tgttggtttg atgcatagac acatcggttc    180

ataaggtaat gtcgactcaa ttgtatgtgc acagccgtta taaataccct gttggggtat    240

ttgcaaatgg gcaagaaaga attcacatga aatcttcgca taagggagcc ataatgaang    300

gagccacaat caaggttgat gganccgtaa tccaggtcaa aaaccacagt tagggtattg    360

actgccccgt gtttttgggt tttangtgca atccatgg                            398
```

<210> SEQ ID NO 249
<211> LENGTH: 313
<212> TYPE: DNA
<213> ORGANISM: Pinus taeda L.

<400> SEQUENCE: 249

```
atcaagaatg ggggatgatt caccattttt ggagtaaaag gataaaaata aataaataaa     60

taaaaataaa accttatttt caactcgtat tttcaactta tctctttacg attttactca    120

aatttcaagc agaagcagtt gttggatgca aaatttaatt ttacatccaa aaaataccca    180

tgttgcatac tttcaatgga ccctactaca cagaaaatgt gaaatacaag aaataatgtg    240

attgtaatca tgtttttttca tgtatttcat atttttcatg tagtggggtc cattgaaagt    300

atgcaacatg ggt                                                       313
```

<210> SEQ ID NO 250
<211> LENGTH: 434
<212> TYPE: DNA
<213> ORGANISM: Pinus taeda L.

<400> SEQUENCE: 250

```
ccatcttata ttatcctcca aaaaaatttc ctctctatac tttaggaaaa aaattatgta     60

tctactcaaa gtgcttgggc acatttgcta atataaatat atggttagtg ttataaaaac    120

aatttattta tttattttat ttttatttat ttatttattt atttattttc gtgggaatga    180

gcatggcatt caagccatca cgtggatgct tgcaagaagg agagttgaat ttttaagacg    240

tgaaaaatga ggtggctgag cagaagatgt aattgggtga tttgttggca gatagaaagg    300

gaaggggaac cctccatctc tgctaaatct gctagagaag agtaaaagca atgcaacaaa    360
```

-continued

```
gggacataaa cgaacaactg gaagcaactc agatgtggac catggtttgg aggaggataa    420

gaaccaattg gagt                                                      434


<210> SEQ ID NO 251
<211> LENGTH: 587
<212> TYPE: DNA
<213> ORGANISM: Pinus taeda L.
<220> FEATURE:
<221> NAME/KEY: unsure
<222> LOCATION: n at 401, 447, 466, 474, 488, 492, 497, 520...521, 529,
      530...531, 537, 544, 563 and
<223> OTHER INFORMATION: n is  a or g or c or t/u, unknown or other.

<400> SEQUENCE: 251

acgcactatt aatgaacacc aacaatgtat atgtagatta cttgattttt cacaattcta     60

taaatttatc taaatcatta tattattcgc catacattat gcaataacca tgagcagtat    120

catcataata gaatataagc acatcatcaa cacatcaaca caaaattcat attgacaccg    180

gatactgagg tggaaaccta atttgggaga aaaccattgt tgttgttgtc tcttattatt    240

attattatta ttattattat tattattata aagaaaaatt cttcttacat cttgcacaat    300

cacagactct tacgaggttg cgggctccta cctacgggag gctacaacct ctaaaaatta    360

tccagctcca actggaaagg aactactact ccctaatcaa ntttaccagc tcctactgaa    420

aggaactctt actccctccc taaaggntcc atccccatac cttttnggaa aaanttccta    480

atcttaaanc cnctggnggc ggtactatgg atcgaaccgn ncaactganc nnactgnatt    540

tccnatgtcc caatactggg tancnggcna ctgtcccttt taatgtt                  587


<210> SEQ ID NO 252
<211> LENGTH: 339
<212> TYPE: DNA
<213> ORGANISM: Pinus taeda L.

<400> SEQUENCE: 252

actttatata gcatttaaaa acacaattta aatgatgaaa agtcacacat tgtatattta     60

aaaagacata agcaccctag attcattagg atctatcaag ccgtatgagg gacacaattt    120

ttttttcta attttgcact ctaaaacagg tttgcaccca atgtgatttg atccctctag    180

gcgcatgcta gatctgtgat taaaatagac ctataatggt atattttcca ttattattat    240

tattattatt attattatta ttattatata tctggttaat tttcactatt ctcatattga    300

atttcttttc aagatttcca aaatataaaa ttaaaatgt                           339


<210> SEQ ID NO 253
<211> LENGTH: 385
<212> TYPE: DNA
<213> ORGANISM: Pinus taeda L.

<400> SEQUENCE: 253

acatcacaca accaaaatta aaacattcat aaaaattaat taaattaaat tataatttta     60

ttattattat tattattatt acataaacta atgaattaaa tatatataca ttcaataaca    120

caataatgac taattaaatt ttattttaaa ataaaccaac ctatccacat tctaataata    180

ataataataa tatccatttt taaggtcaca gccaagccag acaccaaatt ggtgtatgag    240

accccccttgt ttgtgggaca agggacccac ctccgcgcag cgatttgact gctaagtcta    300

cgaaggcata catactcttt accccctctg ggttttgaac cctgtgactc cttaggaagg    360

aaacacttga tcttaccctt taggg                                          385
```

```
<210> SEQ ID NO 254
<211> LENGTH: 322
<212> TYPE: DNA
<213> ORGANISM: Pinus taeda L.
<220> FEATURE:
<221> NAME/KEY: unsure
<222> LOCATION: n at 291.
<223> OTHER INFORMATION: n is  a or g or c or t/u, unknown or other.

<400> SEQUENCE: 254

cctggaaccc taatggtcaa gtgccccagt tgagaagtga cataagtata atgatgcata     60

tgttgtgtat atagcactat cacctccaaa tttatacgaa accccgagtt gataaagtaa    120

agttggtagc cctaggagtt gcaacatctt tgttgcaata ctgaggttca tcacttttct    180

tcttcttctt cttcttcttc ttcttccttt tcttctgcct ctattttgtt tgtctctact    240

tcctattttt cttctacttc ttcttcatct tcttcctctt caacactaga ngtangggtc    300

ccaccatgtt caagggctta gg                                            322


<210> SEQ ID NO 255
<211> LENGTH: 559
<212> TYPE: DNA
<213> ORGANISM: Pinus taeda L.
<220> FEATURE:
<221> NAME/KEY: unsure
<222> LOCATION: n at 490 and 492.
<223> OTHER INFORMATION: n is  a or g or c or t/u, unknown or other.

<400> SEQUENCE: 255

atctggtaat tctgttatga tcatgattat gctgatgttt atatatgtat acatgtaggt     60

gtgtatgtat gtcatgtttg atggggtcgt catggatcat gattattaac actaacattt    120

ggtgtgtgtg tgtgtgtgtg tgtgtatgta tgtcgttgtc tgatgggatg atgattgttt    180

tatgctaatg attatatatg tatgtatcta tttatctatg tcattgtttg acaggattgt    240

cagggattgt tcttgtggcg gtattattgc ttatgcaggt gaattgaatg aagaagttcc    300

tggtttatga agactcgtgt aggaagagta atcatgacaa atatatgagg tcaatatcat    360

gtggttatga gttgatatta tgtgattata ttatgtatat gttatggata tggtatatcg    420

agggatacat caacgaaatg aaagaagtgt gatctacgac atgcttggga aaaagcatgg    480

ataagacacn anaagcaagg tttattggta aggatggggt ggttttagat gtatggtaat    540

actattttgc atatgttgt                                                 559


<210> SEQ ID NO 256
<211> LENGTH: 406
<212> TYPE: DNA
<213> ORGANISM: Pinus taeda L.
<220> FEATURE:
<221> NAME/KEY: unsure
<222> LOCATION: n at 43 and 406.
<223> OTHER INFORMATION: n is  a or g or c or t/u, unknown or other.

<400> SEQUENCE: 256

ccaatcacca tatagccacc tgtcagcttc catcgttacc acnaaaatag tccccatcta     60

agcagttttc ctcagctttg gaatttgtgt ccccaaatca actcatttaa tttgattaag    120

gttataatat ttataataat ggaaaatgca actgggatat tacaaacctc tccccccttgg   180

tggaacaaca tacttagtga tcgatgacac ctatacaaca caaacaaaaa agatatgctt    240

aaaagtccaa acacaattga gatggagctt tatatataga tgtgtgtgtg tgtgtgtgtg    300

tgtgtgtgtg tgtgtgtgtg tgtgtgtgtg tgtatagaga gagagagata catctcactt    360
```

```
tataaattcc gccattttcc aatggcccct ttttgtagtc ttctan                406


<210> SEQ ID NO 257
<211> LENGTH: 279
<212> TYPE: DNA
<213> ORGANISM: Pinus taeda L.
<220> FEATURE:
<221> NAME/KEY: unsure
<222> LOCATION: n at 268.
<223> OTHER INFORMATION: n is  a or g or c or t/u, unknown or other.

<400> SEQUENCE: 257

gctagtaaga ataactaatt atgtgatcaa aattgtgtca tgtaaatgtt ctagtttcta     60

ccaaaatttg aatctttatg tctgcatttc atttttgcgt gtataatttg tgatatgtgt    120

gtgtgtgtgt gtgtgtgtgt gtgtgtgcgt gtgcgtgtgt gtgtgtgtgt gtgtgtgtgt    180

gtgtgtgtgt gtgtgtgtgt gtgtgtgtgt gtgtgtgtgt ctacatgtgt aaactctcca    240

tgtcctatgt cantgtgtct ttagactntg gatgtgggt                           279


<210> SEQ ID NO 258
<211> LENGTH: 369
<212> TYPE: DNA
<213> ORGANISM: Pinus taeda L.

<400> SEQUENCE: 258

cctcttcaat ccttaagaaa atgaggattt tcccttgaaa aaggagtctt aagccttaag     60

gccaaatcgc aatcggaggt tgcatgaggg cagacttaag gtttgggccg tggaaccccc    120

gatcactaat ctctgatcaa atcagattgg tggatcggag gcaatcacct tcagtggtca    180

tatatatata tatctatata tatatatata tgtgtgtgtg tgtgtgtgtg tgcgtgtgtg    240

tgtgtgtgtg tataaatgga tattagcgag tggatagtgt gatcagtgat tagccgaatc    300

ggcgaaaccc ttatcagtca cccggggcaa catatgtggg cgatgctgac gcgatcagct    360

gacgccgat                                                            369


<210> SEQ ID NO 259
<211> LENGTH: 357
<212> TYPE: DNA
<213> ORGANISM: Pinus taeda L.

<400> SEQUENCE: 259

ctcatatctt ctgactaatg caatatacaa atagtagggg tttttagctg tgtaatgtgt     60

tgattgaatt ctttctcttg tatgcttcat gatttctcga tcgattaatt ttttccacta    120

atgagtagag tagattcaag tattttgttt tagtaaatta caattagtag tttgaatcta    180

caaggaatac acacacacac acacacacac acattaacat aaccatgatc acaacacaat    240

taccattgct cataagttca aggctaagag aaattccttt atccacgcag agtatacata    300

atattgagaa cgacagttct caacatagcc aaggcatttg ttacctcaag cccatgt       357


<210> SEQ ID NO 260
<211> LENGTH: 451
<212> TYPE: DNA
<213> ORGANISM: Pinus taeda L.
<220> FEATURE:
<221> NAME/KEY: unsure
<222> LOCATION: n at 233.
<223> OTHER INFORMATION: n is  a or g or c or t/u, unknown or other.

<400> SEQUENCE: 260
```

-continued

```
atcggcggtt cgcaatcggt attggcatca gccatgccat atgggaaacc cccggcccat     60

gcgatacacg attgcaatgt cgcaatatcg tgtcgaaaca ttggaaagga gcggggccat    120

tatatatatg tgtgtgtgtg tgtgtgtgtg tgtgtgtgtg tgtgtgtgtg tgtgtgtgtg    180

atgcgatggc tagacccgac ggggctatag gtgatagttg atatattttt aaatatgccc    240

aacaacattt tgctatgtat ttcgcatatt tcgtttgata aatgaaatat gaagggaagc    300

actgatgcaa tgaaaacagg gcccgaaagg gtntgtgaat gaaatcatat atcgcttcaa    360

gtctgatatg ggttgttttg caagattttc caatgtttta atgcatttct ctgtgtaaac    420

agagaatggt tgttccaggg atttcaaagg a                                   451
```

```
<210> SEQ ID NO 261
<211> LENGTH: 409
<212> TYPE: DNA
<213> ORGANISM: Pinus taeda L.
<220> FEATURE:
<221> NAME/KEY: unsure
<222> LOCATION: n at 7 and 15.
<223> OTHER INFORMATION: n is  a or g or c or t/u, unknown or other.

<400> SEQUENCE: 261

cctcaangct aaganggctt tactgtaaat cataccgaga gaggtctttg taaaaatcat     60

gtgtgtgtgt gtgtgtgtgt gtgtatatgt gtgtgtgtat gtatgtatat taatatgggt    120

tactctgttc gagtaactgt actattgtgt ggattgaact tatgtttatg ttagaataga    180

tgtggcaggc acaaattaag ctcaagaggg atcaatgctc atatggaagt atataacatc    240

atcttcatag atatcagagc acacaacaga gggagaaagg ttacataacc aagattgcag    300

tgtcaagatc ttaagactga ctgtaaggtc gaggcataac agaggaggaa tttgtagaat    360

gggtgggaga aatctagatt aagccgaatc agagtggtgc aacacaagt                409
```

```
<210> SEQ ID NO 262
<211> LENGTH: 474
<212> TYPE: DNA
<213> ORGANISM: Pinus taeda L.
<220> FEATURE:
<221> NAME/KEY: unsure
<222> LOCATION: n at 369.
<223> OTHER INFORMATION: n is  a or g or c or t/u, unknown or other.

<400> SEQUENCE: 262

ccaaggccta tgttttgtga tcgaccctag tctcttgtgc atggtatcct acacttttca     60

tgtgtgtgtg tgtgtgtgtg tgtgtgtgtg tgtgtgtgtg ttttacatgt tccttgaggg    120

gtaagaaata ttttttggtc gtcgtttatc atttccatag agacatcgag tttctactct    180

ggcttagggt ccaaaattct agataaagtt atcgtactag ttgttctttc aaaaatttta    240

ttttcactct gtaaatagtc atatgggttt ataggttgca atctcttgtt catgaattcc    300

aattattaca aattggtaat gaaatatttt tgttctggtc aagggtccaa atcttggggt    360

attgtctana cggtattttt gttggtcagg ttagagtggt ttataagttc tctacccct     420

ctatagagaa tgacaagttg atgagggggt gcaagaatat ctacttctca atgt          474
```

```
<210> SEQ ID NO 263
<211> LENGTH: 537
<212> TYPE: DNA
<213> ORGANISM: Pinus taeda L.
<220> FEATURE:
<221> NAME/KEY: unsure
<222> LOCATION: n at 476 and 536.
<223> OTHER INFORMATION: n is  a or g or c or t/u, unknown or other.
```

<400> SEQUENCE: 263
acaagcctag ttcctacagt tggtctcact agtggtgtga ttcctactcc tcccctcatc 60
ctgcttccac tctgtacacc attaacacat tttttattct ctaaatctcc caaacaagac 120
acaatgttga aaccgtggtg ctctgatacc gcttgtaaca tgcaaagtca ccaaccaaac 180
acacacacac acacacacac gcacacacac acatacataa ttgtctctag ctcttgactt 240
gcactatcac ttatttatat ttttttaga gcatttgaat taattgacac acaactaaat 300
taattgacct agtcatagct agtcatggat acactttatg ttccttataa tgtggtaaat 360
ataacttata agtgtgaatg cattagcgac gaacccacct aatattaata gcactaaggg 420
aaccacgcta taattgtttg gattaatatt tggttgtcat attataatat tgggangtga 480
cctaccttaa aatgtttctc gaagggctct ttggtctcta gcaatcatac aaagang 537

<210> SEQ ID NO 264
<211> LENGTH: 494
<212> TYPE: DNA
<213> ORGANISM: Pinus taeda L.
<220> FEATURE:
<221> NAME/KEY: unsure
<222> LOCATION: n at 197, 462 and 486.
<223> OTHER INFORMATION: n is a or g or c or t/u, unknown or other.

<400> SEQUENCE: 264
atctgcactt agtgcttggc tatctggtcc ttaccagact tggccatttt tcttttttt 60 ttccttttct gtttgtcttc tatagcacaa cctaacttcc cccttttctt ccctttttcc 120
tagaaacctt tccagtcagg agagatagtt agggttgtaa ttactgcaac tgcttttccc 180
aacttcccat taagaanttg ccagcatttt tccaaaaaca tttcttatct tattaaagaa 240
ataataaaaa tattattaaa ctccaaaaca attaataata tcatattcaa tttttaacca 300
cagtaaattc aaatgtttac attttcctgg ggcattacac acacacacac acacacacac 360
acacacatat ataattacag tatgaaactg ttttttctct gaaaatcata gaaatcatgg 420
caatattttg ataaattatg gcagggattt ttgtaaatct angttatagt tgttaaaatt 480
caagantttg ggtt 494

<210> SEQ ID NO 265
<211> LENGTH: 361
<212> TYPE: DNA
<213> ORGANISM: Pinus taeda L.
<220> FEATURE:
<221> NAME/KEY: unsure
<222> LOCATION: n at 314...315.
<223> OTHER INFORMATION: n is a or g or c or t/u, unknown or other.

<400> SEQUENCE: 265
atcttttcaa tatttaacat tgaaaagcat taaagaatag cattttgaca actaagggtg 60
aatacccaaa ttcatacact cacgcatgag ctgagtcata agatctaaat ctagactata 120
ttgctaaaac acttagtcat cacttttgat tatgattgta gaaattaaac ttttaatatt 180
gttactttca ttgtgtgtgt gtgtgtgtgt gtgtgtgtgt gtgtgtgtgt gtgtgtgtgt 240
gtgtgtgtgt gtgtgtgtgt gtgtgtgtgt gtgtatgctt agcatagtgg gaaacacaaa 300
tagactttag tttnngactt gttgtatgaa ttatctctcc ataatataaa tgcagacaac 360
t 361

<210> SEQ ID NO 266

<211> LENGTH: 465
<212> TYPE: DNA
<213> ORGANISM: Pinus taeda L.

<400> SEQUENCE: 266

```
atcatttcac cattactgtg aaccaattgg aaactttgca aaaggatgta gggagcatcc     60

acacgtctac ggaggtcatt atgacgaggc tacaaaattt ggaccgaaag gtcgagaacc    120

tcaatgagag ggtggagatt gttgtggtgc ctatcctcaa agaagttttc gcacttgagg    180

agggtgcacc agtgatcact ttgaaatggg acttccctct ctagagctca caatgcaaat    240

ggagatgcag caagatgcgg agcaacagga acctaaggtc gcaggtcaat tgcgagttgt    300

agaataggaa gaagtggaag atgaagtgca acaaccaacc gagggagcta aattgatgca    360

attcaagagt ggtttttgt ttgtgtgtgt gtgtgtgtgt gtgtgtgtgt gtgtgtgtgt    420

gttttgaaag tatgttgaag tgaatgtcgt ttttttggag aacgc                    465
```

<210> SEQ ID NO 267
<211> LENGTH: 486
<212> TYPE: DNA
<213> ORGANISM: Pinus taeda L.
<220> FEATURE:
<221> NAME/KEY: unsure
<222> LOCATION: n at 384 and 444.
<223> OTHER INFORMATION: n is a or g or c or t/u, unknown or other.

<400> SEQUENCE: 267

```
actagaggca cacagtggga gtctcagatc ggatccaccg actacttagt aatgttgcac     60

gagttgtctc gtgctaccat gaccaccatg ctgagtagtt cctaggaata gcacttacat    120

atttttcgag gcctgtgtgc cacggatgta tgaggcttac gagccactaa tgttatttta    180

gacacacata ttattttttg ggttctgat atatcaaaca ttctcatcat atatatatat    240

atgtgtgtgt gtgtgtgtgt gtgtgtgtgt tggcttgttg gggcctaacc taggtttaga    300

agaggtttag ccaaacaaat cccacactac tggccctttc agcaacaatc cacagagcgt    360

ggactgaagt ctcacccgag gtantatggg agggtgctgg aaccaagttt ctccaccctt    420

ggtatgtctt gatgtggtct gganggatcgc aaaccattct gcactcctac acttctctgc    480

acagat                                                               486
```

<210> SEQ ID NO 268
<211> LENGTH: 446
<212> TYPE: DNA
<213> ORGANISM: Pinus taeda L.

<400> SEQUENCE: 268

```
atcaacattg gccgtgccat atggcttacc tcgggtccac gcgatattgc gatgcggcga     60

tcaacataat ggagcaggta tatatgtgtg tgtgtgtgtg tgtgtgtgtg tgtgatgtga    120

tacatatatc tggacccaat gggtttatga atgcaaatat atgatacttc aagttcacca    180

taaggtcctc tgatgggatt tttcaatgtt taatgtattt ttaaaataga aagggaaccc    240

atgtaacagg gcatttgtga caagcgatag caatttaaaa ggcaaacata atggaaaaaa    300

atgtagagtt cataattttt gaaatctgat agacgcgttt gggcaaattg ttacaggctt    360

tctgtgtatt ttccagtgta agccgagaat taccatcttt gggatttcaa gggcactgat    420

ggtccattcc attacggaat aagtgg                                         446
```

<210> SEQ ID NO 269
<211> LENGTH: 514

<212> TYPE: DNA
<213> ORGANISM: Pinus taeda L.

<400> SEQUENCE: 269

```
ccttgtggaa gccacaattt gttgagtatt ggcaattatt gaaaaaaccc tttcaagctc     60
ttgaatctgt attcgtcctc ttttgaacga gtctctctct ctctctctct ctctctctct    120
ctctctctct ctctctctct ctctccacac acacacacac acacacacat attcatgggt    180
atgttcaact ttgatgtgtt tgttttgttg catggtttta ttgcaatgac tttgcttccc    240
tttgccaagg taaagtttaa attgcttatc cgtgtttatc atattttctc atgctagatt    300
tctttacgag aatcgggggt taactaagga attccttttg tctcatcgca ggttagtttt    360
ggcaatatgg gcacgttgaa tccgacaagt tttttggaac caactactca taattcctct    420
tctttcgcgc aactatacat gtgcttatct atgtttttttg ttttcttcaa gtcatagaag    480
ccactcangg ttccaactca tacactatat acgt                                514
```

<210> SEQ ID NO 270
<211> LENGTH: 538
<212> TYPE: DNA
<213> ORGANISM: Pinus taeda L.

<400> SEQUENCE: 270

```
ttgagatgag tagtgtgggt ggtggtctgt tgtagggagc agaacccacc acagtagaca     60
actaggtttc tttttccgct atttttgaga gacatgtgtc tcagatgtat cacgaacaca    120
tactctattt tttgacatac acactatttt tgagaatgtc cgtgcgccac acgatatata    180
tatatacaca cacacacaca cacacactat ctatggttta ttactgtcta aatgcttgca    240
tacaatgttt tgattataaa ttgcataaat gtctatctaa tacatgattt tgcaatgcat    300
cagttaacgt gtttaatctt cttggaatgt gtttatatgt gatgaaatca aaatttcttt    360
ccaataatct aacacgcaaa tacaacctta aaatatgagg gtttctgatg gaataatgcc    420
cgttaagctg cagagcgaca agttaagaat ccaggttcac aaccaatgca tgaatatcga    480
ggttaacaac ctcagtcaat agttcaatga cagtgctatc agcgacgttg tttgcggt   538
```

<210> SEQ ID NO 271
<211> LENGTH: 483
<212> TYPE: DNA
<213> ORGANISM: Pinus taeda L.

<400> SEQUENCE: 271

```
atctctccac agctttagag acacattgtg ggggtatagt cctctcatta tgaaggactc     60
ctatgacatc tttttcatgt tcttttgtgt tatcaccaac atagaggaga ttaactcctt    120
aggatatttt ttatgggata tgtctttgca tatgtattgg attatgatcc taagccttag    180
aaacccttat tttgactaat gtatgcaaac tatatttttg ttgtaaaact cttttttgat    240
atatgtgtgt gtgtgtgtgt gtgtgtgtgt gtgcatgtgt tttagcttca atattgttca    300
cttgtgaatg ttgtcttatg atgttttcat ttaggtttct aatgaatgta tcatatgcat    360
gggtgacaaa attaatgtga caaatgtcaa tatatgacac aattagccaa tgaataagct    420
aatgttttag agtctagtaa tataaatgta tgaaatggta taaaatccca ttctagcaga    480
tgt                                                                  483
```

<210> SEQ ID NO 272
<211> LENGTH: 521
<212> TYPE: DNA

<213> ORGANISM: Pinus taeda L.
<220> FEATURE:
<221> NAME/KEY: unsure
<222> LOCATION: n at 434.
<223> OTHER INFORMATION: n is a or g or c or t/u, unknown or other.

<400> SEQUENCE: 272

```
atcatttatt tcaaaacatg taaaaaaaat aaacatgtag gagcacaagc cattgattat     60

tttctctatt ttttaaagga agacatttaa cttaaacatt tgtagtcaaa atcaactgac    120

tttcaatagt attttttaat tattattatt attattatta tttattatta ttacactttt    180

ttctatcaaa cggtccaact gtgttaagtg tctaatacat atgcctaatt tttatatgct    240

aacattgcaa tactacttac taattttggt tgtgctatcc atagaagcat ttggtaagtg    300

ttcatcatgc aatattttta ccatacacgt tatgattgca tgtccatttt caagcaagtt    360

ttcaaaagag atggttatag atataattct catatgagtt gtaggatagt gttccagcag    420

tttgcaccca tganggaact atcatttaca atgaaactac aaaacatgtt ggcattattg    480

acttgtttaa cactacatta ttaattgtta tatgaaaaat t                        521
```

<210> SEQ ID NO 273
<211> LENGTH: 451
<212> TYPE: DNA
<213> ORGANISM: Pinus taeda L.

<400> SEQUENCE: 273

```
atctttcgat gtctattggt atactatttc aacagagggt gtttgcaaat catggggtaa     60

aataataata ataataataa aataagaata aactaacttc aagacaaagt tccttaaaga    120

gggagagtat gtaatgcccc ataacaacaa caacaacaat aataataaat gacaataaag    180

taaataaaat atttttaata tataaataga ataataatta acaaagaaaa gataaaataa    240

caattaacaa gaaaaataca tgaatataaa aataaaataa caaataacga agaaaatata    300

ataataaata aataaactaa aaattggcat ggacactggt gggctccagt attgtagcaa    360

taatgctata actcctggga ctcccttctt tacttttatc aacctggtag ttcgtaacaa    420

acttggaagt gacagtgttg tatgcacaag t                                   451
```

<210> SEQ ID NO 274
<211> LENGTH: 341
<212> TYPE: DNA
<213> ORGANISM: Pinus taeda L.
<220> FEATURE:
<221> NAME/KEY: unsure
<222> LOCATION: n at 86.
<223> OTHER INFORMATION: n is a or g or c or t/u, unknown or other.

<400> SEQUENCE: 274

```
ataatggcct tggtgggctt aatggttaag aacatgtatt tccttgtaag aggtcataga     60

ttcaaatcta gagggaagta gagaangtaa acctccacag actttagtag tcaaatcact    120

gtaaggaggc ggatcccttg tcccagaaac aaggggtctc ataaaccaat tttgtgtctg    180

gcttggccat gacctaaaat tagattatta ttattattat tattattatt attattcaaa    240

gggagaatct agctctgttt gtaaaaagta tctaacccag gcataacatc aacataaaac    300

caacttgtag tagaagtatg ttgaagattt gttttaatat a                        341
```

<210> SEQ ID NO 275
<211> LENGTH: 382
<212> TYPE: DNA
<213> ORGANISM: Pinus taeda L.

<400> SEQUENCE: 275
acattatgca ataataatat tacacaacca aagtaataat ataacttgag tgggcataat 60
ggttaagagc atgtgtttct tcctaagagg tcacatattc aaaaccagag gggggtagag 120
tatgtatgcc ttcgtagact tagtagtcaa atcgttgcgc agaggtgggt cctgtgtccc 180
acaaacaagg gggagggggt ctcatacacc aatttggtgt ctgacttggt cgtgacatta 240
aaattggata ataataataa taataataat aataataata ataatattgt caacccacct 300
aattaattat acttcattag ttgattctcc aagaaataca tcctctatgc acatttttct 360
agtttcatga gtaaaaaaag gg 382

<210> SEQ ID NO 276
<211> LENGTH: 314
<212> TYPE: DNA
<213> ORGANISM: Pinus taeda L.
<220> FEATURE:
<221> NAME/KEY: unsure
<222> LOCATION: n at 193, 214 and 281.
<223> OTHER INFORMATION: n is a or g or c or t/u, unknown or other.

<400> SEQUENCE: 276
ctcctgagtg gtcccatact taaaaataaa ataaaataaa ataaaataaa taaataataa 60
ataaataata ataataataa taataataaa ataaaagggc tccaacaggc ctcatatcca 120
tctttgttat caatcagtgc accactttag tctccatgta tgcccaacat tctatatgtt 180
agaatctttt tanattcgtg acaatgttca ctanatcccc atatttcaaa tatttcttgt 240
gctaacaacc tcttgatgat ctttattgcc atggaatgaa nagtgcatct ctttttcaaa 300
ttgaattcat aaac 314

<210> SEQ ID NO 277
<211> LENGTH: 547
<212> TYPE: DNA
<213> ORGANISM: Pinus taeda L.
<220> FEATURE:
<221> NAME/KEY: unsure
<222> LOCATION: n at 77, 279, 380, 384, 404, 468 and 513.
<223> OTHER INFORMATION: n is a or g or c or t/u, unknown or other.

<400> SEQUENCE: 277
tatgtgtatt caatgttatg gactaggaag gcttcaacat cactagaata cccaattttc 60
tgaagaagaa aacgtantct ancaatgaat attgtcaact aaatttggat tggacctgaa 120
tcaatagatt gttctttatt caagcgaaaa aataaataaa taaataaata aataaaaata 180
aaaataaaaa ttgatgtgct agttgtagac aaggacatta agatgaaatg gaaagaggtc 240
aatatgcatt tgcaggaact tttggggaaa acctcgaana ctgccaagtc tatctgaaca 300
ttcacaattc cagcttatat cggattgcat gcaagcatcc cgtgttccca tgtgcagaca 360
tgatacattg gatcatctcn cacnctgatc ttgagatgat gacnttgaga agtgtccttg 420
ggatagagat tgttaccttc aaggcatagg attatccnta gatgttatcc atatgtcaag 480
acccagtagt cacccatgga agacaccctt cancataccc caaccaacaa tgccaactcc 540
aggggat 547

<210> SEQ ID NO 278
<211> LENGTH: 352
<212> TYPE: DNA
<213> ORGANISM: Pinus taeda L.

-continued

<400> SEQUENCE: 278

```
tagtgttcct ctcaagtgac cccttttcc taaacaaatt tgaagtatat cccacattta     60
cccttgcatc ctgcacaagt atatcaactt ccctaatttt atttatttat ttatttttat    120
ttatttattt atttttttct gtcttctctg ggtggttctg tgtgagtgga tgtctccact    180
ctcttctcct caatttgtgg cttctccaca acttcccgag gctcatcctc tagggctaaa    240
atatcctctt ctggtggaat ctgaagctcc atcttaagag agcactaaat ttctttctcc    300
ttatcaaact ttacatccct ttgcacaact tccattatga gggaaggtaa gt            352
```

<210> SEQ ID NO 279
<211> LENGTH: 510
<212> TYPE: DNA
<213> ORGANISM: Pinus taeda L.
<220> FEATURE:
<221> NAME/KEY: unsure
<222> LOCATION: n at 181.
<223> OTHER INFORMATION: n is a or g or c or t/u, unknown or other.

<400> SEQUENCE: 279

```
attccatgtg aggactttca gtgagaatat tttaaaacta tatcatctcc cacttcttgc     60
aatgaaacct ttctagtttt ccttcctttt tttttgcttt ttttaaccaa ttctttgact    120
aaaacatcgt tacctttctc tatgaattcc tctatggaat gtattcccgg ttccttcaaa    180
nattttattt tatttattta tttatttatt ttttcctttc aaacaaatcc tttggataat    240
gctcacattt ctcttcagac aaattcggca aatatctctc tacccattca ttgaggaggt    300
ccactaaaac actttcttcc ttggaaaaat aatcataatt atgtcttatt aatcgagcaa    360
cctcctcaat atccgggagg taagtaacaa taattttctc attacccct cttcatattg     420
tgaagtcttc ctcttcaccg gttgcttcat ttccttcaca ttctgggttt gttccatcat    480
ctatacatca tttggtttcc tctttagggt                                     510
```

<210> SEQ ID NO 280
<211> LENGTH: 445
<212> TYPE: DNA
<213> ORGANISM: Pinus taeda L.
<220> FEATURE:
<221> NAME/KEY: unsure
<222> LOCATION: n at 222.
<223> OTHER INFORMATION: n is a or g or c or t/u, unknown or other.

<400> SEQUENCE: 280

```
acctacggtt gtgaaaaanc gctactattg gccgaatcta ataaataaat aaataaataa     60
ataaaggaag gttgttggtt tcatcactag gtgtttggat tgtcgatagg taaaagtgga    120
gttcaagcat ccaaatggtc tattgcaacc aatttcgatt ctagagtgga aatgggaggc    180
catttccagg gatttcctca caggtttgcc aagaacatct anatagcatg attccatcat    240
ggttgtggtt gacaggttga ctaaggtagc tcacttcata atagttaatt ctacttatat    300
agctagttag gtagctcgag tcgtcgtcaa ggatatagtt aggttacatg gtattcctaa    360
gaagatattt gacaaagata ccaagttcac ttccaggttt tggaaggaat tatttgcagg    420
tttgggtaca gaattgccct ttagt                                          445
```

<210> SEQ ID NO 281
<211> LENGTH: 750
<212> TYPE: DNA
<213> ORGANISM: Pinus taeda L.
<220> FEATURE:
<221> NAME/KEY: unsure
<222> LOCATION: n at 8, 12, 47, 96, 111, 349, 506, 530, 581, 601...602, 667, 689, 702, 711, 738, 744
<223> OTHER INFORMATION: n is a or g or c or t/u, unknown or other.

<400> SEQUENCE: 281

```
ggatatcnag antcgaggat catgcatact agcttgtcca acggggnagt tggcgctagg     60
gaaccgcaag acttgccaaa acagcggagg ctttanccat gagtggaccc nggtgaaggg    120
gatgattgcc ttcacaaaat ctatagggga atcgaatatc cccttttccc tttccatgac    180
caactacgga ggtagcatcg ccgtgagctt cagtggaaga tgaaggacgg gctggatcac    240
gggaccatac ttctaagacc ttcggaatgc caggacaatc acgaagaaga tggtcctcct    300
tccataatag acaaggaaac ttaaccttct gcggaggagt gggaaggant canacttcta    360
atgtctgtga tggagcaaca gttgtgcatg tagtctctgt tgtgttggta gcctctccct    420
taggagactt cttcttcttg gtcttcttct tcttcttctt agccacctgg ttactcgact    480
cgaagacttt caccaaggcg gagtangctt ggcgttaatc atggtcatan ctgtttcctg    540
tgttgaaatt gttatccgct cacaattcca cacaacatac nagccggaag cataaagtgt    600
nngcctgggg tgcctaatga gtgagctaac tcacattaat tgcgttgcgc tcactgcccg    660
ctttccnttc gggaaacctg tcctgccanc ttgccttgaa tnaatctgcc ncccccngg     720
gaaaagcngt ttcntntttg ggcgctcttc                                     750
```

<210> SEQ ID NO 282
<211> LENGTH: 233
<212> TYPE: DNA
<213> ORGANISM: Pinus taeda L.
<220> FEATURE:
<221> NAME/KEY: unsure
<222> LOCATION: n at 22 and 60...61.
<223> OTHER INFORMATION: n is a or g or c or t/u, unknown or other.

<400> SEQUENCE: 282

```
tcaatcacca attatttggc tntctaggtg tttttttca tatacctaga tcgagtcttn     60
ngcctttgaa attcttcttc ttcttcttcc tcttcttact cttctcctcc tcctcctcct    120
ccttcatctt cttcttactc ttctacatat ttgaaatcag attcttcatc ttcatctaat    180
ttctcccctt ctttagactt tgttatatgt ggcatagttt catccactcc gac           233
```

<210> SEQ ID NO 283
<211> LENGTH: 570
<212> TYPE: DNA
<213> ORGANISM: Pinus taeda L.

<400> SEQUENCE: 283

```
cctctatttg aaatgtgatc atcatattgg acttataaga ggtaacatat aacatacatt     60
tccaaaactt tcgtaaggag atcaacactc tccaaataat taggaatccc tccttctaag    120
gtcaatcata ggcataaacc atggatataa atacatgatt gataatatta agawcttatc    180
aacattccat tcttgtggat ggtaattcca tagatgggtt gtatagatgg ttatcaccca    240
cccatgtcta tagacttggt gacccctgaa gagcctccaa tactcatacc actcactgca    300
atacctccaa tgcataatgc aaccacacat gtggacatgt ggacatgtgt atgtgtgtgt    360
gtgtgtgtgt ttgtgtgtgt gtgtgtgtgt gttctcctac ctaatggatg aagaagcatt    420
accctatgaa aggtttccag gaaactcatt aacaaaagta accaacattt gtatacccac    480
aagtggagtg tcaatcagac tgagcaccat ggctataacc atccattcaa gcaagggttt    540
caccacgtca tctcaacact gagacaacgt                                     570
```

<210> SEQ ID NO 284
<211> LENGTH: 395
<212> TYPE: DNA
<213> ORGANISM: Pinus taeda L.

<400> SEQUENCE: 284
atcagatcat ttttcaaata cttagactag atgggctaga tgcatgttgt taagcatgca 60
ttgtcatggt tatggttgtt gtgcacgagc ttattgtatg aagttagtgt tatcatacat 120
gatgtcgata tgttgaagtg agtgtgtgtg tgtgtgtgtg tgtgtgtgtg tgtagatatc 180
atgctaatct agattgattt tgtaggtgag ataacctccc ttgaacttca ctgatgtatg 240
ttgattatgg ttatgtttgg tttatctaac aaggtatatt ttcagggaga agatcaaata 300
tgactagcac aatggtggat tatagttcac gtgactctcc ttataggtca catgaggagc 360
gcaaagataa gtagtgatgt gcctcataaa tgggt 395

<210> SEQ ID NO 285
<211> LENGTH: 485
<212> TYPE: DNA
<213> ORGANISM: Pinus taeda L.

<400> SEQUENCE: 285
atcatataac tgctcattgc aataaggaat tggtgattca tgtggtaata aaataattgc 60
ccactacatc tttgtgactg cgattaaccg catcgattaa cacacacaca cacacacaca 120
cacacacata tatatattgg ttatgtctca atataaccat tttataatatg atttaacttg 180 gtcacatggg tataccaggg ccgattcttt tatacttgtt cttttagcga ttccactatg 240
ccattatcac ttcttcatct tccttttttat cttttttttg aaatattttc aagtaattct 300
tgaatgaaaa atgaatacta caggcaacaa aaatgcatgt tacaataggt tccatgctca 360
ttattaatgg tcttttaggt aaaagcatgc ccttcatgct tctagggctg gttgggtctg 420
tggatttatt gtcacgagtc aaaggactca acatcatgtt gataagaccc ttctcagcaa 480
aatgt 485

<210> SEQ ID NO 286
<211> LENGTH: 438
<212> TYPE: DNA
<213> ORGANISM: Pinus taeda L.

<400> SEQUENCE: 286
atcttgtcct taggctcaaa tctgaacaca acactcaaac atgctcaatg tctcttctcc 60
taaagaacaa atctgaataa agcactcaaa tatgctcaat gtctcttctc cttactctat 120
aacaacctct ttttctttaa ttcaatcatt gtttctcaca caacacacac acacacacac 180
acacacagaa acatctatgt ttttcttagt tgggacctca catcctcttt tgcattaaaa 240
gcatcacttc aaatttgtgt ttatcacccc tacctcctga cattctctag gactatgctt 300
caacacttat ttttctcacc attcaagtcc tcaaagcctc ttgtcactca tcaactttgt 360
ttctttcaac tatatccaaa tcctctttta cattatatat cctttgtagc atttttttcc 420
ttatctcatc accgtagc 438

<210> SEQ ID NO 287
<211> LENGTH: 619
<212> TYPE: DNA
<213> ORGANISM: Pinus taeda L.

<400> SEQUENCE: 287
arkaagctta cacaacactg cacacacaac accagtactg cacattcgaa gaccacacta 60
tctttaccaa gcaaccttgc ttctagtgtc tttccactat ccatacttgt cccaacatgc 120
cacaaatcac aatgctttca ttctgttgat gtatccctca acatagcatg tccattacat 180
aaacataggc atagtgtaaa cacataatat caatcatatc cacatgatac taacatcata 240
gatctgttag ggatactctg cccacttgat tcctcacgat accaagaacc tcttcatgct 300
actcacatgc ataagcaatc attcctccac aagaatgatc cttggcgacc ttgtcataca 360
atgncataca tacatacata tatacatata arcatcatca taaaacaatc atgatcccta 420
atgacccagt tagacacaca cacacacaca cacacacaca cacacacaca cacacatata 480
taaacattag cataaaacaa ccatgatccc taaggaccct gtcagacaat gacatgcata 540
tatacatata tacatatata grcaccagca taataatgat cacaacataa ttatcagata 600
agcttgcatg cctgcaggt 619

<210> SEQ ID NO 288
<211> LENGTH: 408
<212> TYPE: DNA
<213> ORGANISM: Pinus taeda L.

<400> SEQUENCE: 288
cctccgtccg ctttgaatcc tcttccaagc attatacaat cattgcttaa tgccgaaagg 60
ggagtyggcc accatttctg taatgtaaga gtgcctcggg tctgayccat cggatcaccc 120
atataattgt gtgtgtgtgt gtgtgtgtgt gtccccgctc cattgtaaca tgtcgatgcg 180
atattacaat gcgacttatc gcaatcgcat atcgcataag cccgcagcct tcccatataa 240
catggtttat tgccaacgcc gattgtgatt gccgatctac ctaccaccac cgattgcgat 300
tgtcgatctg ccaacaattg catgtcgcat tagcctcaac cttttgttaa gtcctccctt 360
tggctttttg cgatgcgata aagcggtaat cgcatatcac aatgtttt 408

<210> SEQ ID NO 289
<211> LENGTH: 687
<212> TYPE: DNA
<213> ORGANISM: Pinus taeda L.
<220> FEATURE:
<221> NAME/KEY: unsure
<222> LOCATION: n at 168, 174, 206, 244, 353, 612, 615 and 673.
<223> OTHER INFORMATION: n is a or g or c or t/u, unknown or other.

<400> SEQUENCE: 289
gcatgattta atttccagta gtaatctccg ttttttattg tttgttaaaa tatatacgta 60
tttcaatatt cctttcccac ttgaaacatc ctcaacttaa tatcctgggt tggggtccga 120
ggatctcctt gccagtagca acttgcaaat tgcaacaacc ttcacaantt caanatccat 180
ttaaacaaac ctgtcatact catcanagga cactttacaa aattgccact aagcaactct 240
gganatgggt cagttttgca ttatctatac caactagcat agacccgtct tcaccctaca 300
tctattaagc attggaaagg gataaagaaa acaatgtgca aaccacttgg aanttggtgt 360
ttaaaaaacc cagggttaaa atggatctat gttagtttct tttatttact tattttttac 420
accacttttc ttggcacagg ttggacatct cttattcatt ttaagtttat gcacatcaca 480
cacacacaca cacacacacc tatgaaatct cccttccacc acaaaaactt ggcgttatca 540
tggtcataac tgtttcctgt gttgaaattg ttatccgctc acattcccca caacatacaa 600
cccggaaaca tnaantttta aacctggggt tgcctaatga attaactact cccattaatt 660
gctttgcccc acngcccctt tccatcc 687

<210> SEQ ID NO 290
<211> LENGTH: 335
<212> TYPE: DNA
<213> ORGANISM: Pinus taeda L.
<220> FEATURE:
<221> NAME/KEY: unsure
<222> LOCATION: y at 86.
<223> OTHER INFORMATION: y is t/u or c.

<400> SEQUENCE: 290
gtaggtcagg tcatgccatg gtaactcttc atctcatgtt taccctgata ggccagtgga 60
attaggtaac ttttggaggg tgtgtyacaa attggtatca tagattccaa gttcaaacac 120
ttggactgga tgggcgggat gtgattgtta tgcatgcatg tcagtcatat gcatgcattg 180
tagtagctat ggttgtcatg tatgtattca gtgttacttt ttgatttatc atgcatgatg 240
tcgatgggta gatatgttgg tgtcattata tatatgtgtg tgtgtgtgtg tgtgtgtgtg 300
tgttgttgca acaaacatcc tccaaaattt tgtgt 335

<210> SEQ ID NO 291
<211> LENGTH: 265
<212> TYPE: DNA
<213> ORGANISM: Pinus taeda L.
<220> FEATURE:
<221> NAME/KEY: unsure
<222> LOCATION: m at 92; and
<223> OTHER INFORMATION: m is a or c; and
w is a or t/u.

<400> SEQUENCE: 291
ccttaggaca ttctctacta ttgttatctt aatgttgtca ttagtggtag gatcattatt 60
tttaattgta tactttgtat ctaatacaca cmcacacaca cacacacaca cactatggat 120
attgttcaca cgaatcaata tttattaata agcggtaagc tatagargag gtttccttta 180
caaagaaacc wtttwattta atcatatttt aacattctca acaagtgaca tcgcttattc 240
tttatattat tattttttag ggtta 265

<210> SEQ ID NO 292
<211> LENGTH: 687
<212> TYPE: DNA
<213> ORGANISM: Pinus taeda L.
<220> FEATURE:
<221> NAME/KEY: unsure
<222> LOCATION: w at 364
<223> OTHER INFORMATION: w is a or t/u;
r is g or a; and
s is g or c.

<400> SEQUENCE: 292
actagatgtg tcctctagtc ccattgaact acttttgtgg tcattcgttg gaaattaata 60
aaattatctt atcttacctt taattactca tttattggca ttgaaatatt ttactatggt 120
cgatgtgtgt gtgtgggtgt gtgtgtgtgt gtgcgagtga gcgcgtgcat gtgtgtgtgt 180
gtgtgtgtgt gtgtgtgtgt gtgtgtgtgt gtgtgatttg gagataaytc ttccatgtwg 240
agtttacaat tagtttggaa ttttgttaag araaaatctc aacctccttg tctatttttg 300
gaatcaattg gatctcaatc caactatata tgtgtatcat atttatgaat gaataatcgt 360
tttwgatgtg tgaaaattag ctttatttgt tggtatcaaa gccctatggg tctggggaaa 420
cctgggcgtt aatcatggtc atagctgttt cctgtgtgaa attgttatcc gctcacaatt 480

```
ccacacaaca tacgagccgg aagcataaag tgtaaagccy ggggtgccta atgagtgagc    540

taactcacat taattgcgtt gcgctcactg gcccgctttc cartcgggaa acctgtcgtg    600

ccagctgcat taatgaatcc gccaaccccc sgggaaaagc ggtttgcctt attgggcgct    660

ctccgcttcc tcgctcaatg aatccct                                        687


<210> SEQ ID NO 293
<211> LENGTH: 393
<212> TYPE: DNA
<213> ORGANISM: Pinus taeda L.

<400> SEQUENCE: 293

gtctcttaat tatgttatga tcgtgattac attgctgcct atatttgtgt gtgtgtgtgt     60

gtgtgtgtgt gtgtatagat atatatatgc caatgtctaa tagggctgtc agggatcatg    120

atcttttatc atgatgttta tatgtatata tgtatgtctg tatgtcattt tctgacaagt    180

atggaagcga tcattgttgt ggaggagtga tttcttatgt aggtgaatga catgaagaag    240

ctcatgttgt caagtgggaa gagtatctcg aatagatcta tgaggttagt ggcatgtgga    300

tatgagttta tattatgtga ttatactatc ataggtaatg tcgagggata catgaatgga    360

atgagaaagg tgtgatttac aacatgctag aac                                 393


<210> SEQ ID NO 294
<211> LENGTH: 577
<212> TYPE: DNA
<213> ORGANISM: Pinus taeda L.
<220> FEATURE:
<221> NAME/KEY: unsure
<222> LOCATION: r at 410 and 494;
<223> OTHER INFORMATION: r is g or a;
      k is g or t/u;
      w is a or t/u; and
      m is a or c.

<400> SEQUENCE: 294

atcgcaatat agcattggaa cttcaccgaa gggcgaagct atacacacac acacacacac     60

acacacacac acacacacaa atatatatat atgcgatctg attgctggac ccaatagcac    120

cttaacacta tattcaataa atatttcaaa tctaagataa agccattatt atgggatttt    180

gcaatatttt aatgtatttc taaaatacaa atggacaagc catttgtgac tttcgacagt    240

gacttctggg tagacccaat aagagtatag actagattta aggacttttg aagtttgaaa    300

gactatgttt cggtggattt tcaccatttt gaatacattt ctccgtgtta acaaaaagca    360

gctattctag ggattttaaa gcctcgatgc actcatccat ttcagtttar gtkgccatct    420

cccctgaatg tgttttgcaa tgawtgttta acgttttgaa agaagaattt gattggatag    480

aggccgggaa amaraaagcc caataagttg gaaatgaata aggttaagaa atattggctt    540

taaaagccct tgaaaaraaa aaaaaaccga agggttg                             577


<210> SEQ ID NO 295
<211> LENGTH: 575
<212> TYPE: DNA
<213> ORGANISM: Pinus taeda L.
<220> FEATURE:
<221> NAME/KEY: unsure
<222> LOCATION: k at 351.
<223> OTHER INFORMATION: k is g or t/u.

<400> SEQUENCE: 295

cctagttgac aacgtaatta gtgtgccatg aacaatctat cacatgtgat ttgtatgatc     60
```

```
ctcttgtggc agcaccatcc aactatattg caaaatcaac gtcatcctga catgtctatc    120

aatacacatg ccaacacatg ccaactcctc catgaccaac atgctaccat aaagctccac    180

caatgccatc atctgatcaa catcaatgcc aatacatcyc aacacaaacc gtcatgagtg    240

atatcatatt attgacatca atgccaacat aatcaatcca atgtcaactc aactagtagc    300

ataatgacca tgttgacatt aatgcaaata ctataatgtc aacactatat kctataaatc    360

tatatcgatc ccatcaatag aggatgctaa gggttaggtt ggtgaggaga cttgggagtt    420

catagtgatg acacacacac acacacacac acacacacac acatgttttg tattattttc    480

ttaaattttc tttttcacat tgctattttt tttaatatta tacatatcat ccatattgga    540

attgttctta ggaaattttg tgtgtgtgtg catgc                               575
```

```
<210> SEQ ID NO 296
<211> LENGTH: 455
<212> TYPE: DNA
<213> ORGANISM: Pinus taeda L.
<220> FEATURE:
<221> NAME/KEY: unsure
<222> LOCATION: k at 2;
<223> OTHER INFORMATION: k is g or t/u;
      m is a or c;
      w is a or t/u; and
      s is g or c.

<400> SEQUENCE: 296

tkttaccccg aactccagaa aatgcagama ttgggacggc tcacatggct mtggggaggg     60

ctggagaagc cccaggaagg cacaagccaa gcaatacaaa tcgaagatga gcagtctgta    120

gaggccgawa tggaagaaga agacaatgag gaagcatagc aggctgcaga gacagaaaca    180

gaagaagaat acgactagga agcagagcas tctgcwgaga cagaaacgga aamagaagat    240

gtcgaggaag aagagcagtc tgcagaggct saagtagaag aagaagaaga ggaggcagag    300

cagtctaaag aggaaggaga cgagaaaaaa gaagctgagc ggtctkagca sgakgaagga    360

atggaacaac aggaaggtag cccattacca racccgttag gggaagatga attggccaac    420

attttggcct atatgggtga atatggaaaa ccctg                               455
```

```
<210> SEQ ID NO 297
<211> LENGTH: 711
<212> TYPE: DNA
<213> ORGANISM: Pinus taeda L.
<220> FEATURE:
<221> NAME/KEY: unsure
<222> LOCATION: n at 281, 673 and 703.
<223> OTHER INFORMATION: n is  a or g or c or t/u, unknown or other.

<400> SEQUENCE: 297

gtcggcagat cagaacggtg aaacaaaatg cagaggggct taaacacaca cacacacaca     60

cacacacata tacgctcgat ccaatggtgc aatcattgaa atcaacggat agcaatcaaa    120

gcattataga ggattagccg atatgttata agttatatac gtgattcgat ggactggact    180

cgctaacatt acaagccata ttgtatggat cttgagatcc atcaaacacc ccttttttaac    240

gtattttcac agtttcattt gttaaatgaa atgtgaagga gaaaggccaa ttgtgactta    300

cgatagcgac ctacgggtag acccgatagg aaaataaagc atagttatgg gaatttcaag    360

tctggaattg tgttttatgc ggactttccc atgttttcac agcattctct gtgtaaccaa    420

agaatgactg ttactaaggg attccaagtg ccgatttccc tcattcgttg caaaaacaag    480

tggaagctta tcagtagcat attatggctt taacatttga aatatgcaag ctcaagtttt    540
```

```
attcttcatg cttaagggaa aaattcttat atacaatata ngttcaagat atgccctctt    600

tatttaaggc ttatttaata tgatataggt catttaaatt ttagtattta tcctttacac    660

cattaacata acntattaat tgtgcatgta acccatggat aantagatta a             711


<210> SEQ ID NO 298
<211> LENGTH: 612
<212> TYPE: DNA
<213> ORGANISM: Pinus taeda L.
<220> FEATURE:
<221> NAME/KEY: unsure
<222> LOCATION: n at 264.
<223> OTHER INFORMATION: n is  a or g or c or t/u, unknown or other.

<400> SEQUENCE: 298

atcacaacag ctctcttaat agcctcggta tatatgtgtg tgtgtgtgtg tgtgtgtgtg     60

tgcgtgctcc ttcatggttt caatattgat gaaagtaaag tcacagtcct tatctcattg    120

atctcagtat aatgaaagga agcagtatca catgcattgt gatgttttaa agacattctc    180

ttcagcgttg ctatgtgcta cgccataggc catagcacca tagctaggac taccttgggg    240

ctattgtatt aggtctattt agagacatca tggtgatgaa gtgcaacata acatgatggg    300

tgcactagtg taatgaagta cagtataatg atgagtgtag cggtatgaag gttagcagca    360

ccatgatggt tggatgcagc atgatgactg gatgcagcat ggttgatgta ccgcactgtt    420

gggtgcaaca tggtgatgat gagtgcagca cagtgatgat ggacatggta cgaagggtgc    480

aacacaatga tgggtgcagc aaagtgatag gtatagcttg gttcaaatct gctacctcag    540

gtgtcatctt cttagaaaag atcnctgctc ttattttgtc aagtctaaat gttgacttct    600

gaagtatatg tt                                                        612


<210> SEQ ID NO 299
<211> LENGTH: 495
<212> TYPE: DNA
<213> ORGANISM: Pinus taeda L.
<220> FEATURE:
<221> NAME/KEY: unsure
<222> LOCATION: n at 476.
<223> OTHER INFORMATION: n is  a or g or c or t/u, unknown or other.

<400> SEQUENCE: 299

acgtatatag tgtatgagtt ggaccttgag tggcttctat gacttgaaga aaacaaaaaa     60

catagataag cacatgtata gttgcgcaaa agaagaggaa ttatgagtag ttggttccaa    120

aaaacttgtc ggattcaacg tgcccatatt gccaaaacta acctgcgatg agacaaaagg    180

aattccttag ttaacccccg attctcgtaa agaaatctag catgagaaaa tatgataaac    240

acggataagc aatttaaact ttaccttggc aaagggaagc aaagtcattg caataaaacc    300

atgcaacaaa acaaacacat caaagttgaa catacccatg aatatgtgtg tgtgtgtgtg    360

tgtgtgtgtg tgtggagaga gagagagaga gagagagaga gactcgttca aaagaggacg    420

aatacagatt ctagagcttg aaaagggttt tttcaataat tgccaatact caacanattg    480

tggcttccac aaggg                                                     495


<210> SEQ ID NO 300
<211> LENGTH: 352
<212> TYPE: DNA
<213> ORGANISM: Pinus taeda L.

<400> SEQUENCE: 300
```

-continued

```
gtgttctttt atctctgtga tctagacgca caccatatga ctattactta ctaggatttg     60

gatgaattca tgtggcaaaa aatcactgca gtttggatga atttatgtgt caaaaaatca    120

cagtggtttt gatgaattta tgtgacaaac aacccttgcg ttttggaaaa caatagttac    180

agtttgagtg aatttatatg gaaaatattc attgtggtat gagtgagttt tatagaacta    240

tattttgtgg ctcttgcgca cgtgcacaca cacacacaca cacacacaca cgcatgttgg    300

cttgatgggt cctgacccag gttcagagtt aattagccaa aaaagtcctt gt            352
```

```
<210> SEQ ID NO 301
<211> LENGTH: 541
<212> TYPE: DNA
<213> ORGANISM: Pinus taeda L.

<400> SEQUENCE: 301

atctccactc ttaaagagag gaatgaccac actagtagtc cactctctcg gaaagccgtc     60

ctagatgatc ccattgaaaa ttccttttaa atgaggagca aggagcttag ctccccattt    120

taggaattca gctttaagct cgtctatgtc ctctgcttta ctgcttgcta gattctttat    180

tctctgcttg atgtcatcct ctgtgaatag ttccactgaa ttgttcacta tggggggtat    240

ctttctcatg gacccactca taaaggagcc tcacatactc caaccatttg ccacctataa    300

tactgttttt agtctgcttt atcctttgtt ttagctcttt ccaaaatccc ttggggttgt    360

gctttcccag agagattaac tcctttcttc ttccacacac acacacacac acacacacac    420

acacatatat attatactaa ttttccatat gtcttcttgt tttcttgctc cattttctca    480

cttttagaga tctcctggct accttgcatt cttcatcata ccatggattt gttggaaaag    540

t                                                                    541
```

```
<210> SEQ ID NO 302
<211> LENGTH: 385
<212> TYPE: DNA
<213> ORGANISM: Pinus taeda L.

<400> SEQUENCE: 302

acgcaagcta tgatacaacg ctgcaatata tttatatatg cagggaaaac aacacacaca     60

cacacacaca cacacatata tatacatgca atggcaccat atatatacac agcaatagag    120

aagatattta cacgctcagc tttcacactc agccaacata tatacataca cacagtcaat    180

atatatacac atagtcaatt tatataaacg cacaatatgc agatattcac gagtagtagg    240

gaatcagaat agtgatgcat gttatagtga tgctctgtct atagggaatc agatattcac    300

gggtagtagg catgttatag tgatgctttg tctacataac tacagtcaag atctggtgag    360

aacaaatccc gatggattta tagat                                          385
```

```
<210> SEQ ID NO 303
<211> LENGTH: 498
<212> TYPE: DNA
<213> ORGANISM: Pinus taeda L.

<400> SEQUENCE: 303

agtttcttgt cttcggttaa tttttgttgc ctctcatctg tcactcttac aagcctctaa     60

cttgcataat cataaaataa tagtccaatt gtccatgtat ctggttacga ggattaaaac    120

aaagcatagg ttgtgatcca agtcccctgc aacacacaca cacacacaca cacacacaca    180

catataatta agggttgaaa atagagactg taaaaggaat ggcttatgag atttattcat    240

aaatccactc ttgccacact ctaattattt ttattaaata aatacatcac taaaggtcac    300
```

-continued

```
tcaagatcca agagaatagg accgaatgga ccattattag cataatagaa aaattacaac    360

aattggataa atttaataga ttacatggca atcaaaacaa actcctatca taacaatccc    420

actcattaag gaaccaactc ctttaataaa atattttgac ctctcagtca atggatttta    480

tgaatgctct tgtatcgt                                                  498


<210> SEQ ID NO 304
<211> LENGTH: 444
<212> TYPE: DNA
<213> ORGANISM: Pinus taeda L.

<400> SEQUENCE: 304

acctacaaaa accaccatta tgctgctcaa aaccaccttt gcggatgaaa aaccaccttg     60

gaaaattgtg ttctggtatg gcaggttcga cacctgcata acaattaaat aaagtttggg    120

cggcttgaat accaagctcc accgcttggt ctattggcca tcgaacttgt gttaaggcgc    180

tagtatatat agtgggaggt tggcgggtcg aaaccccac ccgacactcc aacattttac     240

atggaattga tatgatatga tatggataga tatatgtgtg tgtgtgtgtg tgtgtgtgtg    300

tgatatttta tatggtttaa tacatatgtt tcaatacaca tattctggta aggtgactgg    360

tggtcgtggg gttgaccccg accgtccgac cctttttcgg tggccacatc ctgaaacatt    420

aaatataacc atatcccttc tgat                                           444


<210> SEQ ID NO 305
<211> LENGTH: 521
<212> TYPE: DNA
<213> ORGANISM: Pinus taeda L.
<220> FEATURE:
<221> NAME/KEY: unsure
<222> LOCATION: n at 20, 178, 296, 360 and 449.
<223> OTHER INFORMATION: n is  a or g or c or t/u, unknown or other.

<400> SEQUENCE: 305

acatatgtag tgagctttan ggctttagag agtgattttc gatccgatcc aatggttcca     60

tataaatatg taagcctaca ggcagaaaat aggaggccac caatagtcga atcgggcctg    120

tacgtgtgtg tgtgtgtgtg tgtgtgtgtg tgtgcgagac caaggagtct cggatgtnat    180

ctatatttta cattaatata tgcaagatta tttcttgtct atgtcatgat gcttgagaag    240

taatttatgt gtgaattact tgtgaatttg taggctttgt tgtaggttgc aggtanaatt    300

ttgaaggaca cagaggagca aagatgattc agagaaatca tagagggatc attgaatccn    360

agtgaaaggt agagtttcct tggagagggg ttgtgaagca agaattcgct aaggaatcta    420

gcgcagagaa agctgaacaa tggaagtana agacagagtt tgaatgacgc tgctgggaaa    480

gaaatatgat tgggagaaat catattgatc cattcgaggg g                        521


<210> SEQ ID NO 306
<211> LENGTH: 704
<212> TYPE: DNA
<213> ORGANISM: Pinus taeda L.
<220> FEATURE:
<221> NAME/KEY: unsure
<222> LOCATION: n at 478, 498, 501, 504, 546, 562, 577, 598, 660, 682
      and 687.
<223> OTHER INFORMATION: n is  a or g or c or t/u, unknown or other.

<400> SEQUENCE: 306

atcatagctc ttaggttcaa caattggact agatgggtgg aatgtatttg tcatgcatgc     60

atgttagttc tatatgtgtt cattatgcat gcattacaaa tgtcattgtt gtaagtagtt    120
```

```
tcatcatgta aaggttgatg atattgatgt cgagatgata gatatgttga tttaattata    180

tatgtgtgtg tgtgtgtgtg tgtgtgtgtt ttgctaatct agattgatct tgcaaatagg    240

ataacgtcct ctaaacttca ctaaggtatg ttgtttatgt ctacgtttgg ttgatttaaa    300

agcgtatatt ttcatattgg tagaagatca aggatgacaa gtaaaattgt ggactacagt    360

tcacatgatt ctccatacct atcaaatgag taggatggtg atgagtaagc ttccaacccg    420

aatgtccccg atagtcaggc gtgtcaccca tcctattgat gttgtcaccc cttattanga    480

aaggggagtg gtaacganga nganattgtg aggaacctcg aggggttgac tcatggtatc    540

ccgaantatg ctcagatagg anacatgccc tgacganacc agaagcacac agtgagantc    600

ttagatcgga tccaccgact gctaaatcga attgcacaag ttgtctcatg ctaccatgan    660

cactatgctc agtaattcct angtccnaca cttacatatt tttt                     704
```

<210> SEQ ID NO 307
<211> LENGTH: 505
<212> TYPE: DNA
<213> ORGANISM: Pinus taeda L.

<400> SEQUENCE: 307

```
atcttgatct tttatctttc attgcaatca aatataacca tagctatctt tgatattgtg     60

aaataatatt tgatgtggtt ggtgtttaca atctcctcca cacttatgtt ctatgcatat    120

aaggatttct gatggcttga aatgtattcg tatatccttc caaaaaccta caacgttgcc    180

tctgagatat aagaatgcaa atcaatgaac gcataccaag gaagctatca aatcgcctga    240

tggatccaga taggttttca tagtcggtga ttgtgtctat cttcgaccct aacagatgtc    300

aaggccaaag gcagagagct atgcattgtt ttcataactg ttgttttgat atatatatat    360

gtgtgtgtgt gtgtgtgtgt gtgtgcgtgt ggcttttaaa tattgttttg gcatatatat    420

gttgttcagc tttggcacac catagcgggt aatttgaatg cagacattga gggagctttc    480

tgatttgcta accattgcga aaagg                                          505
```

<210> SEQ ID NO 308
<211> LENGTH: 504
<212> TYPE: DNA
<213> ORGANISM: Pinus taeda L.

<400> SEQUENCE: 308

```
gcaagagttt tcctgtgaaa ccaatccttc tgcaatcttt atttcatcca tcgatatgtg     60

tgtgtgtgtg tgtgtgtgtg tgcttcaaca gtgcaagagc aagcattata aacgagataa    120

ccttttaatt aatattgata gagctgcagc agcaagagga gccaaggaga ccaagagggc    180

tgcgagaagc cagaggaatc agggagtcat gaagagtcct ggtgcagagt tatctatcta    240

tacaatatca ccgagcctgc atagcactta gtgagttttc tttttggtga agtctttcat    300

ttaacgaaac ccaggaccat cagtcgtcaa cactcataac agggattgcc caaaagcccg    360

taatatttac aaattgcatt ttaaaaagcg tcgggcacca gagaacgtct attaaaagaa    420

ttgcaagaag acgagaattt tcatgttgcc caaggccatc aagcccagag gtaattcgaa    480

ttgagagtca ggcacacaag tggg                                           504
```

<210> SEQ ID NO 309
<211> LENGTH: 273
<212> TYPE: DNA
<213> ORGANISM: Pinus taeda L.

<400> SEQUENCE: 309
atgagagaaa tctcaaacac aacacaacac gcacacacac acacacacac acacacacac 60
acacacacat atgtaagcat atgaacactt atttcagtta tgcattcacg agctaagtct 120
aggctgaagt agcacaagtt taggagggat aacacacaca tttgttttga aagcgacaag 180
tcgaattggg ttgaatacct tcagaaatct caggagggat aacccaggag gacctacata 240
tatcatagta tatataaaga ctgcgcatca gag 273

<210> SEQ ID NO 310
<211> LENGTH: 568
<212> TYPE: DNA
<213> ORGANISM: Pinus taeda L.
<220> FEATURE:
<221> NAME/KEY: unsure
<222> LOCATION: n at 373, 391, 395, 498, 506...507, 524 and 565.
<223> OTHER INFORMATION: n is a or g or c or t/u, unknown or other.

<400> SEQUENCE: 310
ctaagtccat cgagaatgag aaagaggaca tatttccaaa gtaaaagaac cttaaagaat 60
ttgggggctg agctcaagga cttggaagat gagttaaata tctgcaggga agaacttaga 120
aacctcactt gggaatagtg agagttgatt gagtggaatg tttaactatg aaaatagttg 180
tgagaaatga catataaaga tgaatccttg aaaaggaaaa atggaattga caggaagagg 240
tctcgtgagg ttgaatagga gaaggggata ttctcctatt ggtgttgtgg agaagaaaat 300
ttgagaaagg actatccccg taggaagaat aagaaagaaa ctttccccta cgagccacag 360
ggggaacatg tcnatgatgc aggatgccca naaangctga ggggggactc cttcaagctc 420
cttgacacat atatatgtgt gtgtgtgtgt gtgtgtgtgt ttgttgaaaa catcacctgt 480
gaacttttgg ggaatgtnag acttcnnggt tgctgtgagc cttntaaaga agtcttgaac 540
taattttggt ttatgaatat gcatntgt 568

<210> SEQ ID NO 311
<211> LENGTH: 447
<212> TYPE: DNA
<213> ORGANISM: Pinus taeda L.

<400> SEQUENCE: 311
acaattcccc acatcgttgt aatctcctgc tttgagacct taataacaat tctattatgg 60
actaaaactc aatcgctcca ttatgtttgt gttgacgtag taagttgcgt ccatattata 120
atccctaccc aactatgtcc aaccttcata atatttattc ccatacaata gtatatgatt 180
cctagatgga cctgggggtc aagacaatca acgccgcttt agacaaggtt atgggtaatg 240
ccaagtaaat tatcattcca cacacacaca cacacacaca cacacacaca cacatatata 300
atttggtggg cttatgtcga caataccaac gttgtctatc cctctaagaa caaatcatta 360
tattatatgt aatgtataag atgggatcaa caatctacat tgactaccgt caacataatg 420
gtgaaccgtg agtttccatc acggagg 447

<210> SEQ ID NO 312
<211> LENGTH: 462
<212> TYPE: DNA
<213> ORGANISM: Pinus taeda L.
<220> FEATURE:
<221> NAME/KEY: unsure
<222> LOCATION: n at 44, 411, 422 and 458.
<223> OTHER INFORMATION: n is a or g or c or t/u, unknown or other.

<400> SEQUENCE: 312

-continued

```
atctttgggg cacaatcact cacggattga gatacactgt cagnagatgt gaggttgcat     60

ggttattctg aatgttgatt gggttggaag tgtagtggat cgcaagagca cttatggatg    120

ttgtttttct ttgggctctg ctttgatatc ttggatgagc gagaagcaaa aatcggttgc    180

tttgagcacc atcgangttg aatacatagc tgctagtatg gcctcctgtg aagctgtctg    240

gttgaggaag ctcttcagtg agttttttgg acatatgttg gatcgtgatc ctctgtgaca    300

accagagtgg aatctgatta tcaaataatc ttgtgattca tgatcactcc aagcacacac    360

acacacacac acacacacac acacacacac acacatatat ntatatatca acgaccttct    420

cntcaatccc aatgtgatgg aagccttatt tctcctcntt gt                       462
```

<210> SEQ ID NO 313
<211> LENGTH: 521
<212> TYPE: DNA
<213> ORGANISM: Pinus taeda L.
<220> FEATURE:
<221> NAME/KEY: unsure
<222> LOCATION: n at 444 and 461.
<223> OTHER INFORMATION: n is  a or g or c or t/u, unknown or other.

<400> SEQUENCE: 313

```
atcatataac tgctcatcgc aatcgggaat cggtgattct tatggtaata atgtaattgc     60

ctgctgcatc tttgcaattg cgattaactg cattgcttaa aacacacaca cacacacaca    120

cacacacaca catatatata ttggttatgg ctccatataa ccatttataa ggtgatttaa    180

cttggtcaca tgggtatact agggtcaatt cttttatact tgtgctttta gcgattcggc    240

tatgccatta tcacttcttc atcttgcttt tatctttttt tgaaatattt tcaagtgatt    300

attgagtgaa aaatgaatac gatacgtaat aaaaatgcat gttacaacag aaggtatgtc    360

taatttctct ctagattttg atttctgtga aaattgtgta tttgggaagc ataatcgggt    420

gagtttcccc tctagtgcta aganggcgaa acatatatta nagcttgtgc acagtgatgt    480

gtttggacct atgtcggttc catcactggg taagtctatg t                        521
```

<210> SEQ ID NO 314
<211> LENGTH: 575
<212> TYPE: DNA
<213> ORGANISM: Pinus taeda L.

<400> SEQUENCE: 314

```
acatatgatt ctacaaatat catttaagaa cacacacaca cacacacaca cacatatacc     60

accatcatga tgtgacaaat gatgatcctt ccccgattca tgttataatc tccttgatcc    120

ctgaccaatc tcatcaacat gcatagaaag tcgccctcta gttgatgcat gagacttaat    180

tgatgctaca tcgcatttac acctcaaaga atcaagtggt aactgctcat gtgatgatcc    240

agaccctcgt tccatacata catacataca tacatacata catatatata taatctttaa    300

aaaaacccca agttacctca tgcatttaaa atctttaaaa ttgttattta aaaacatcaa    360

gaattcaaaa aattgataag acaagtaaat gtaactatcc aagggttttc ttcaaaaaat    420

tttgatgtaa attctttatt tcaaatatac tcaagactaa aaacacaaat tctgaagtgc    480

acattttgat aattaaatac atttttttaa aacatgtcaa attcaccaag ttgaaagaaa    540

cacatggtca ttaaaaacat acacatatca aagat                               575
```

<210> SEQ ID NO 315
<211> LENGTH: 584
<212> TYPE: DNA

-continued

<213> ORGANISM: Pinus taeda L.
<220> FEATURE:
<221> NAME/KEY: unsure
<222> LOCATION: n at 528.
<223> OTHER INFORMATION: n is a or g or c or t/u, unknown or other.

<400> SEQUENCE: 315

```
atcaattgaa atatacaaaa gaagatactg aaaggaagga cattgaccac aaacaaaaat     60
ataagaagaa tgtagattta ttgaacaagc tatggcaata aatagccaat ttgagagaaa    120
attatgaaag aaaaatttga tagctctaac aaggatcaaa ggatgtgtct gttttattgc    180
ccaaatgatc acatgtctcc acagaaggaa agatacactc ttattctcaa gaggagggct    240
tgtagaatca tcccaagcat cctcaagttt caaaatagca atttttaggt gttgtatcta    300
tgtagacaca tttcaacatg tcacacacac acacacacac acacacacac acacacatat    360
atattcttgt taacatgcat tatatatcat tatattttcc attaaaccac atttttgaat    420
aaatttctag tctttttga ggatttacac ttatgtctcc ttcatggagt ttttatctgg     480
ttgtggtctc attgggatct agttactctt ttatttttgg acaatgtnat ggaattttat    540
aaactgatag cttattgaag tgagaaatcg gtgttatgga atgt                     584
```

<210> SEQ ID NO 316
<211> LENGTH: 444
<212> TYPE: DNA
<213> ORGANISM: Pinus taeda L.

<400> SEQUENCE: 316

```
actttgtatt tatcattctt tttcatatga atgtaaaagc atgatttacc tattttattg     60
ttcagcaata gcctgttgta gatgggaatg tttataagtt ttctagaatg ttatcattcc    120
attttgtgtg tagttctgtt aaatgttgca tgatgtgaat gccttcactt catgtttact    180
cgttaatgcg cttactagct ttttttcctc atgagaaata tgtttaaatt tgtgaattgt    240
gtccatggga acagggtcac cttcgggctc aaaccctaaa tcattaaagt tagttactct    300
gttgctattt tggtctcgca cacacacaca cacacacaca cacacacaca cacacacaca    360
cacacacaca tatatatatt gcttcacatt tcgtgtttaa gcctcaccga ttcttggcct    420
gtaattcatt gctccggcta cgga                                          444
```

<210> SEQ ID NO 317
<211> LENGTH: 527
<212> TYPE: DNA
<213> ORGANISM: Pinus taeda L.
<220> FEATURE:
<221> NAME/KEY: unsure
<222> LOCATION: n at 72, 84, 128, 319, 344, 375, 437, 465, 480 and 508.
<223> OTHER INFORMATION: n is a or g or c or t/u, unknown or other.

<400> SEQUENCE: 317

```
actatattta ttgatttgaa atattaagaa gagcatctga caaagaataa agaggttaga     60
aaagagaagt angctgagaa gtangaggga aagtatgtgc taaagctaag gtagaagcca    120
tgacgcanaa gcatggtaaa agggacaata tggaaggatc cacaaccaat ggatgcaaca    180
aagagaatcc atgagaagtg gggcgacgga agatgactag tgaccaataa agcatacata    240
tatatgtgtg tgtgtgtgtg tgtgtgtgtg tgtgtgtttg tgtaaacact ccaaatacat    300
agaccagcaa caagccccna ggcaaagaat tagataaagg agcnagaaga gcatgaaggc    360
tagttgagga atacnaaggg agaagcagaa gggaggcgaa atgagaccag agggctaaag    420
aaagagagta gttgtanaaa atgatattat tctaagagtg gaccnacaat gttgtgcccn    480
```

aagcctgcta ctagggaaca aagaaacnaa ctatggaagc gaaaagg 527

<210> SEQ ID NO 318
<211> LENGTH: 441
<212> TYPE: DNA
<213> ORGANISM: Pinus taeda L.

<400> SEQUENCE: 318
atctaatacc acagaatggt atcggaactc taaggttcaa cactaggact ggatgggctg 60
aatgtgtttt tcatgcatgc acgttagttg tatatgtgtt cattatgaat gcctagtgat 120
tttcattatt gtgagtagtg cagtcatgta gaggttgatg atgtcgatgt tgagatgatt 180
gatatattga tatatgtgtg tgtgtgtgtg tgtgtgtgtg tgtgtgtgtg tgcgtgtgtg 240
tgtgttgtgc taatacatat tgatcttgta gatgagatag cctcccttga acttctctaa 300
ggtatgttga gtatgtttgt atttggttta tctaacatgc tgtgtttgca agaagtagag 360
gatcaaagtt gacaagtaaa atggtggact atagttcacg tgattctccc taaagataaa 420
atgaacaaca tagtgatgag t 441

<210> SEQ ID NO 319
<211> LENGTH: 487
<212> TYPE: DNA
<213> ORGANISM: Pinus taeda L.
<220> FEATURE:
<221> NAME/KEY: unsure
<222> LOCATION: n at 15...16, 18, 54, 104, 122, 191, 285, 294, 329, 379, 395, 405...406, 410, 439, 450,
<223> OTHER INFORMATION: n is a or g or c or t/u, unknown or other.

<400> SEQUENCE: 319
atctctccac agctnnanag acanattgtg ggggtagagt cctctcatta tganagactc 60
ctatgacatc tttttcatgt tctttcgtgt tatcaccaac atanaggaga ttaactcctt 120
angatatttt ttatgggata tgtctttgca tatgtattgg attatgatcc taagccttag 180
aaacccttat nttgactaat gtatgctaag tatatttgtg ttgtaaaact cttttgtgat 240
atataatgtg tgtgtgtgtg tgtgtgtgtg tangtgcatg tgttncagcc tcantattgt 300
acacttgtga atgttgtctt atgatgttng cattcaggtt tctactgaat gtatcatatg 360
acatgggtga caaanttant gtgacaaatg tccanatatg acatnnttan cccatgaata 420
acctaatgtc ttagaatcna gtaatataaa tgtntgaaan ggtggtgaat cccattctag 480 canangt 487

<210> SEQ ID NO 320
<211> LENGTH: 417
<212> TYPE: DNA
<213> ORGANISM: Pinus taeda L.

<400> SEQUENCE: 320
atcaagagaa taagtttgcc caaatttgaa caagctgtag catgaagatc actggtagta 60
gcaacagatg cacacactaa atcaaccttc ccttcaattg aatcaacact gaagcactga 120
atcaatcttg gctcaccaag ttctactctt actctccaag tctctccctc acaaccttct 180
tcaactctct ccaaccctct ctcaagtttg aattcttctt tcacaatgcg caagtagtga 240
gggaaaaaag aatgaggcgc acacatacac acacacacac acacacacac agagatatat 300
atatatatat ataggaggag caacgaatca atgccataaa cggggattaa ctcgcatgcc 360
aagagggaga gtaacatatg cccttttagg aaatgtaact catgccatta agaaggt 417

<210> SEQ ID NO 321
<211> LENGTH: 343
<212> TYPE: DNA
<213> ORGANISM: Pinus taeda L.

<400> SEQUENCE: 321
acttcattta ggttttaaca tttttcaata aattagcaaa ggaatgaaaa cgaacaagcc 60
atggttaatt tactagaaat aactctctct ctctctctct cacacacaca cacacacatg 120
catgcaagta aacactaaac tctctctctc tctctctctc tctctcacac acacacacac 180
acacgcacac atgcatgcaa gtaaacacta aactctctct ctctctctct ctctctctct 240
ctctcacaca cacacacaca cacacacaca cacacacaca cacaagtaaa cactaaatct 300
acaaccgtaa aatatatgtc aataataatg ctaagtagag agg 343

<210> SEQ ID NO 322
<211> LENGTH: 414
<212> TYPE: DNA
<213> ORGANISM: Pinus taeda L.

<400> SEQUENCE: 322
atcaaattca ctgagataaa atcgtaatag atgttgattc aggtgcatgg tggtgatgtt 60
acaggtttag cttcttcgtt gggcactaag atgcttagag ttgaagccct aaagagggct 120
gagtccttcc tcacttcaaa atagacattg cattgctcag atattcacaa gagtgatacc 180
acaaggctgg gcattgaagt catgctttaa acgtgcttcc cttgcttcag acttggcctt 240
acagcatagt gtcatatgcg tcaacttagg ttcagaggaa tccatagatc atgctcagaa 300
caacgaaacc aactctgttt ttatctcaga aactcgtgga tgattagaag cggccacaca 360
cacacacaca cacacacaca cacacacatg tatataccca aagtttgcat ttgc 414

<210> SEQ ID NO 323
<211> LENGTH: 431
<212> TYPE: DNA
<213> ORGANISM: Pinus taeda L.

<400> SEQUENCE: 323
acctcataga ttttagacca tatactaatc caatggatga gagagattat acaatcaacg 60
tatccgattt aattacatgc ccccctcctc cctgtgacat caccgagggg ggtgtcacat 120
tcatggttcc aatgtgggat tccacctaca tatatatata tatatgtgtg tgtgtgtgtg 180
tgtgtgtgtg tgtgtgttat aattatcacg agatccacgc ttatcattat acaaccatag 240
gtataattac ttatagattg ggtcccttgc tccacttaat tacatccccc atgtatatgt 300
ggatgtgaca atcacaagac ccctatttta gttatccata tatgtatata tgaccttaat 360
atttgtggac cccctcttta cctttatatg acttaatgct aatagaaacg acatagtgag 420
ggcccacctt c 431

<210> SEQ ID NO 324
<211> LENGTH: 457
<212> TYPE: DNA
<213> ORGANISM: Pinus taeda L.
<220> FEATURE:
<221> NAME/KEY: unsure
<222> LOCATION: n at 364, 418, 422 and 447.
<223> OTHER INFORMATION: n is a or g or c or t/u, unknown or other.

<400> SEQUENCE: 324

-continued

```
atctatgtag atcgcatacc acatagaaaa taccctggtt tatattagaa taagttaatt     60

agaagatttg catgatagaa taggtcattt agattatcat tattttattt gcaagcggtt    120

atgaaccgcc cactctcata ttaaaaccca cactaggaaa ttggtcccat tatccccagt    180

cggagccacc actttaaacg aaaaaggagt tgtcttaagg tccagatcgg gtagttatcc    240

cccatgttgt tgcaacgatt tttgaggccc caacagaacc cttccaatcc tttaacatat    300

ttggcttcct ctcttaaagg tcagatgagt ttgcactctc tagtcacttc tatataaaac    360

ttcntatgtg tgtgtgtgtg tgtgtgtgtg tgtgtgtgtg tgtttatttc tctcgtcnag    420

gnaatgaaag catagtgctt ctacccngaa attaagt                             457
```

<210> SEQ ID NO 325
<211> LENGTH: 430
<212> TYPE: DNA
<213> ORGANISM: Pinus taeda L.
<220> FEATURE:
<221> NAME/KEY: unsure
<222> LOCATION: n at 2.
<223> OTHER INFORMATION: n is a or g or c or t/u, unknown or other.

<400> SEQUENCE: 325

```
gnagaatatt gagcagacat catcaacact aagtaatgtc taacaaggac cctcaataat     60

tctcatatgt tttttactta taaccatgag tcttgtagat agagagtgca tctgtgtgtg    120

tgtgtgtgtg tgtgtgtgag tgtatgagtg tttgaaagag tggttgtaat ctgtgctttg    180

agagactaga gactagaaag ctctactctt tgaggcataa cctggtatgt aacaattttc    240

ttgaattaat actgaagcct actgggctgc ctgtctgagg acagtttgtt tcgagatcat    300

ctaaaagcga gattttaaag cgagttggag aagcgaaaga gttgcgtgtc ctcgtatttc    360

tcgagctggt gtgaggaatt tcagcatact cttcagaggt tcaagtaagt tattgactcc    420

atcatgttgt                                                           430
```

<210> SEQ ID NO 326
<211> LENGTH: 437
<212> TYPE: DNA
<213> ORGANISM: Pinus taeda L.

<400> SEQUENCE: 326

```
atctaaactt ttgtgcaaat gtaacacgga tctctggaaa ccatgaacta cacacacaca     60

cacacacaca cacacacaca catgttggaa ataatactga taggggggt gaatcagtat    120

tatcaagtca gatattcctt ttccaaaatc aattgatata cgctacttca gttaattaaa    180

cccgcgtata tacgcaacta ttctgaggga aaccagcgta tacaaagcaa actattgata    240

taatttatct ttttgatgtt gattgttaat ctgtgtttcc ataatcaaat aaccagtaac    300

tagaaatagt aaaacaaagc agaaagacaa ttgcacacaa gaacacaaga tataaggtgg    360

aaacccaatg tgggtgaaaa ccacctgctg caattcgtct ctatcttcct ttaaattaga    420

aacttctttt acaatgc                                                   437
```

<210> SEQ ID NO 327
<211> LENGTH: 424
<212> TYPE: DNA
<213> ORGANISM: Pinus taeda L.
<220> FEATURE:
<221> NAME/KEY: unsure
<222> LOCATION: n at 247, 258, 292, 308, 369 and 377.
<223> OTHER INFORMATION: n is a or g or c or t/u, unknown or other.

<400> SEQUENCE: 327

```
gctcaaatag agaatatgga aattttccgc aaactatgtg acaaccctaa gttatagaaa     60

ggtatgttga cacctttga gatcctatac ctgatgcatg aaaagtggga acctatgatg    120

acaatattgt aagctagaaa aaggatagtt tgaggaaaca tgaatacatc taacaatgaa    180

agtgtatgtt aacatcttaa ggattttgtt ttcctcataa tcacctaaag aatttctaat    240

gagtatnggg agatgtcnta aaaaatgtct gacatgtcac aacacacaca cncacacaca    300

cacacacnca catatatatt ctacatatag aaagaaagaa aatcgatcaa ataaaattcc    360

gataaccgng aatgtcntcg tatgatgtgt tgacatggaa agtggcatat gctatgccct    420

aaat                                                                 424
```

<210> SEQ ID NO 328
<211> LENGTH: 540
<212> TYPE: DNA
<213> ORGANISM: Pinus taeda L.
<220> FEATURE:
<221> NAME/KEY: unsure
<222> LOCATION: n at 205 and 263.
<223> OTHER INFORMATION: n is a or g or c or t/u, unknown or other.

<400> SEQUENCE: 328

```
atctcgtctg caagaccgac tggattagca caacacacac acacacacac acaaacataa     60

tcaaatcaac atatagtcat cattccaacc attgtcaaac tatcaatgta tgagcatacc    120

caccacatat catgacctca tgcatggtaa ctactaccat atcactgtac gcataacaac    180

atgtgtatga aacgcacaca taccnctgtg ttatgtgtgt gtgtgtatgt ataggtgtat    240

atgtgtgtgt gtgtgcgtgt gtntgtgtgt gtacaacgac accatcaaat ttcacatggt    300

gacacgacta aaaccatacc caagaccatg catacacaac caatacatag accataaaca    360

taagaacaca tatgcaacca acatgaatgc atgaccaaca caacacccat tcaatccaag    420

gggcgaaaca tgctatgata ccactctatt acaccctctt cccacatcta cccaagtaac    480

cgactaacca gggtaaaaat gtgatgagag gctactatga tctaagtaac ctccccatgt    540
```

<210> SEQ ID NO 329
<211> LENGTH: 527
<212> TYPE: DNA
<213> ORGANISM: Pinus taeda L.
<220> FEATURE:
<221> NAME/KEY: unsure
<222> LOCATION: n at 387.
<223> OTHER INFORMATION: n is a or g or c or t/u, unknown or other.

<400> SEQUENCE: 329

```
ccatctttga taggattgtt gtggaaattg tgtggggtcc aaagttgccc attcgagtcg     60

ccagacatct gcacaagttg tgtgagtgag caatgccgta acccaccaag ccaccgttcg    120

aaaaggagtc gctaattttc atcatgcatc acgtcgtgtg gggaagaaag agaacaaata    180

aaatgtgtat tttattttca ttcatttggg atgtagaaat tctagactac aaacatcgtg    240

atcgcatgat ctcaggagcc aagaaaattt tattttgaac ccaaagttga agcaaattca    300

accgtggacc tggcgttgta tcgaatctct gtttgtggta gcttggatgt ccttagtgaa    360

ctaaggctgc gtagcaaatc actggangtt gtgtgcgtta aaaggtagtg gagaagtgcg    420

tatgatatat atatatgtgt gtgtgtgtgt gtgtgtgtat gttacagtgt gaaaaccaat    480

acatagagaa gtcaattgtt gatcccacat cagatcacat cattagt                  527
```

<210> SEQ ID NO 330
<211> LENGTH: 573
<212> TYPE: DNA
<213> ORGANISM: Pinus taeda L.
<220> FEATURE:
<221> NAME/KEY: unsure
<222> LOCATION: n at 319.
<223> OTHER INFORMATION: n is a or g or c or t/u, unknown or other.

<400> SEQUENCE: 330

```
cccacaaact cttggtgttc catctcctag ggttagggtt ttggttgttt aggtttccct     60

ttgtagttca ataataaaaa ttcccttgag cctcattgta gcacaattca aaggcatgtg    120

gctgccacat cacttctcag agataagcta ccattgcccg agctagttta tttccatcat    180

gtgtgtaagc atcttttagt tctttgatat tagtgaaatg aagttttatt cctactacat    240

ctttgtgttt atgtttatgt atgtatttta ttttgtttct acataagtcc agatcaataa    300

acacgcacac acacacacnc acacacacat ttggtccaat ggttgggcct tgggtccaat    360

ataacattgg catgtaacca tgaattaatt tccacgctat gaaccttgat cacttggggc    420

ttacacattg tccatatgac tttatctttg caggtaatta accagccaca tggtgacatt    480

agcattatgt catcatgcca catgatggct agtgaagang tgccacatgt cacctggaaa    540

acaagttgat tggtcactcg agctaccatt tgt                                 573
```

<210> SEQ ID NO 331
<211> LENGTH: 538
<212> TYPE: DNA
<213> ORGANISM: Pinus taeda L.
<220> FEATURE:
<221> NAME/KEY: unsure
<222> LOCATION: n at 9, 182, 286, 341, 346, 357, 460, 479 and 528.
<223> OTHER INFORMATION: n is a or g or c or t/u, unknown or other.

<400> SEQUENCE: 331

```
acattgtang attgcaaaat gtgactttag aggatagaca tgagtttttt ctaacaagtc     60

caatcaccaa ctattagtga ttttatactt atcttggagt ctcgaacact gtgggaacac    120

acacacacac acacacacac acacacatat gttggcatta tggtgtgcaa ggatccaact    180

anttgatgtt gccattggga tgattgtgtt ggcattgatg tgaacgatat gttggcattg    240

ggaaatgatg attgccacac tagttgattg ggaactaggt cttcangctt atgttcgtgg    300

agatgacttc ttgcgtgtta ggtaaacttg actcaggata nagtcnaagt tgaccangtt    360

aaacagtgat ggttttgggg cacatggtat tgtgcgccca tagtattctg cccatggtat    420

tatatgtaat gggagcttat aaaaggatgg aaggacttcn ttgtcatgta tgcctgcang    480

tgagcggtga acgctcactt ggtcagattg gctagggttt ttggccantg ctaatgaa      538
```

<210> SEQ ID NO 332
<211> LENGTH: 419
<212> TYPE: DNA
<213> ORGANISM: Pinus taeda L.

<400> SEQUENCE: 332

```
atcaacccac tatcacaatc ttccttttaa ttattcctat caaaggtgtc ccaccacttg     60

cacctaagaa ataacacatt tgaatgaaga taagtccact tgaaattata tcttgtatct    120

ttccaacgta acctaatgtc ccctgcatta tgttttgatc ttggtgtcta acacgactag    180

attggtcaaa ctcgacttcc actccatagt cttgtgtcat gcatccatct tcagcatcct    240

tcacgcaaca attatgtcca tatgcccaca tacatgggaa taaatgcacc tataaaaaag    300
```

-continued taaaaaaatc atagtgtcat gtgtctaata acccaaacac acacacacac acacacacac 360
acacacacac acagatatat atgttacatt tcaaaggtgt cgtatgaagt taaaaatgt 419

<210> SEQ ID NO 333
<211> LENGTH: 409
<212> TYPE: DNA
<213> ORGANISM: Pinus taeda L.

<400> SEQUENCE: 333
atcaatccac gaggtcgata aattaaaata acaatccaaa atcataaata agtagccccc 60
aagagtcctc ttaatctata tgagctcaaa gtccatggaa ctatcaacca ttagacaagt 120
gcgcatgcac acacacacac acacacacac acacacacac gcacacacac acacacacac 180
acgcacacac acacacacac acacacacac acacacacac acacatatat atcaaggagc 240
ttgagggagt atgccctcct cctcctcaac atctttctta ttcactctct ttttcttcgg 300
ttggggaaat tcctttttca atgctcttac ccacaacacc aacaagatat tattttctcc 360
ccctcttcag ctccacatag gtttttcctt tttgaggaat caaccaagt 409

<210> SEQ ID NO 334
<211> LENGTH: 643
<212> TYPE: DNA
<213> ORGANISM: Pinus taeda L.
<220> FEATURE:
<221> NAME/KEY: unsure
<222> LOCATION: n at 357, 367, 392, 409, 468, 516, 531, 545, 615, 625 and 638.
<223> OTHER INFORMATION: n is a or g or c or t/u, unknown or other.

<400> SEQUENCE: 334
atcttatgct cacttacttt cttaccacac tatgaaaccc aacctaaaat caatcatact 60
aacagaatgc tctactacca agctaaatga atcttcatga ggaataccct taataggtca 120
ctctaaagta tgggttgtta ccccaacacc ccttcctaag gcacacttcg attaaagaat 180
cataagcacc ttgaatcttc ttaacactaa ttacaaaact aggatcaaac ccaacctaat 240
acatatcata aactactata gatatctacg acaaaaccac gtagtgtttc atacaatcca 300
acctaagcat gtgtgtgtgt gtgtgtgtgt gtgtgtgtgt gtgtgtgtgt gtggatnact 360
acttccnaag ctacatccca ttcacttctc anggaagata aaaatatcna aaccaactta 420
atacctacca tttactaata tagatatatg ccacaaagcc acatgctntt ttataaaaac 480
cactctaaaa aattcaaaac caacttagca agcttntcta tcgagtatta nggggcggga 540
ttganaggcc agtccgatct atgctctgca gggaatatct tgaaacgtat ttcctaccga 600
ccacccgagc gttcngatcc cgaantcaat gaaaactnaa tca 643

<210> SEQ ID NO 335
<211> LENGTH: 422
<212> TYPE: DNA
<213> ORGANISM: Pinus taeda L.
<220> FEATURE:
<221> NAME/KEY: unsure
<222> LOCATION: n at 252, 254, 316, 324 and 356.
<223> OTHER INFORMATION: n is a or g or c or t/u, unknown or other.

<400> SEQUENCE: 335
accacttata acatacctta accacctgct agtttattcc aacctcttgt tgggtcccaa 60
tttcgtgtta gaaacccctg ggaaacctgt gacctgaaaa ttccccttc tattaaaaat 120 ttgtctgatg aaatgcacat ctaactgcat gctaaaatgt aatacatgtg catatgtatg 180
ttctaacatg attatcttat ttcaattaac ttgtgtgtgt gtgtgtgtgt gtgtgtgtgt 240
gtgtgtgttg tngcantgga ataaagacaa atactgctct tttaatttat ggaactggtt 300
gcaagccttt gacgtntaac ctanccaaag accatgttgt tcatttcctt caagancaag 360
ccacccccga gttggggctt tgagtccatg gggaatcaac aataactctc ctaaaaccta 420 nc 422

<210> SEQ ID NO 336
<211> LENGTH: 587
<212> TYPE: DNA
<213> ORGANISM: Pinus taeda L.
<220> FEATURE:
<221> NAME/KEY: unsure
<222> LOCATION: n at 307, 378, 380, 455, 478, 490...491, 502 and 580.
<223> OTHER INFORMATION: n is a or g or c or t/u, unknown or other.

<400> SEQUENCE: 336
atcactggaa agctcttaat gagctaaaca cgatggtaat tttttttaa agttttgatg 60 agtttggaaa aaagatgatt tttgcaaccc catcttcata atagattgcg agggtaagtt 120
taagttataa gtaacaccct ccacaaccca agaataaccc aagcgggcgg gagcgactat 180
tacaaaatgg tattagagaa tggttcaaca ctagacctaa agaggttcac gcgcacacgc 240
acacacacac acacacacac acacacacac acacacacac acacacacac ttaggataaa 300
catgttngct gctatttcca atattgtata catatgaggg ttgattttaa gttacaaatg 360
atataattgt tgacttcncn aaatattgat aagttatttt atcctttaat ctgcatacta 420
acccaagatt tgatgattta gctggtttca catcnacatg gttattgaaa acatgccnag 480
atgatgggtn natatgttta tntacatttt tatttgatga agtgttatgt gtgtgtgata 540
acacctcaga agacaccant gaaacgtcga aaaaattccn aaatgaa 587

<210> SEQ ID NO 337
<211> LENGTH: 262
<212> TYPE: DNA
<213> ORGANISM: Pinus taeda L.
<220> FEATURE:
<221> NAME/KEY: unsure
<222> LOCATION: n at 66, 72, 92, 98, 104, 131, 146, 220, 224, 240 and 245.
<223> OTHER INFORMATION: n is a or g or c or t/u, unknown or other.

<400> SEQUENCE: 337
acatccctgt ggggatgagt tatgtgtgtg tgtgtgtgtg tgtgtgtgtg tgtgtaaaag 60
cnaaangcaa anatgtgtgt aaggacttct anaggtanac atanaacatt tgatgcttaa 120
gaggcataac naatcacatg ctatancaaa ccacatgcta acaaagatta gtaacatatt 180
aaggaataaa cagaactcaa tacatgtcat ggtcaagccn tganaggttg gatcaaactn 240
gaaanatagt gggttttgag ac 262

<210> SEQ ID NO 338
<211> LENGTH: 418
<212> TYPE: DNA
<213> ORGANISM: Pinus taeda L.
<220> FEATURE:
<221> NAME/KEY: unsure
<222> LOCATION: n at 27.
<223> OTHER INFORMATION: n is a or g or c or t/u, unknown or other.

<400> SEQUENCE: 338
atcacgcttg atcacttagc ctactangtt tgagttactc gtctcttcca atccctaata 60

-continued

```
ttctaccctt atagcttaag taatatgtga attacttggg cctttctacc ctcagagcat    120

ggtcgcaatg gttttattgt ccaaggcttt attacgactt agtgtctgag ccgttatgtt    180

attgagactt agcctccact tggtgcatat gcacataaat atgcataagg cttgaacccg    240

atggattttc aaatgaagtc agcctagtct tggttgtagt ggttttgttc ccaatttgac    300

ctaagaatag ttttatgagg ccccttggcc tccaacctac acacacacac acacacacac    360

acacacacac acacatataa ttgttaatcc tcctgagctt acagtttgta aaccaagg      418


<210> SEQ ID NO 339
<211> LENGTH: 429
<212> TYPE: DNA
<213> ORGANISM: Pinus taeda L.
<220> FEATURE:
<221> NAME/KEY: unsure
<222> LOCATION: n at 136, 295, 305, 372, 391 and 421.
<223> OTHER INFORMATION: n is  a or g or c or t/u, unknown or other.

<400> SEQUENCE: 339

ccttagattc taatcgtact gtgtataata caaaagcatg tgttacagtg ttgattgtgt     60

gccagtatgt atttcatata tatgtgtgtg tgtgtgtttg tgtgtgtgtg tgtgtgtgtg    120

tgttaatggc ttgaantcct gtgtttataa gtgtattgat tgaccatcga tcactgtagc    180

atcgatggtg atccaaagat atttgagtta actgttgtat ggagtgatgg catgcttaaa    240

cagagtgttt ccaaattgtg gcagatctgt gttttttaat gcagagatcc atcanaatga    300

tcaanattga tttaaggaag aaatggacaa gaacacatag aaaccgtcag atctggaaga    360

tcaatgttcc anatcaaatc gcatggagca naaccttttt atcacatcgg caaaaatccc    420

ntgggtgat                                                            429


<210> SEQ ID NO 340
<211> LENGTH: 544
<212> TYPE: DNA
<213> ORGANISM: Pinus taeda L.
<220> FEATURE:
<221> NAME/KEY: unsure
<222> LOCATION: n at 386, 456, 492 and 509.
<223> OTHER INFORMATION: n is  a or g or c or t/u, unknown or other.

<400> SEQUENCE: 340

gctcaacagt tttgtaagtg tcgaggcata tctttgctat ggtcttagtc attgggattt     60

caaaaacaaa actaccccat tttcattttt gtctgcattt ttccgtaatc ttggtgtgct    120

aaaccaaggg catgctggtt ttggaaactt tatccatatt tggtaacaca aactctcaag    180

aaaatactga ttaaggatgt ctaatacata atggaaggta acccaagact cagtgaacta    240

gctttgattt tgaaagcata atgagccctt ctcgttactc ataatttata aattggcagg    300

tgtgtgtgtg tgtgtgtgtg tgcgtgtaca cattaccatg caaaggaacg ccgatgactt    360

taaatggagg ctaaggtgtt taacanaggg gagtgttgtg ttaaatgggg gggagggaca    420

catattcttg atatggaagt gtgtgacacc tcttcnagat tttgtgagga acaatgaatc    480

tgaacaatgt cntgangata aactcgacna taaaaaatgc cacaatgtaa taaaatgcat    540

tggt                                                                 544


<210> SEQ ID NO 341
<211> LENGTH: 514
<212> TYPE: DNA
<213> ORGANISM: Pinus taeda L.
<220> FEATURE:
<221> NAME/KEY: unsure
```

<222> LOCATION: n at 26, 368 and 495.
<223> OTHER INFORMATION: n is a or g or c or t/u, unknown or other.

<400> SEQUENCE: 341

```
ccttgttata tctagcttca tcgaangtgg tcgttacctc cttaccctcg aatacctaga     60
ctcaaggtgt taattaaaag gtaatttagt tagaaacata accaagctag caagaggagt    120
agcatcacta gatatccgag actttgaacc ttggattaac gagaaacaca cataattcta    180
tatttttatg atacaaaggt ttcttttctt gcaggtcaat agagtgcatg gttgtgcgag    240
atcacaatat gtttgcaact atgctagatt agtaggaagt tttgagatca tcgacaaccg    300
tgtgtgtgtg tgtgtgtgtg tgtgtgtgtg tgtgtgtgtg tgtgtgtgtg tgtgtgtgca    360
ttgtccantc aattgggttt attttaggtg gttagttgta gtgattggga tcctccccac    420
ccaatttcaa ttccctcaag tgacatgatt agctttgata taatggttta gacccttgtt    480
gttgagaatg aatantccct aagattaacg ggat                                514
```

<210> SEQ ID NO 342
<211> LENGTH: 404
<212> TYPE: DNA
<213> ORGANISM: Pinus taeda L.
<220> FEATURE:
<221> NAME/KEY: unsure
<222> LOCATION: n at 116 and 194.
<223> OTHER INFORMATION: n is a or g or c or t/u, unknown or other.

<400> SEQUENCE: 342

```
acaaatgctc aatatagacc acttgcatca tatttgtttg ttgatctaga tgaatgatgg     60
tgcgcgcgcg cacacacaca cacacacaca cacacatgta tgagatagtt aacaangttg    120
atgacaggtt gattattcct tttgttgaat tatggctatt tgattgagag aattttgttg    180
aaggatttta gtantaagat gtgttgttga gttagagttg tatgaatgct taagattgag    240
agtatggatg aggacaaagt atgctactgc caaatcatat gatgttaaca ttgatgtcta    300
agtatatgtt gatgatggag agtgattttg tggtttaatg ctgctagatt ttgtattgca    360
gcaagttttt ggagtctcgg tataaaagat aagggaaaag agaa                     404
```

<210> SEQ ID NO 343
<211> LENGTH: 388
<212> TYPE: DNA
<213> ORGANISM: Pinus taeda L.

<400> SEQUENCE: 343

```
acatacatgt catgtaggct tgaggtggat atgtccaaaa gtcatgtctc ctcaaggaat     60
tcattggagc cacatgtgaa tatatatgtg tgtgtgtgtg tgtgtgtgtg aggttattag    120
accatccaag agaaacattt catagagaga tcatctccaa tggtagccac aacacaagaa    180
ggaaggggtc gaggagaaca agggaaaatt tgaggtatgt tttatgggtt tgatatggcc    240
aaagtgtaga agaggatagc caagtgaatt atgggcagta aggtgcatat tttagggtgt    300
aattctcctt gttttggagg gccacaagct ctgtgggaca tggtagatac cgtgggattt    360
ttttgggatt actggagggg tcataagg                                       388
```

<210> SEQ ID NO 344
<211> LENGTH: 418
<212> TYPE: DNA
<213> ORGANISM: Pinus taeda L.
<220> FEATURE:
<221> NAME/KEY: unsure
<222> LOCATION: n at 337, 362, 385 and 409.

<223> OTHER INFORMATION: n is a or g or c or t/u, unknown or other.

<400> SEQUENCE: 344

```
atccttagta acagttgttc tctgtttaca cagagaacat tgtgaaaaca tgggaaattt     60

cgtagaaaac atagctccta gacttgaaat tctcataaca ccactttata gtgccatcgg    120

gtccgtctat tggttgtcgt cgcttattgc aatggctctt tctccttcac atttcgttta    180

agaaatgaaa ttgtgaaaat acattaaaaa gggggtgttt gatggatctc gagatccata    240

taatatggct tgtaatatta tcgggtccaa tccatcggat cacccatata tatatatgtg    300

tgtgtgtgtg tgtgtgtgtg tgtgtgtgtg tgtgtgngca tgcatgtcta tccctgcttt    360

gntgtgttcg ctgatttcga tccgncaata tcggngatca tggtatcgna tcagcatc      418
```

<210> SEQ ID NO 345
<211> LENGTH: 527
<212> TYPE: DNA
<213> ORGANISM: Pinus taeda L.

<400> SEQUENCE: 345

```
atcacctagt ctgcccctag tgtgatgttt cttatctcca aagagtcttc cttgtaaacg     60

agactcacaa agtgaatttt ttcactcttt attttactaa tttgaagttt tcatgacctt    120

ggagtggatt cacacacaca cacacacaca cacacacaca tattttttta caaaatgtta    180

atattttatg tatttttttgg ttgactagtc cagttttgat gacattgttg aggaagttgt    240

gactgttatt gcgaaatata acatcgcagt gcaaagttca ctaagcactc tagaatagga    300

gcaacaatgg gatcaatcac cagtgtaagc gtagcaacca ttcccccgct attctgtggt    360

tggatattat ccccacaagg gagtcttccc tagtagaatt tagggactat ataatgttaa    420

gcccttaata agcctcatgt tacccataaa cctcttatta agccctagat attgagtgat    480

tacttatcta ttggtatatt ggtatgtagg ctataacccc tcatggt                  527
```

<210> SEQ ID NO 346
<211> LENGTH: 469
<212> TYPE: DNA
<213> ORGANISM: Pinus taeda L.
<220> FEATURE:
<221> NAME/KEY: unsure
<222> LOCATION: n at 260, 322, 378, 446 and 457.
<223> OTHER INFORMATION: n is a or g or c or t/u, unknown or other.

<400> SEQUENCE: 346

```
gctagcatgt aaatgtgtaa acccaggcta ggctgaggca catttaagca taggagggat     60

aacactcgtt tgtatcttta tacataatat gtgcgtgtgt gtgtgtgtgt gtgtgtgtgt    120

gtgtgtgtgt gtgtgtgtgt gtgtgtgcag gctacagttn gaggggcttt gtgaaatcat    180

atgtatgaca agccaaattt tggagtaaga ccccaaattc ataccaataa ccactacatc    240

taatacttgg actaantccn tcgaaaaacc actgggttca agccttatgc atatctatgt    300

gcatatgcat caatcggggg tngagtctct gttggcatta tggcatatgt tngatgctat    360

ggctctggtg ttgtcctnga tggcaactca acttggtgac aaatcccaga tcaggcaccc    420

agaaagaaga aaaagtcata tacgcnggtt catctanaca aagacgtgt                469
```

<210> SEQ ID NO 347
<211> LENGTH: 451
<212> TYPE: DNA
<213> ORGANISM: Pinus taeda L.

<400> SEQUENCE: 347

```
atctctcttc gttgggcata tttcctacca taaatcacag cccaagtcta tgacctactg     60

taacattcta gcatgcccca catattttta tcaaacacag gtctcgcaat acatctaatt    120

acagattaag gaattggatt acattttgcc atgaagtgga aaattttact ttgttcaccg    180

cacaatagtc atattcaaat tcttaccttc cttttgtgtg tgtgtgtgtg tgtgtgtgtg    240

tgtgtatata tatatataaa gaggagagac atccaccaca aagaaactat tggatttcct    300

cttagaactt aaaaaaaaaa acattaacaa tttcaattaa ggacaaagag aaataatttt    360

tctttttgc cacacctatt gaaaatagaa acaagaaaat gctaaaaata gaagtgctaa    420

aaataacact tctataaatc gcaatttggg t                                  451
```

```
<210> SEQ ID NO 348
<211> LENGTH: 382
<212> TYPE: DNA
<213> ORGANISM: Pinus taeda L.
<220> FEATURE:
<221> NAME/KEY: unsure
<222> LOCATION: n at 153, 320, 343 and 346.
<223> OTHER INFORMATION: n is  a or g or c or t/u, unknown or other.

<400> SEQUENCE: 348
```

```
ccttgtgagg ctaaaaagga gaagaggaat ttttttttat ggtgttgtgg agaagagaat     60

ttgagaaagg attgtccctg aaggaagaag atgaaataag ttagccacta tgagccacac    120

aaacatgcat caacgatgca ggatgttgag aangaggacg gggcttcccc tcaagctcct    180

tcacacacac acacacacac acacacacac acacacacac acacacacac acacacacac    240

acacacacac acatatacat atttgtgtgt gtgtgtgtcg aaaatatccc tcgtgaactt    300

ttgggaaatg taagacttcn aggttattgt gagccttgtg aanaantctt gatgtgattt    360

tggtatatga ttatgcgtat gt                                             382
```

```
<210> SEQ ID NO 349
<211> LENGTH: 588
<212> TYPE: DNA
<213> ORGANISM: Pinus taeda L.
<220> FEATURE:
<221> NAME/KEY: unsure
<222> LOCATION: n at 587.
<223> OTHER INFORMATION: n is  a or g or c or t/u, unknown or other.

<400> SEQUENCE: 349
```

```
acaatcactc ctgtattaat tagaagagtc aaaattctct taagcaatgt atctatctat     60

ctatctatct atctatctat atatatatat ccaaaaattc ctcagcaatt gatccctaca    120

aatgaggcat gagggtgaag cttatcacaa tgcacaaaga gaaggcaaga tttaccttgg    180

gaaaacccac taaggggaaa aaactaacaa ccttttcaat agagaaatgc ttttgttcaa    240

caagggacac acctagaccc ttctagtcat taaatagttc acacttggtc aaaccatcta    300

agtcaagcct cccaatctaa tccaacactt ggcatttaca gatctaccca aaatttcaac    360

cctcttgcaa ctgctagatt cccaaaattt cggccccatg caactgccta gaatttcagc    420

acctacaatg gaaactgctc ataaatatgt gaactatcga tagatagata gatagagata    480

gatagataga tagatagata gagagagaga gagagagaga gagagagaga gagagagaga    540

gtatcccacg tgcgagcttg agagagagag agaaatagag atgccant                588
```

```
<210> SEQ ID NO 350
<211> LENGTH: 315
<212> TYPE: DNA
```

<213> ORGANISM: Pinus taeda L.

<400> SEQUENCE: 350
cccgctccta ttcaagatca aaagaaggat atgttaaagg tcaagtgctt catttgtcaa 60
aactttggac actatgcatc aacaaccaat gttgttgttg atgatgatga tgatgatgag 120
catccacctc aaaagaagtc aaaggaattc ttcctttagg agctactacc aataatgctt 180
gagggtaatt atgcctctag gcgcctgatc ggtttccaag attctcttat aggtttttag 240
ggarggagtt gacaatcctc aacaatttct tccttaatca acagataagt atgtcatatt 300
tttctcttga ttatt 315

<210> SEQ ID NO 351
<211> LENGTH: 345
<212> TYPE: DNA
<213> ORGANISM: Pinus taeda L.
<220> FEATURE:
<221> NAME/KEY: unsure
<222> LOCATION: n at 30, 70, 80, 191, 307, 310, 315, 328 and 343.
<223> OTHER INFORMATION: n is a or g or c or t/u, unknown or other.

<400> SEQUENCE: 351
cctttctgaa tgacaaaagg gcttctacgn ccttcctatc gtcagcgtcc atggatgatg 60
atgatgatgn aaattcaggn tgctccacag tgccttcatc gtccttcaaa agagattgaa 120
gagaagcact tccaccagtc gtgcgctcat acagatgatc atggtgtaaa gcatgacccc 180
tgtgaacatg ngagtaatga tatggcttca tggaataact aatagttgcc aggagaagaa 240
gccacactag tatgattatc gacacagcac ttttctcctt tctctcttta tctcaattcg 300
aaagaantcn aagantggcc tgtgattncc ttgtttgcgg gcncc 345

<210> SEQ ID NO 352
<211> LENGTH: 368
<212> TYPE: DNA
<213> ORGANISM: Pinus taeda L.
<220> FEATURE:
<221> NAME/KEY: unsure
<222> LOCATION: n at 334, 344 and 359.
<223> OTHER INFORMATION: n is a or g or c or t/u, unknown or other.

<400> SEQUENCE: 352
attgaaacca atttttcccc tttttaatgt aaaaaatatc aaaataaata acaaattata 60
taataattca ttataaaaca atataaattt taacatatat atgaactttg aaataaacct 120
taatggtgat gatgatgatg atggtggtgg ttaacgtcca ctgagaccaa attggtctat 180
cggacctata atttcttagt ttttacttat ctggctcctt gtctttcttg gcgagattag 240
tgttgtagct ttcttttttt tctctacagt cttccaactt cctttatctt gcatctccct 300
ccactcctct cgttccttgg gaaattggtg tctnacttcc caanccatng tgtttcatcc 360
tttgaagg 368

<210> SEQ ID NO 353
<211> LENGTH: 320
<212> TYPE: DNA
<213> ORGANISM: Pinus taeda L.
<220> FEATURE:
<221> NAME/KEY: unsure
<222> LOCATION: n at 259 and 278.
<223> OTHER INFORMATION: n is a or g or c or t/u, unknown or other.

<400> SEQUENCE: 353
ccctgagaca tccaatccat gtgtttttct accatttatt tatcatttta ttttccttct 60

-continued

```
tcttcataat ttgattagtc ttcttcttct tcttcttctc cgcccaactc atgtaaagta    120

tcatctaaga gcactacatt atcaccatca ccatcattta aggttgaagg tttttctagt    180

ttttctatat tttatttaga gtctaactat tcaagggtgg taagaaccaa ctcttcaact    240

gttgacacca ttatcctant gggggtggtt tggttctnat tcacaaaata cggaaaagtt    300

tctattctgg atcctttaga                                                320


<210> SEQ ID NO 354
<211> LENGTH: 349
<212> TYPE: DNA
<213> ORGANISM: Pinus taeda L.

<400> SEQUENCE: 354

cctcttccta gtagggggat tacttggagg aggatccgag gggtccatag ggtccatgcg     60

atcatcatca acctcctttt tcggcttagg catagaggga ccctctagta ggtccatagc    120

attatctttt ttctagtagg tctctagcta atccaaagga aacatatcca tcgaaagtta    180

catccttgat aaactcgatc ttccttttgc tatatgtgtg tgtgtgtgtg tgtgtgtgtg    240

atttagagtt ttcacaatat ccaacaaaca tatctttctt tatggtggct tccaacttgt    300

tcctcttgtc cttcngcaca tggaaatata cgggacaacc aaatatcat                349


<210> SEQ ID NO 355
<211> LENGTH: 30
<212> TYPE: DNA
<213> ORGANISM: Pinus taeda L.

<400> SEQUENCE: 355

accaccacca ccaccaccat catcatcatc                                      30


<210> SEQ ID NO 356
<211> LENGTH: 52
<212> TYPE: DNA
<213> ORGANISM: Pinus taeda L.

<400> SEQUENCE: 356

ttgttgttgt tgtctcttat tattattatt attattatta ttattattat ta             52


<210> SEQ ID NO 357
<211> LENGTH: 24
<212> TYPE: DNA
<213> ORGANISM: Pinus taeda L.

<400> SEQUENCE: 357

tattattatt attattatta ttat                                            24


<210> SEQ ID NO 358
<211> LENGTH: 37
<212> TYPE: DNA
<213> ORGANISM: Pinus taeda L.

<400> SEQUENCE: 358

aaaaaacaaa aaaaacaaac aaacaaacaa acaaaaa                              37


<210> SEQ ID NO 359
<211> LENGTH: 27
<212> TYPE: DNA
<213> ORGANISM: Pinus taeda L.

<400> SEQUENCE: 359
```

-continued aaacaaacaa acaaacaaac aaaaaaa 27

<210> SEQ ID NO 360
<211> LENGTH: 32
<212> TYPE: DNA
<213> ORGANISM: Pinus taeda L.

<400> SEQUENCE: 360
aaataaataa ataaataaat aaataaataa at 32

<210> SEQ ID NO 361
<211> LENGTH: 16
<212> TYPE: DNA
<213> ORGANISM: Pinus taeda L.

<400> SEQUENCE: 361
aaataaataa ataaat 16

<210> SEQ ID NO 362
<211> LENGTH: 16
<212> TYPE: DNA
<213> ORGANISM: Pinus taeda L.

<400> SEQUENCE: 362
aaataaataa ataaat 16

<210> SEQ ID NO 363
<211> LENGTH: 44
<212> TYPE: DNA
<213> ORGANISM: Pinus taeda L.

<400> SEQUENCE: 363
aaataaataa ataaataaat aaataaataa ataaataaat aaat 44

<210> SEQ ID NO 364
<211> LENGTH: 33
<212> TYPE: DNA
<213> ORGANISM: Pinus taeda L.

<400> SEQUENCE: 364
attattatta ttattattat tattattatt att 33

<210> SEQ ID NO 365
<211> LENGTH: 36
<212> TYPE: DNA
<213> ORGANISM: Pinus taeda L.

<400> SEQUENCE: 365
attattatta ttattattat tattattatt attatt 36

<210> SEQ ID NO 366
<211> LENGTH: 20
<212> TYPE: DNA
<213> ORGANISM: Pinus taeda L.

<400> SEQUENCE: 366
ccctagggaa aggtttccac 20

<210> SEQ ID NO 367
<211> LENGTH: 20
<212> TYPE: DNA
<213> ORGANISM: Pinus taeda L.

<400> SEQUENCE: 367
ggtcccatag accaatttgg 20

<210> SEQ ID NO 368
<211> LENGTH: 23
<212> TYPE: DNA
<213> ORGANISM: Pinus taeda L.

<400> SEQUENCE: 368
gatcaatcat caaattcatc acc 23

<210> SEQ ID NO 369
<211> LENGTH: 20
<212> TYPE: DNA
<213> ORGANISM: Pinus taeda L.

<400> SEQUENCE: 369
gttgcagatg aggctaaggc 20

<210> SEQ ID NO 370
<211> LENGTH: 21
<212> TYPE: DNA
<213> ORGANISM: Pinus taeda L.

<400> SEQUENCE: 370
ccaatttggt ctcagtggat g 21

<210> SEQ ID NO 371
<211> LENGTH: 20
<212> TYPE: DNA
<213> ORGANISM: Pinus taeda L.

<400> SEQUENCE: 371
gagatgcccc taggttctcc 20

<210> SEQ ID NO 372
<211> LENGTH: 20
<212> TYPE: DNA
<213> ORGANISM: Pinus taeda L.

<400> SEQUENCE: 372
tccacagcca tcaccactta 20

<210> SEQ ID NO 373
<211> LENGTH: 20
<212> TYPE: DNA
<213> ORGANISM: Pinus taeda L.

<400> SEQUENCE: 373
tgggtccgat agaccaatgt 20

<210> SEQ ID NO 374
<211> LENGTH: 20
<212> TYPE: DNA
<213> ORGANISM: Pinus taeda L.

<400> SEQUENCE: 374
taaggtttca ccaagggctg 20

<210> SEQ ID NO 375
<211> LENGTH: 20
<212> TYPE: DNA
<213> ORGANISM: Pinus taeda L.

<400> SEQUENCE: 375
tcatggggtc aattctcctc 20

<210> SEQ ID NO 376
<211> LENGTH: 23
<212> TYPE: DNA
<213> ORGANISM: Pinus taeda L.

<400> SEQUENCE: 376
atggatggaa aatttctata gcc 23

<210> SEQ ID NO 377
<211> LENGTH: 23
<212> TYPE: DNA
<213> ORGANISM: Pinus taeda L.

<400> SEQUENCE: 377
atgtttccaa ttaaaggatt tcc 23

<210> SEQ ID NO 378
<211> LENGTH: 20
<212> TYPE: DNA
<213> ORGANISM: Pinus taeda L.

<400> SEQUENCE: 378
gccttgcaaa gtgacctctc 20

<210> SEQ ID NO 379
<211> LENGTH: 20
<212> TYPE: DNA
<213> ORGANISM: Pinus taeda L.

<400> SEQUENCE: 379
tccatgacaa cccagttcaa 20

<210> SEQ ID NO 380
<211> LENGTH: 20
<212> TYPE: DNA
<213> ORGANISM: Pinus taeda L.

<400> SEQUENCE: 380
gagaacgcgc gactgtatta 20

<210> SEQ ID NO 381
<211> LENGTH: 20
<212> TYPE: DNA
<213> ORGANISM: Pinus taeda L.

<400> SEQUENCE: 381
tttcccatct ggttcatgtg 20

<210> SEQ ID NO 382
<211> LENGTH: 22
<212> TYPE: DNA
<213> ORGANISM: Pinus taeda L.

<400> SEQUENCE: 382
ccaattcttt gaagtattat ag 22

<210> SEQ ID NO 383
<211> LENGTH: 20
<212> TYPE: DNA
<213> ORGANISM: Pinus taeda L.

<400> SEQUENCE: 383
gatcgcgaag ctaagacacc 20

<210> SEQ ID NO 384
<211> LENGTH: 20
<212> TYPE: DNA
<213> ORGANISM: Pinus taeda L.

<400> SEQUENCE: 384
tcgatcacag tgttggcatt 20

<210> SEQ ID NO 385
<211> LENGTH: 20
<212> TYPE: DNA
<213> ORGANISM: Pinus taeda L.

<400> SEQUENCE: 385
gccaagccca ttcagtttta 20

<210> SEQ ID NO 386
<211> LENGTH: 20
<212> TYPE: DNA
<213> ORGANISM: Pinus taeda L.

<400> SEQUENCE: 386
agaggttgca ggaagcaaaa 20

<210> SEQ ID NO 387
<211> LENGTH: 20
<212> TYPE: DNA
<213> ORGANISM: Pinus taeda L.

<400> SEQUENCE: 387
attggtttct ccatcgttgc 20

<210> SEQ ID NO 388
<211> LENGTH: 20
<212> TYPE: DNA
<213> ORGANISM: Pinus taeda L.

<400> SEQUENCE: 388
aggcgaagct tatggaacaa 20

<210> SEQ ID NO 389
<211> LENGTH: 20
<212> TYPE: DNA
<213> ORGANISM: Pinus taeda L.

<400> SEQUENCE: 389
tgtttcccga tcctctgttc 20

<210> SEQ ID NO 390
<211> LENGTH: 21
<212> TYPE: DNA
<213> ORGANISM: Pinus taeda L.

<400> SEQUENCE: 390
atgatgatga tgatgatgat g 21

<210> SEQ ID NO 391
<211> LENGTH: 18
<212> TYPE: DNA

-continued

```
<213> ORGANISM: Pinus taeda L.

<400> SEQUENCE: 391

atgatgatga tgatgatg                                              18


<210> SEQ ID NO 392
<211> LENGTH: 18
<212> TYPE: DNA
<213> ORGANISM: Pinus taeda L.

<400> SEQUENCE: 392

catcatcatc atcatcat                                              18


<210> SEQ ID NO 393
<211> LENGTH: 57
<212> TYPE: DNA
<213> ORGANISM: Pinus taeda L.

<400> SEQUENCE: 393

attattatta ttattattat tattattatt attattatta ttattattat tattatt      57


<210> SEQ ID NO 394
<211> LENGTH: 21
<212> TYPE: DNA
<213> ORGANISM: Pinus taeda L.

<400> SEQUENCE: 394

tattattatt attattatta t                                           21


<210> SEQ ID NO 395
<211> LENGTH: 21
<212> TYPE: DNA
<213> ORGANISM: Pinus taeda L.

<400> SEQUENCE: 395

attattatta ttattattat t                                           21


<210> SEQ ID NO 396
<211> LENGTH: 18
<212> TYPE: DNA
<213> ORGANISM: Pinus taeda L.

<400> SEQUENCE: 396

aataataata ataataat                                              18


<210> SEQ ID NO 397
<211> LENGTH: 30
<212> TYPE: DNA
<213> ORGANISM: Pinus taeda L.

<400> SEQUENCE: 397

ttcttcttct tcttcttctt cttcttcttc                                 30
```